(12) United States Patent
Lee et al.

(10) Patent No.: US 7,592,357 B2
(45) Date of Patent: Sep. 22, 2009

(54) COMPOUNDS

(75) Inventors: Dennis Lee, King of Prussia, PA (US); Krista B. Goodman, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 224 days.

(21) Appl. No.: 10/589,995

(22) PCT Filed: Feb. 18, 2005

(86) PCT No.: PCT/US2005/005345

§ 371 (c)(1),
(2), (4) Date: Aug. 18, 2006

(87) PCT Pub. No.: WO2005/082890

PCT Pub. Date: Sep. 9, 2005

(65) Prior Publication Data

US 2008/0058384 A1    Mar. 6, 2008

Related U.S. Application Data

(60) Provisional application No. 60/546,160, filed on Feb. 20, 2004.

(51) Int. Cl.
  *A61K 31/4709* (2006.01)
  *A61K 31/4439* (2006.01)
  *C07D 401/12* (2006.01)
  *C07D 401/14* (2006.01)
(52) U.S. Cl. .................. 514/314; 514/338; 546/167; 546/275.7
(58) Field of Classification Search .............. 546/275.7, 546/167; 514/338, 314
See application file for complete search history.

(56) References Cited

U.S. PATENT DOCUMENTS

| 5,328,918 | A | 7/1994 | Effland et al. |
| 2008/0125427 | A1 | 5/2008 | Sehon et al. ............. 514/234.5 |

FOREIGN PATENT DOCUMENTS

| EP | 1 403 255 | 3/2004 |
| WO | WO02/100833 | 12/2002 |

*Primary Examiner*—Patricia L Morris
(74) *Attorney, Agent, or Firm*—Reid S. Willis; John Lemanowicz

(57) ABSTRACT

Novel Inhibitors of Rho-kinases are disclosed.

17 Claims, No Drawings

COMPOUNDS

This application claims the benefit of U.S. Provisional Application No. 60/546,160, filed Feb. 20, 2004.

SUMMARY OF THE INVENTION

The present invention involves novel pyridone derivations as Rho-kinase inhibitors.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signalling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied families of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signalling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylgeranyllization and farnesylation) and activation of its intrinsic GTPase activity. Activated RhoA is capable of interacting with several effector proteins including Rho-Kinases (ROCK 1 and ROCK 2, referred to below as 'ROCK' or 'ROCKs') and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates b-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomenon is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

The present inventors have discovered novel indazole compounds, which are inhibitors of ROCK activity and show interesting selectivity over ether protein kinases. Such derivatives are useful in the treatment of disorders associated with inappropriate ROCK activity.

DESCRIPTION OF THE INVENTION

The present invention includes compounds as described herein below: The present invention thus provides compounds of the general formula (I)

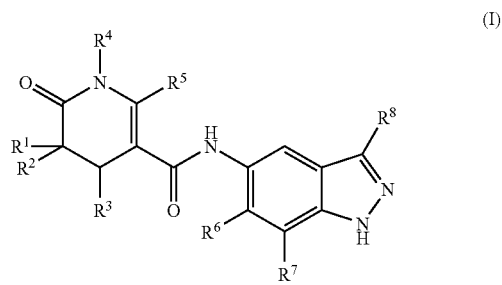

and physiologically acceptable salts wherein:
$R^1$ and $R^2$, are, independently selected from the group consisting of hydrogen and optionally substituted $C_1$-$C_6$ alkyl such that $R^1$ and $R^2$ can represent a ring;

$R^3$ is selected from the group consisting of optionally substituted $C_1$-$C_6$ alkyl, optionally substituted $C_1$-$C_6$ alkenyl, optionally substituted $C_1$-$C_6$ alkynyl and optionally substituted aryl or heteroaryl;

$R^4$ is selected from the group consisting of hydrogen, optionally substituted aralkyl, $CH_2CONR^9R^{10}$, and optionally substituted $C_1$-$C_6$ alkyl, such that $R^4$ and $R^5$ can represent a ring;

$R^5$ is selected from the group consisting of optionally substituted $C_1$-$C_3$ alkyl, such that $R^4$ and $R^5$ can represent a ring;

$R^6$ is selected from the group consisting of chlorine, fluorine or hydrogen;

$R^7$ and $R^8$, are, independently selected from the group consisting of hydrogen, halogen, and optionally substituted $C_1$-$C_3$ alkyl; and $R^9$ and $R^{10}$ are independently selected from hydrogen, $C_1$-$C_6$ alkyl, $C_3$-$C_7$ cycloalkyl, or together form a ring containing up to 6 carbons in the backbone.

It will be appreciated that any of the substituents $R^1$ to $R^5$ and $R^7$ to $R^{10}$ as defined in formula (I) above may contain at least one asymmetric center and it is to be understood that the invention includes all possible enantiomers arising therefrom and mixtures thereof including racemates.

The present invention thus provides compounds of the general formula (II)

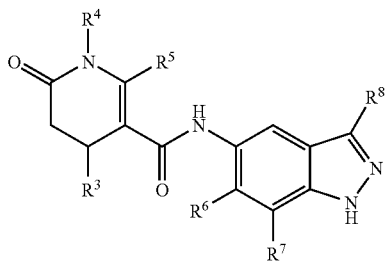

(II)

and physiologically acceptable salts wherein:

$R^3$ is selected from the group consisting of optionally substituted $C_1$-$C_6$ alkyl, optionally substituted $C_1$-$C_6$ alkenyl, optionally substituted $C_1$-$C_6$ alkynyl and optionally substituted aryl or heteroaryl;

$R^4$ is selected from the group consisting of hydrogen or optionally substituted $C_1$-$C_2$ alkyl;

$R^5$ is selected from the group consisting of optionally substituted $C_1$-$C_2$ alkyl;

$R^6$ is selected from the group consisting of chlorine, fluorine or hydrogen;

$R^7$ and $R^8$, are independently selected from the group consisting of hydrogen, halogen, and optionally substituted $C_1$-$C_3$ alkyl; and $R^9$ and $R^{10}$ are independently selected from hydrogen or $C_1$-$C_6$ alkyl.

It will be appreciated that any of the substituents $R^1$ to $R^5$ and $R^7$ to $R^{10}$ as defined in formula (II) above may contain at least one asymmetric center and it is to be understood that the invention includes all possible enantiomers arising therefrom and mixtures thereof including racemates.

The term alkyl as a group or part of a group e.g. alkoxy, alkylthio, alkylamino, dialkylamino, optionally substituted alkyl e.g. aminoalkyl, cycloalkylalkyl, aralkyl, heteroarylalkyl or heterocyclylalkyl refers to a $C_1$-$C_6$ straight or branched chain alkyl group.

The term halogen includes fluorine, chlorine, bromine or iodine.

The term aryl as a group or part of a group e.g. aryloxy, aralkyl or arylamino refers to an optionally substituted phenyl or fused bicyclic aryl group e.g. naphthyl. The terms aryl, optionally substituted phenyl, heteroaryl, $C_3$-$C_7$ cycloalkyl as a group or part of a group and 4-7 membered heterocyclyl as a group or part of a group includes such groups which are optionally substituted with 1 to 3 substituents which may be the same or different and selected from halogen, aryl, heteroaryl, heterocyclylalkyl, hydroxy, alkyl, alkoxy, trifluoroalkyl, amino, alkylamino, dialkylamino, arylamino, heteroarylamino, heterocyclylamino, acylamino, aminoalkyl, alkylaminoalkyl, dialkylaminoalkyl, acylaminoalkyl, arylaminoalkyl, heteroarylaminoalkyl, cycloalkylaminoalkyl, heteroclylaminoalkyl, hydroxyalkyl, $CONR^9R^{10}$, $CSNR^9R^{10}$, $CH_2CONR^9R^{10}$, carboxamido, alkoxycarbonyl, aminoalkoxy, dialkylaminoalkoxy, acylaminoalkoxy, sulphonamido, aminosulphonyl, cyano, formyl, nitro, $R^{11}O$ or $R^{11}S(O)_n$, wherein $R^{11}$ is a group selected from alkyl, aryl, heteroaryl or heterocyclylalkoxy and n is zero, one or two, or each of the said groups can form part of a fused bicyclic ring system containing up to 10 ring members and which can be at least partially saturated.

The term heteroaryl as a group or part of a group e.g. heteroaryloxy refers to a 5, or 6 membered ring or a fused 5,6 or 6,6 bicyclic ring system. When heteroaryl represents a 5 membered group it contains a heteroatom selected from O, N or S and may optionally contain a further 1 to 3 nitrogen atoms. Examples of such groups include furanyl, thienyl, isoxazolyl, oxazolyl or imidazolyl.

When heteroaryl represents a 6-membered group it contains from 1 to 3 nitrogen atoms. Examples of such groups include pyridyl, pyrimidinyl, or triazinyl. The term 5,6 fused bicyclic heteroaryl group refers to a group in which the 5-membered ring contains an oxygen, sulphur or NH group and may optionally contain a further 1 to 2 nitrogen atoms, and the 6 membered ring optionally contains from 1 to 3 nitrogen atoms. Examples of such groups include benzofuranyl, benzothienyl, benzimidazole, benzotriazole or indolyl.

The term 6,6-fused bicyclic heteroaryl group refers to a bicyclic heteroaryl group which contains at least one nitrogen atom in one of the rings and may contain up to 3 nitrogen atoms in each ring. Examples of such groups include quinolinyl, isoquinolinyl or naphthyridinyl also the term 6,6 fused bicyclic heteroaryl group refers to a 6-membered heteroaryl group which is fused to a partially saturated carbocyclic group. Examples of such a group includes tetrahydroquinolinyl or tetrahydroisoquinolinyl.

The term heterocyclyl as a group or part of a group e.g. heterocyclylalkyl or heterocyclylalkylidene refers to a bridged heterocyclic group or a 4-7 membered heterocyclyl group which is linked to the rest of the compound of formula (I) via a carbon or nitrogen atom in that group and which contains one or two hetero atoms selected from N, O or $S(O)_n$, and when the heterocyclyl group contains a ring member NH or the heterocyclyl group is substituted by a primary or secondary amino group then the term also includes N-alkyl, N-optionally substituted phenyl, N-araalkyl, N-sulfonyl, or, N-acyl derivatives thereof. The term heterocyclic also includes bridged heterocyclic. Examples of such heterocyclic groups include optionally substituted pyrrolidine, piperidine, piperazine, homopiperazine, morpholine, thiomorpholine and (8-methyl-8-aza-bicyclo[3.2.1]oct-3-yl)-amine.

The term cycloalkyl as a group or part of a group e.g. cycloalkylalkyl or cycloalkylidene refers to a 3-7 membered carbocyclic group.

The term fused bicyclic ring system containing up to 11 ring members and which is at least partially saturated includes carbocyclic and heterocyclic 6,5, 6,6 and 6,7 bicyclic ring systems. Examples of such 6,5 and 6,6 carbocyclic ring systems include those wherein the bicyclic ring comprises a benzene ring fused to a 5-, 6- or -membered carbocyclic ring which is at least partially saturated e.g. tetrahydronaphthyl, indanyl or indenyl. Examples of such 6,5, 6,6 or 6,7 heterocyclic rings include those wherein one ring is benzene which is fused to a 5, 6 or 7 membered ring containing one or two hetero atoms selected from O, S or N e.g. indolinyl, isoindolinyl, 2,3-dihydro-1H-isoindol-5-yl, dihydrobenzofuranyl, dihydrobenzothienyl, 1,3-benzodioxolyl, benzopyrrolyl, 1,3-benozodithiolyl, 1,4-benzodioxanyl, chromanyl, chromenyl or 2,3,4,5-tetrahydro-1H-benzo[c]azepin-8-yl The term acyl as a group or part of the acylamino group refers to an alkanoyl, aroyl, aralkanoyl, alkoxycarbonyl, aryloxycaronyl or aralkoxycarbonyl group.

The compounds of formula (I) and (II) form salts with inorganic and organic acids and the invention includes such salts formed with physiologically acceptable inorganic and organic acids.

A preferred example of $R^3$ includes, but is not limited to, optionally substituted aryl (e.g. 4-fluorophenyl, 4-trifluoromethylphenyl, 2-naphthyl).

Preferred examples of $R^4$ include, but are not limited to, hydrogen and methyl.

A preferred example of $R^5$ includes, but is not limited to, $C_1$-$C_6$ alkyl (e.g. methyl).

Preferred examples of $R^6$ are hydrogen or fluorine.

A preferred example of $R^7$ is H.

Preferred examples of $R^8$ includes, but are not limited to, hydrogen, halogen (e.g. chloro or bromo) and $C_1$-$C_3$ alkyl (e.g. methyl or ethyl).

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. As used herein, treating or treatment of a disease refers to the in improved healing, prevention, or amelioration of a disease, disorder, or side effect, or a decrease in the rate of advancement of a disease or disorder.

Diseases or conditions that can be treated with the compounds and methods of this invention include hypertension, chronic and congestive heart failure, ischemic angina, cardiac hypertrophy and fibrosis, restenosis, chronic renal failure, atherosclerosis, asthma, male erectile dysfunctions, female sexual dysfunction and over-active bladder syndrome, stroke, multiple sclerosis, Alzheimer's disease, Parkinson's disease, amyotrophic lateral sclerosis, inflammatory pain, rheumatoid arthritis, irritable bowel syndrome, inflammatory bowel disease, Crohn's diseases, indications requiring neuronal regeneration, inducing new axonal growth and axonal rewiring across lesions within the CNS, spinal cord injury, acute neuronal injury, Parkinsons disease, Alzheimers disease, cancer, tumor metastasis, viral and bacterial infection, insulin resistance and diabetes.

In some embodiments, the disease to be treated is selected from hypertension, chronic and congestive heart failure, ischemic angina, asthma, male erectile dysfunction, female sexual dysfunction, stroke, inflammatory bowel diseases, spinal cord injury, glaucoma and tumor metastasis.

In still other embodiments, the disease to be treated is selected from hypertension, chronic and congestive heart failure and ischemic angina.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

In another embodiment, this invention describes a method of treating in mammals, especially including humans, a number of indications associated with Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Compounds with the general structure 6 can be prepared according to the procedure described in Scheme 1. Treatment of an appropriately substituted aldehyde 1 with 2,2-dimethyl-1,3-dioxane-4,6-dione, β-ketoester 2, and ammonium acetate provides substituted dihydropyridones 3. Compounds of general structure 4 may be synthesized from compounds of general structure 3 by conversion of the ester to a carboxylic acid. This transformation is dependent upon the type of ester used, and can be accomplished with a variety of conditions for each type of ester, examples of which can be found in the literature, specifically "Protective Groups on Organic Synthesis" by Greene and Wuts. Accordingly, R* may be alkyl, aralkyl, aryl, and the like. Acids of general structure 4 can be coupled with aminoindazoles of general formula 5 to afford substituted indazole amides 6, employing methods know to those skilled in the art (e.g. EDC, DMAP). Alternatively, acids of general structure 4 can be converted to acid chlorides (e.g. oxalyl chloride) and subsequently coupled with aminoindazoles 5 to provide amides of general formula 6. Compounds of general structure 5 can be prepared by a variety of methods known to those skilled in the art. Alternatively, compounds of general structure 6 can be accessed directly by reaction of ketoamides 7 with meldrum's acid, an appropriately substituted aldehyde 1 and ammonium acetate.

Compounds of the general structure 3 can be further transformed, Scheme 2. Treatment with base followed by reaction with an appropriate electrophile provided N-substituted pyridones of general structure 8. Compounds of general structure 9 may be synthesized from compounds of general structure 8 by conversion of the ester to a carboxylic acid. This transformation is dependent upon the type of ester used, and can be accomplished with a variety of conditions for each type of ester, examples of which can be found in the literature, specifically "Protective Groups on Organic Synthesis" by Greene and Wuts. Acids of general structure 9 can be coupled with aminoindazoles of general formula 5 to afford substi-

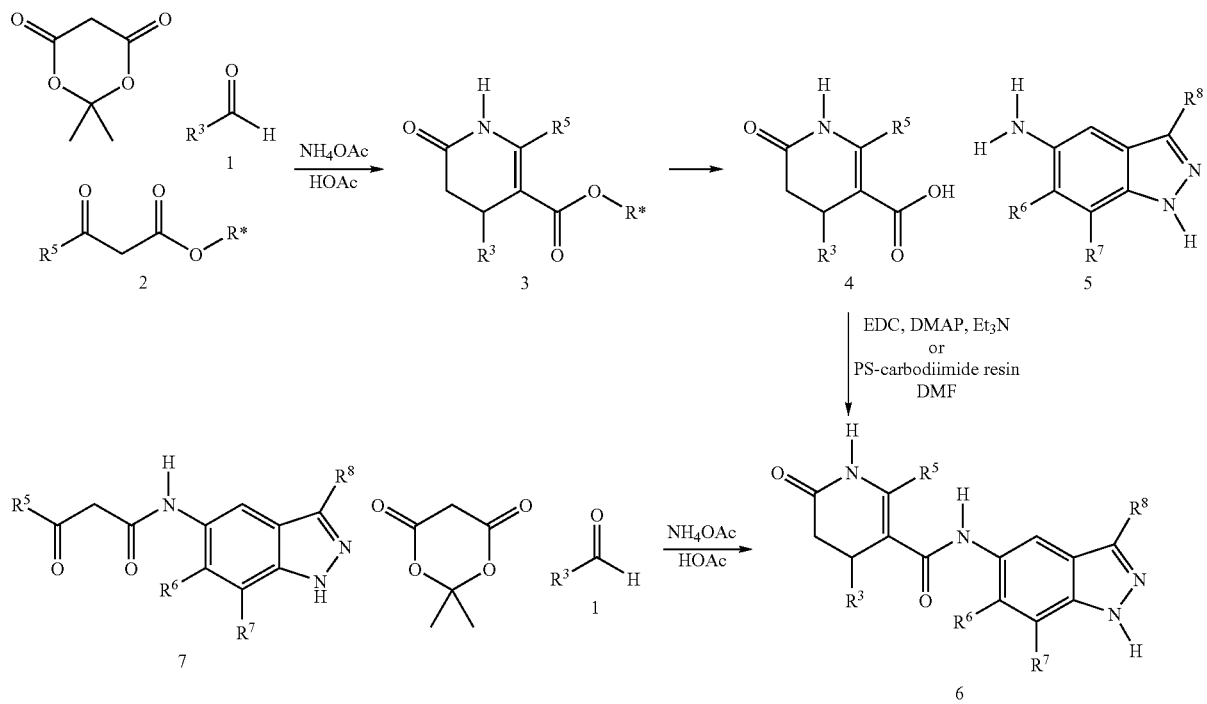

tuted indazole amides 10, employing methods know to those skilled in the art (e.g. EDC, DMAP or acid chloride coupling).

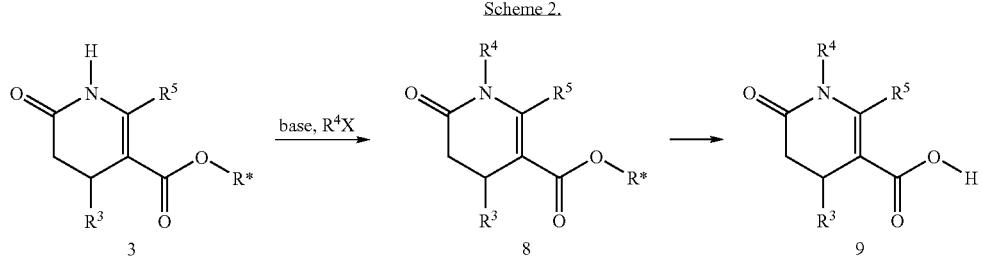

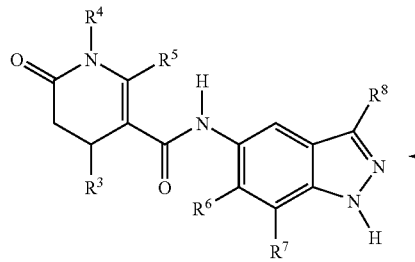
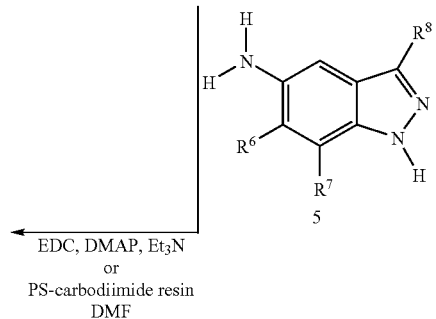

Examples of suitable compounds according to the invention include those listed below and found in Examples 1-107. These are intended to be illustrative only and not limiting in any way.

N-1H-Indazol-5-yl-2-methyl-4-(2-naphthalenyl)-6-oxo-1,4,5,6-tetrahydro-3-pyridinecarboxamide;
4-(4-Fluorophenyl)-N-1H-indazol-5-yl-2-methyl-6-oxo-1,4,5,6-tetrahydro-3-pyridinecarboxamide;
4-(4-Chloro-2-fluorophenyl)-N-1H-indazol-5-yl-2-methyl-6-oxo-1,4,5,6-tetrahydro-3-pyridinecarboxamide;
4-(4-Chlorophenyl)-N-1H-indazol-5-yl-2-methyl-6-oxo-1,4,5,6-tetrahydro-3-pyridinecarboxamide;
N-1H-Indazol-5-yl-2-methyl-6-oxo-4-[4-(trifluoromethyl)phenyl]-1,4,5,6-tetrahydro-3-pyridinecarboxamide;
4-(4-Biphenylyl)-N-1H-indazol-5-yl-2-methyl-6-oxo-1,4,5,6-tetrahydro-3-pyridinecarboxamide;
4-(3,4-Dichlorophenyl)-N-1H-indazol-5-yl-2-methyl-6-oxo-1,4,5,6-tetrahydro-3-pyridinecarboxamide;
4-(4-Fluorophenyl)-N-1H-indazol-5-yl-1,2-dimethyl-6-oxo-1,4,5,6-tetrahydro-3-pyridinecarboxamide;
4-[2-Fluoro-4-(trifluoromethyl)phenyl]-N-1H-indazol-5-yl-2-methyl-6-oxo-1,4,5,6-tetrahydro-3-pyridinecarboxamide;
N-1H-Indazol-5-yl-2-methyl-6-oxo-4-(3-quinolinyl)-1,4,5,6-tetrahydro-3-pyridinecarboxamide;
N-(3-Chloro-1H-indazol-5-yl)-2-methyl-6-oxo-4-[4-(trifluoromethyl)phenyl]-1,4,5,6-tetrahydro-3-pyridinecarboxamide;
4-(4-Chloro-2-fluorophenyl)-N-(3-chloro-1H-indazol-5-yl)-2-methyl-6-oxo-1,4,5,6-tetrahydro-3-pyridinecarboxamide;
N-(3-Chloro-1H-indazol-5-yl)-2-methyl-4-(2-naphthalenyl)-6-oxo-1,4,5,6-tetrahydro-3-pyridinecarboxamide;
N-(3-Chloro-1H-indazol-5-yl)-4-(4-fluorophenyl)-2-methyl-6-oxo-1,4,5,6-tetrahydro-3-pyridinecarboxamide;
4-(4-Chloro-2-fluorophenyl)-N-(3-chloro-1H-indazol-5-yl)-2-methyl-6-oxo-1,4,5,6-tetrahydro-3-pyridinecarboxamide;
2-Methyl-N-(3-methyl-1H-indazol-5-yl)-6-oxo-4-[4-(trifluoromethyl)phenyl]-1,4,5,6-tetrahydro-3-pyridinecarboxamide;
N-(3-Bromo-1H-indazol-5-yl)-2-methyl-6-oxo-4-[4-(trifluoromethyl)phenyl]-1,4,5,6-tetrahydro-3-pyridinecarboxamide;
N-(3-Ethyl-1H-indazol-5-yl)-2-methyl-6-oxo-4-[4-(trifluoromethyl)phenyl]-1,4,5,6-tetrahydro-3-pyridinecarboxamide;
N-(6-Fluoro-1H-indazol-5-yl)-2-methyl-6-oxo-4-[4-(trifluoromethyl)phenyl]-1,4,5,6-tetrahydro-3-pyridinecarboxamide;
N-(7-Chloro-1H-indazol-5-yl)-2-methyl-6-oxo-4-[4-(trifluoromethyl)phenyl]-1,4,5,6-tetrahydro-3-pyridinecarboxamide;
2-Methyl-N-(7-methyl-1H-indazol-5-yl)-6-oxo-4-[4-(trifluoromethyl)phenyl]-1,4,5,6-tetrahydro-3-pyridinecarboxamide;
N-(3-Chloro-1H-indazol-5-yl)-4-[2-fluoro-4-(trifluoromethyl)phenyl]-2-methyl-6-oxo-1,4,5,6-tetrahydro-3-pyridinecarboxamide;
N-(3-Bromo-1H-indazol-5-yl)-4-[2-fluoro-4-(trifluoromethyl)phenyl]-2-methyl-6-oxo-1,4,5,6-tetrahydro-3-pyridinecarboxamide;
4-[2-Fluoro-4-(trifluoromethyl)phenyl]-2-methyl-N-(3-methyl-1H-indazol-5-yl)-6-oxo-1,4,5,6-tetrahydro-3-pyridinecarboxamide;
N-(3-Ethyl-1H-indazol-5-yl)-4-[2-fluoro-4-(trifluoromethyl)phenyl]-2-methyl-6-oxo-1,4,5,6-tetrahydro-3-pyridinecarboxamide;
N-(6-Fluoro-1H-indazol-5-yl)-4-[2-fluoro-4-(trifluoromethyl)phenyl]-2-methyl-6-oxo-1,4,5,6-tetrahydro-3-pyridinecarboxamide;
4-[2-Fluoro-4-(trifluoromethyl)phenyl]-2-methyl-N-(7-methyl-1H-indazol-5-yl)-6-oxo-1,4,5,6-tetrahydro-3-pyridinecarboxamide;
N-(7-Chloro-1H-indazol-5-yl)-4-[2-fluoro-4-(trifluoromethyl)phenyl]-2-methyl-6-oxo-1,4,5,6-tetrahydro-3-pyridinecarboxamide;
4-(4-Chloro-2-fluorophenyl)-2-methyl-N-(3-methyl-1H-indazol-5-yl)-6-oxo-1,4,5,6-tetrahydro-3-pyridinecarboxamide;
N-(3-Bromo-1H-indazol-5-yl)-4-(4-chloro-2-fluorophenyl)-2-methyl-6-oxo-1,4,5,6-tetrahydro-3-pyridinecarboxamide;
4-(4-Chloro-2-fluorophenyl)-N-(3-ethyl-1H-indazol-5-yl)-2-methyl-6-oxo-1,4,5,6-tetrahydro-3-pyridinecarboxamide;
4-(4-Chloro-2-fluorophenyl)-N-(6-fluoro-1H-indazol-5-yl)-2-methyl-6-oxo-1,4,5,6-tetrahydro-3-pyridinecarboxamide;
4-(4-Chloro-2-fluorophenyl)-2-methyl-N-(7-methyl-1H-indazol-5-yl)-6-oxo-1,4,5,6-tetrahydro-3-pyridinecarboxamide;
4-(4-Chloro-2-fluorophenyl)-N-(7-chloro-1H-indazol-5-yl)-2-methyl-6-oxo-1,4,5,6-tetrahydro-3-pyridinecarboxamide;

N-(3-Bromo-1H-indazol-5-yl)-2-methyl-4-(2-naphthale-nyl)-6-oxo-1,4,5,6-tetrahydro-3-pyridinecarboxamide;
2-Methyl-N-(3-methyl-1H-indazol-5-yl)-4-(2-naphthale-nyl)-6-oxo-1,4,5,6-tetrahydro-3-pyridinecarboxamide;
N-(3-Ethyl-1H-indazol-5-yl)-2-methyl-4-(2-naphthalenyl)-6-oxo-1,4,5,6-tetrahydro-3-pyridinecarboxamide;
2-Methyl-N-(7-methyl-1H-indazol-5-yl)-4-(2-naphthale-nyl)-6-oxo-1,4,5,6-tetrahydro-3-pyridinecarboxamide;
N-(7-Chloro-1H-indazol-5-yl)-2-methyl-4-(2-naphthale-nyl)-6-oxo-1,4,5,6-tetrahydro-3-pyridinecarboxamide;
N-(3-Chloro-6-fluoro-1H-indazol-5-yl)-4-(4-chloro-2-fluorophenyl)-2-methyl-6-oxo-1,4,5,6-tetrahydro-3-pyridinecarboxamide;
4-(4-Chlorophenyl)-N-(6-fluoro-1H-indazol-5-yl)-2-methyl-6-oxo-1,4,5,6-tetrahydro-3-pyridinecarboxamide;
N-1H-Indazol-5-yl-1,2-dimethyl-6-oxo-4-[4-(trifluoromethyl)phenyl]-1,4,5,6-tetrahydro-3-pyridinecarboxamide;
4-(3-Hydroxyphenyl)-N-1H-indazol-5-yl-2-methyl-6-oxo-1,4,5,6-tetrahydro-3-pyridinecarboxamide;
4-[4-(Aminosulfonyl)phenyl]-N-1H-indazol-5-yl-2-methyl-6-oxo-1,4,5,6-tetrahydro-3-pyridinecarboxamide;
4-(4-Cyanophenyl)-N-1H-indazol-5-yl-2-methyl-6-oxo-1,4,5,6-tetrahydro-3-pyridinecarboxamide;
N-(6-Fluoro-1H-indazol-5-yl)-4-[2-fluoro-4-(trifluoromethyl)phenyl]-1,2-dimethyl-6-oxo-1,4,5,6-tetrahydro-3-pyridinecarboxamide;
4-[2-Fluoro-4-(trifluoromethyl)phenyl]-1,2-dimethyl-N-(3-methyl-1H-indazol-5-yl)-6-oxo-1,4,5,6-tetrahydro-3-pyridinecarboxamide;
N-(3-Chloro-1H-indazol-5-yl)-4-[2-fluoro-4-(trifluoromethyl)phenyl]-1,2-dimethyl-6-oxo-1,4,5,6-tetrahydro-3-pyridinecarboxamide;
4-(4-Chloro-2-fluorophenyl)-1,2-dimethyl-N-(3-methyl-1H-indazol-5-yl)-6-oxo-1,4,5,6-tetrahydro-3-pyridinecarboxamide;
4-(4-Chloro-2-fluorophenyl)-N-(3-chloro-1H-indazol-5-yl)-1,2-dimethyl-6-oxo-1,4,5,6-tetrahydro-3-pyridinecarboxamide;
4-(4-Chloro-2-fluorophenyl)-N-(6-fluoro-1H-indazol-5-yl)-1,2-dimethyl-6-oxo-1,4,5,6-tetrahydro-3-pyridinecarboxamide;
N-(3-Chloro-6-fluoro-1H-indazol-5-yl)-2-methyl-6-oxo-4-[4-(trifluoromethyl)phenyl]-1,4,5,6-tetrahydro-3-pyridinecarboxamide;
N-(3-Chloro-6-fluoro-1H-indazol-5-yl)-4-[2-fluoro-4-(trifluoro-methyl)phenyl]-2-methyl-6-oxo-1,4,5,6-tetrahydro-3-pyridinecarboxamide;
N-(3-Chloro-6-fluoro-1H-indazol-5-yl)-4-(4-chlorophenyl)-2-methyl-6-oxo-1,4,5,6-tetrahydro-3-pyridinecarboxamide;
4-(4-Chlorophenyl)-2-methyl-N-(3-methyl-1H-indazol-5-yl)-6-oxo-1,4,5,6-tetrahydro-3-pyridinecarboxamide;
N-(6-Chloro-1H-indazol-5-yl)-4-(4-chlorophenyl)-2-methyl-6-oxo-1,4,5,6-tetrahydro-3-pyridinecarboxamide;
4-(4-Chlorophenyl)-N-1H-indazol-5-yl-1,2-dimethyl-6-oxo-1,4,5,6-tetrahydro-3-pyridinecarboxamide;
4-[2-Fluoro-4-(trifluoromethyl)phenyl]-N-1H-indazol-5-yl-1,2-dimethyl-6-oxo-1,4,5,6-tetrahydro-3-pyridinecarboxamide;
4-(4-Chloro-2-fluorophenyl)-N-1H-indazol-5-yl-1,2-dimethyl-6-oxo-1,4,5,6-tetrahydro-3-pyridinecarboxamide;
N-(3-Chloro-1H-indazol-5-yl)-1,2-dimethyl-6-oxo-4-[4-(trifluoromethyl)phenyl]-1,4,5,6-tetrahydro-3-pyridinecarboxamide;
N-(6-Fluoro-1H-indazol-5-yl)-1,2-dimethyl-6-oxo-4-[4-(trifluoromethyl)phenyl]-1,4,5,6-tetrahydro-3-pyridinecarboxamide;
4-(4-Chlorophenyl)-N-(6-fluoro-1H-indazol-5-yl)-1,2-dimethyl-6-oxo-1,4,5,6-tetrahydro-3-pyridinecarboxamide;
4-(4-Chlorophenyl)-1,2-dimethyl-N-(3-methyl-1H-indazol-5-yl)-6-oxo-1,4,5,6-tetrahydro-3-pyridinecarboxamide;
N-(6-Fluoro-1H-indazol-5-yl)-4-[2-fluoro-5-(methyloxy)phenyl]-2-methyl-6-oxo-1,4,5,6-tetrahydro-3-pyridinecarboxamide;
N-(6-Fluoro-1H-indazol-5-yl)-4-[2-fluoro-3-(methyloxy)phenyl]-2-methyl-6-oxo-1,4,5,6-tetrahydro-3-pyridinecarboxamide;
4-(2-Fluoro-5-hydroxyphenyl)-N-(6-fluoro-1H-indazol-5-yl)-2-methyl-6-oxo-1,4,5,6-tetrahydro-3-pyridinecarboxamide;
4-(2-Fluoro-3-hydroxyphenyl)-N-(6-fluoro-1H-indazol-5-yl)-2-methyl-6-oxo-1,4,5,6-tetrahydro-3-pyridinecarboxamide;
4-[5-(Aminosulfonyl)-4-chloro-2-fluorophenyl]-N-(6-fluoro-1H-indazol-5-yl)-2-methyl-6-oxo-1,4,5,6-tetrahydro-3-pyridinecarboxamide;
4-[3-(Aminosulfonyl)-4-chlorophenyl]-N-(6-fluoro-1H-indazol-5-yl)-2-methyl-6-oxo-1,4,5,6-tetrahydro-3-pyridinecarboxamide;
4-[3-(Aminosulfonyl)phenyl]-N-(6-fluoro-1H-indazol-5-yl)-2-methyl-6-oxo-1,4,5,6-tetrahydro-3-pyridinecarboxamide;
4-(2,3-Difluorophenyl)-N-(6-fluoro-1H-indazol-5-yl)-2-methyl-6-oxo-1,4,5,6-tetrahydro-3-pyridinecarboxamide;
4-(2,3-Difluorophenyl)-N-1H-indazol-5-yl-2-methyl-6-oxo-1,4,5,6-tetrahydro-3-pyridinecarboxamide;
4-(2,4-Difluorophenyl)-N-(6-fluoro-1H-indazol-5-yl)-2-methyl-6-oxo-1,4,5,6-tetrahydro-3-pyridinecarboxamide;
4-(2,4-Difluorophenyl)-N-(1H-indazol-5-yl)-2-methyl-6-oxo-1,4,5,6-tetrahydro-3-pyridinecarboxamide;
N-(6-Fluoro-1H-indazol-5-yl)-4-(3-hydroxyphenyl)-2-methyl-6-oxo-1,4,5,6-tetrahydro-3-pyridinecarboxamide;
N-(6-Fluoro-1H-indazol-5-yl)-2-methyl-4-{3-[(methylsulfonyl)amino]phenyl}-6-oxo-1,4,5,6-tetrahydro-3-pyridinecarboxamide;
4-(4-Chloro-3-nitrophenyl)-N-(6-fluoro-1H-indazol-5-yl)-2-methyl-6-oxo-1,4,5,6-tetrahydro-3-pyridinecarboxamide;
4-(3-Amino-4-chlorophenyl)-N-(6-fluoro-1H-indazol-5-yl)-2-methyl-6-oxo-1,4,5,6-tetrahydro-3-pyridinecarboxamide;
4-{4-Chloro-3-[(methylsulfonyl)amino]phenyl}-N-(6-fluoro-1H-indazol-5-yl)-2-methyl-6-oxo-1,4,5,6-tetrahydro-3-pyridinecarboxamide;
N-(6-Fluoro-1H-indazol-5-yl)-2-methyl-4-[3-nitro-4-(trifluoromethyl)phenyl]-6-oxo-1,4,5,6-tetrahydro-3-pyridinecarboxamide;
4-[3-Amino-4-(trifluoromethyl)phenyl]-N-(6-fluoro-1H-indazol-5-yl)-2-methyl-6-oxo-1,4,5,6-tetrahydro-3-pyridinecarboxamide;
N-(6-Fluoro-1H-indazol-5-yl)-2-methyl-4-[3-[(methylsulfonyl)amino]-4-(trifluoromethyl)phenyl]-6-oxo-1,4,5,6-tetrahydro-3-pyridinecarboxamide;
4-[3-[(Ethylsulfonyl)amino]-4-(trifluoromethyl)phenyl]-N-(6-fluoro-1H-indazol-5-yl)-2-methyl-6-oxo-1,4,5,6-tetrahydro-3-pyridinecarboxamide;
N-(6-Fluoro-1H-indazol-5-yl)-4-(2-fluoro-5-nitrophenyl)-2-methyl-6-oxo-1,4,5,6-tetrahydro-3-pyridinecarboxamide;
N-(6-Fluoro-1H-indazol-5-yl)-4-[4-fluoro-3-(trifluoromethyl)phenyl]-2-methyl-6-oxo-1,4,5,6-tetrahydro-3-pyridinecarboxamide;

4-[2,3-Difluoro-4-(trifluoromethyl)phenyl]-N-(6-fluoro-1H-indazol-5-yl)-2-methyl-6-oxo-1,4,5,6-tetrahydro-3-pyridinecarboxamide;

N-(6-Fluoro-1H-indazol-5-yl)-4-[3-fluoro-4-(trifluoromethyl)phenyl]-2-methyl-6-oxo-1,4,5,6-tetrahydro-3-pyridinecarboxamide;

4-(4-Cyanophenyl)-N-(6-fluoro-1H-indazol-5-yl)-2-methyl-6-oxo-1,4,5,6-tetrahydro-3-pyridinecarboxamide;

4-(4-Biphenylyl)-N-(6-fluoro-1H-indazol-5-yl)-2-methyl-6-oxo-1,4,5,6-tetrahydro-3-pyridinecarboxamide;

N-(6-Fluoro-1H-indazol-5-yl)-2-methyl-6-oxo-4-[4-(2-thienyl)phenyl]-1,4,5,6-tetrahydro-3-pyridinecarboxamide;

4-(4-Bromophenyl)-N-(6-fluoro-1H-indazol-5-yl)-2-methyl-6-oxo-1,4,5,6-tetrahydro-3-pyridinecarboxamide;

4-(5-Cyano-2-fluorophenyl)-N-(6-fluoro-1H-indazol-5-yl)-2-methyl-6-oxo-1,4,5,6-tetrahydro-3-pyridinecarboxamide;

N-(6-Fluoro-1H-indazol-5-yl)-4-[2-fluoro-4-(methyloxy)phenyl]-2-methyl-6-oxo-1,4,5,6-tetrahydro-3-pyridinecarboxamide;

N-(3-Chloro-1H-indazol-5-yl)-4-[4-chloro-3-(methyloxy)phenyl]-2-methyl-6-oxo-1,4,5,6-tetrahydro-3-pyridinecarboxamide;

N-(3-Bromo-1H-indazol-5-yl)-4-[4-chloro-3-(methyloxy)phenyl]-2-methyl-6-oxo-1,4,5,6-tetrahydro-3-pyridinecarboxamide;

4-[4-Chloro-3-(methyloxy)phenyl]-2-methyl-N-(3-methyl-1H-indazol-5-yl)-6-oxo-1,4,5,6-tetrahydro-3-pyridinecarboxamide;

4-[4-Chloro-3-(methyloxy)phenyl]-N-(3-ethyl-1H-indazol-5-yl)-2-methyl-6-oxo-1,4,5,6-tetrahydro-3-pyridinecarboxamide;

4-[4-Chloro-3-(methyloxy)phenyl]-N-(6-fluoro-1H-indazol-5-yl)-2-methyl-6-oxo-1,4,5,6-tetrahydro-3-pyridinecarboxamide;

4-(4-Chloro-3-hydroxyphenyl)-N-(3-chloro-1H-indazol-5-yl)-2-methyl-6-oxo-1,4,5,6-tetrahydro-3-pyridinecarboxamide;

N-(3-Bromo-1H-indazol-5-yl)-4-(4-chloro-3-hydroxyphenyl)-2-methyl-6-oxo-1,4,5,6-tetrahydro-3-pyridinecarboxamide;

4-(4-Chloro-3-hydroxyphenyl)-2-methyl-N-(3-methyl-1H-indazol-5-yl)-6-oxo-1,4,5,6-tetrahydro-3-pyridinecarboxamide;

4-(4-Chloro-3-hydroxyphenyl)-N-(3-ethyl-1H-indazol-5-yl)-2-methyl-6-oxo-1,4,5,6-tetrahydro-3-pyridinecarboxamide;

4-(4-Chloro-3-hydroxyphenyl)-N-(6-fluoro-1H-indazol-5-yl)-2-methyl-6-oxo-1,4,5,6-tetrahydro-3-pyridinecarboxamide;

N-(3-Chloro-1H-indazol-5-yl)-4-(4-chlorophenyl)-1,2-dimethyl-6-oxo-1,4,5,6-tetrahydro-3-pyridinecarboxamide;

N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide;

1-Ethyl-N-(6-fluoro-1H-indazol-5-yl)-2-methyl-6-oxo-4-[4-(trifluoromethyl)phenyl]-1,4,5,6-tetrahydro-3-pyridinecarboxamide;

N-(6-Fluoro-1H-indazol-5-yl)-2-methyl-1-(2-methylpropyl)-6-oxo-4-[4-(trifluoromethyl)phenyl]-1,4,5,6-tetrahydro-3-pyridinecarboxamide; and 1-[2-(Dimethylamino)-2-oxoethyl]-N-(6-fluoro-1H-indazol-5-yl)-2-methyl-6-oxo-4-[4-(trifluoromethyl)phenyl]-1,4,5,6-tetrahydro-3-pyridinecarboxamide.

EXAMPLES

The following examples are intended to be illustrative only and not limiting in any way:

Example 1

N-1H-Indazol-5-yl-2-methyl-4-(2-naphthalenyl)-6-oxo-1,4,5,6-tetrahydro-3-pyridinecarboxamide

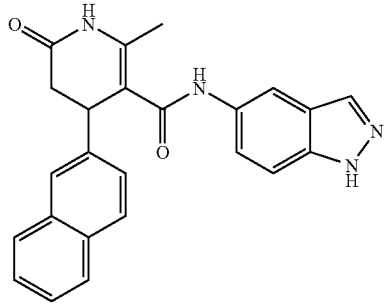

Step 1. Methyl 2-methyl-4-(2-naphthalenyl)-6-oxo-1,4,5,6-tetrahydro-3-pyridinecarboxylate 2-Naphthaldehyde (30.0 g, 192 mmol, 1.00 equiv), 2,2-dimethyl-1,3-dioxane-4,6-dione (27.6 g, 192 mmol, 1.00 equiv), methyl acetoacetate (20.7 mL, 192 mmol, 1.00 equiv), and ammonium acetate (15.6 g, 202 mmol, 1.05 equiv) were dissolved in acetic acid (0.20 L) and heated to reflux for 4 hours, then cooled to room temperature. Addition of water (1 L) to the cooled reaction mixture induced formation of a white precipitate. The solid was collected by filtration and triturated with diethyl ether to provide the 20.5 g (36%) of the product as an off-white solid. MS (ES+) m/e 296 [M+H]+.

Step 2. 2-Methyl-4-(2-naphthalenyl)-6-oxo-1,4,5,6-tetrahydro-3-pyridinecarboxylic acid The product from Step 1 (2.32 g, 7.9 mmol, 1.00 equiv) was dissolved in MeOH (32 mL). THF (10 mL) was added, followed by 2.5N NaOH (10 mL). The reaction mixture was heated to 60° C. for 6 hours, then stirred at room temperature for an additional 16 hours. The reaction mixture was diluted with water and extracted with ethyl acetate. The organic phase was washed again with 1N NaOH. The aqueous phases were combined and acidified to pH~1 with 5N HCl. The aqueous solution was extracted twice with ethyl acetate. The combined organic extracts were washed with satd. NaCl, dried over $Na_2SO_4$, and filtered. The filtrate was concentrated en vacuo and azeotroped several times with hexane. The resulting solid was triturated with 50% $CH_2Cl_2$/hexanes to afford 570 mg of the acid as an off-white solid. MS (ES+) m/e 282 [M+H]+.

Step 3. N-1H-Indazol-5-yl-2-methyl-4-(2-naphthalenyl)-6-oxo-1,4,5,6-tetrahydro-3-pyridinecarboxamide The product of step 2 (450 mg, 1.60 mmol, 1 equiv) was combined with 1H-indazol-5-amine (212 mg, 1.60 mmol, 1 equiv) and polystyrene-bound carbodiimide (1.78 g, 1.1 mmol/g, 1.97 mmol, 1.2 equiv) in 6 mL DMF. The reaction mixture was stirred for 22 hours at room temperature. The resin was removed by filtration and washed alternately with CH$_2$Cl$_2$ and MeOH, ending with CH$_2$Cl$_2$. The volatile solvents were removed en vacuo and water was added, providing a solid residue. The residue was triturated with ethyl acetate, affording 140 mg of the title compound as a white crystalline solid. MS (ES+) m/e 397 [M+H]$^+$ Example 2

4-(4-Fluorophenyl)-N-1H-indazol-5-yl-2-methyl-6-oxo-1,4,5,6-tetrahydro-3-pyridinecarboxamide

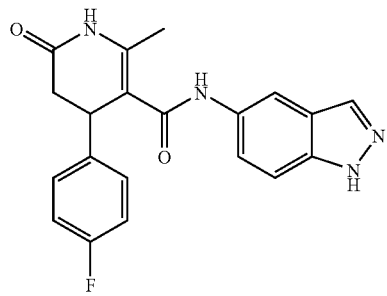

Step 1. Methyl 4-(4-fluorophenyl)-2-methyl-6-oxo-1,4,5,6-tetrahydro-3-pyridinecarboxylate 4-Fluorobenzaldehyde (0.997 mL, 9.30 mmol, 1.00 equiv), 2,2-dimethyl-1,3-dioxane-4,6-dione (1.34 g, 9.30 mmol, 1.00 equiv), methyl acetoacetate (1.00 mL, 9.30 mmol, 1.00 equiv), and ammonium acetate (0.752 g, 9.77 mmol, 1.05 equiv) were dissolved in acetic acid (10 mL) and heated to reflux for 3.5 hours. The reaction mixture was diluted with EtOAc and water, and neutralized with 2N NaOH. The phases were separated, and the organic phase was washed with satd. NaHCO$_3$, then NaCl. The organic phase was dried over Na$_2$SO$_4$, filtered and concentrated to a yellow residue. Recrystallization (CH$_2$Cl$_2$/hexanes) provided 480 mg (20%) of the product as a pale yellow solid. MS (ES+) m/e 264 [M+H]$^+$.

Step 2. 4-(4-Fluorophenyl)-2-methyl-6-oxo-1,4,5,6-tetrahydro-3-pyridinecarboxylic acid The product from Step 1 (0.200 g, 0.76 mmol, 1.00 equiv) was dissolved in MeOH (3 mL). Following addition of 2.5N NaOH (1 mL), the reaction mixture was heated to 60° C. for 6 hours, then stirred at room temperature for an additional 16 hours. The reaction mixture was diluted with water and extracted with ethyl acetate. The organic phase was washed again with 1N NaOH. The aqueous phases were combined and acidified to pH~1 with 5N HCl, and extracted twice with ethyl acetate. The combined organic extracts were washed with satd NaCl, dried over Na$_2$SO$_4$, and filtered. The filtrate was concentrated en vacuo and azeotroped several times with hexanes to afford 128 mg (67%) of the acid as an off-white solid. MS (ES+) m/e 250 [M+H]$^+$.

Step 3. 4-(4-Fluorophenyl)-N-1H-indazol-5-yl-2-methyl-6-oxo-1,4,5,6-tetrahydro-3-pyridinecarboxamide The product of step 2 (128 mg, 0.514 mmol, 1.00 equiv), 1H-indazol-5-amine (82.0 mg, 0.617 mmol, 1.20 equiv), EDC (118 mg, 0.617 mmol, 1.20 equiv), and DMAP (10 mg, catalytic) were suspended in 2.0 mL DMF. Et$_3$N (0.086 mL, 1.35 mmol, 2.4 equiv) was added and the solution was heated to 80° C. for 2 hours. The reaction mixture was cooled to room temperature and diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (100% EtOAc) to provide 25.0 mg (13%) of the title compound as a white solid. MS (ES+) m/e 365 [M+H]$^+$ Example 3

4-(4-Chloro-2-fluorophenyl)-N-1H-indazol-5-yl-2-methyl-6-oxo-1,4,5,6-tetrahydro-3-pyridinecarboxamide

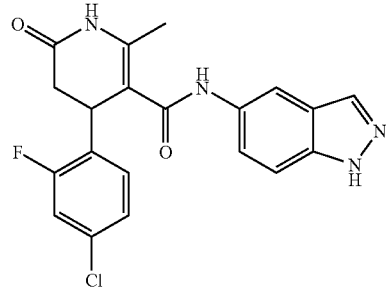

Step 1. Methyl 4-(4-chloro-2-fluorophenyl)-2-methyl-6-oxo-1,4,5,6-tetrahydro-3-pyridinecarboxylate 4-Chloro-2-fluorobenzaldehyde (1.00 g, 6.30 mmol, 1.00 equiv), 2,2-dimethyl-1,3-dioxane-4,6-dione (907 mg, 6.30 mmol, 1.00 equiv), methyl acetoacetate (0.679 mL, 6.30 mmol, 1.00 equiv), and ammonium acetate (0.512 g, 6.60 mmol, 1.05 equiv) were dissolved in acetic acid (7.0 mL) and heated to reflux for 2 hours. The reaction mixture was cooled to room temperature, neutralized with solid K$_2$CO$_3$, and diluted with EtOAc and water. The phases were separated, and the organic phase was washed with satd. NaCl. The organic phase was dried over Na$_2$SO$_4$, filtered and concentrated to a yellow residue. Recrystallization (CH$_2$Cl$_2$/hexanes) provided 503 mg (27%) of the product as a pale yellow solid. MS (ES+) m/e 298 [M+H]$^+$.

Step 2. 4-(4-Chloro-2-fluorophenyl)-2-methyl-6-oxo-1,4,5,6-tetrahydro-3-pyridinecarboxylic acid The product from Step 1 (503 mg, 1.70 mmol, 1.00 equiv) was dissolved in 3/1 MeOH:THF (8 mL total). Following addition of 2.5N NaOH (2 mL), the reaction mixture was heated to 60° C. for 6 hours, then stirred at room temperature for an additional 16 hours. The reaction mixture was diluted with water and extracted with ethyl acetate. The organic phase was washed again with 1N NaOH. The aqueous phases were combined and acidified to pH~1 with 5N HCl, and extracted twice with ethyl acetate. The combined organic extracts were washed with satd. NaCl, dried over Na$_2$SO$_4$, and filtered. The filtrate was concentrated en vacuo and azeotroped several times with hexanes to afford 252 mg (52%) of the acid as an off-white solid. MS (ES+) m/e 284 [M+H]$^+$.

Step 3. 4-(4-Chloro-2-fluorophenyl)-N-1H-indazol-5-yl-2-methyl-6-oxo-1,4,5,6-tetrahydro-3-pyridinecarboxamide The product of step 2 (252 mg, 0.890 mmol, 1.00 equiv), 1H-indazol-5-amine (142 mg, 1.07 mmol, 1.20 equiv), EDC (229 mg, 1.07 mmol, 1.20 equiv), and DMAP (10 mg, catalytic) were suspended in 4.0 mL DMF. Et$_3$N (0.298 mL, 2.14 mmol, 1.00 equiv) was added and the solution was heated to 80° C. for 2 hours. The reaction mixture was cooled to room temperature and diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (100% EtOAc) to provide 0.100 g (28%) of the title compound as a white solid. MS (ES+) m/e 399 [M+H]$^+$

Example 4

4-(4-Chlorophenyl)-N-1H-indazol-5-yl-2-methyl-6-oxo-1,4,5,6-tetrahydro-3-pyridinecarboxamide

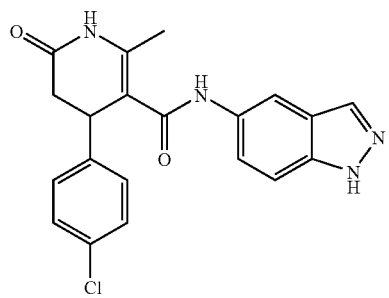

Step 1. Methyl 4-(4-chlorophenyl)-2-methyl-6-oxo-1,4,5,6-tetrahydro-3-pyridinecarboxylate 4-Chlorobenzaldehyde (1.30 g, 9.30 mmol, 1.00 equiv), 2,2-dimethyl-1,3-dioxane-4,6-dione (1.34 g, 9.30 mmol, 1.00 equiv), methyl acetoacetate (1.00 mL, 9.30 mmol, 1.00 equiv), and ammonium acetate (0.752 g, 9.77 mmol, 1.05 equiv) were dissolved in acetic acid (10 mL) and heated to reflux for 2 hours. The reaction mixture was cooled to room temperature, neutralized with solid K$_2$CO$_3$, and diluted with EtOAc and water. The phases were separated, and the organic phase was washed with satd. NaCl. The organic phase was dried over Na$_2$SO$_4$, filtered and concentrated en vacuo to a yellow residue. Recrystallization (CH$_2$Cl$_2$/hexanes) provided 735 mg (28%) of the product as a pale yellow solid. MS (ES+) m/e 280 [M+H]$^+$.

Step 2. 4-(4-Chlorophenyl)-2-methyl-6-oxo-1,4,5,6-tetrahydro-3-pyridinecarboxylic acid The product from Step 1 (735 mg, 2.63 mmol, 1.00 equiv) was dissolved in 3/1 MeOH:THF (12 mL total). Following addition of 2.5N NaOH (3 mL), the reaction mixture was heated to 60° C. for 6 hours, then stirred at room temperature for an additional 16 hours. The reaction mixture was diluted with water and extracted with ethyl acetate. The organic phase was washed again with 1N NaOH. The aqueous phases were combined and acidified to pH~1 with 5N HCl, and extracted twice with ethyl acetate. The combined organic extracts were washed with satd. NaCl, dried over Na$_2$SO$_4$, and filtered. The filtrate was concentrated en vacuo and azeotroped several times with hexanes to afford 494 mg (71%) of the acid as an off-white solid. MS (ES+) m/e 266 [M+H]$^+$.

Step 3. 4-(4-Chlorophenyl)-N-1H-indazol-5-yl-2-methyl-6-oxo-1,4,5,6-tetrahydro-3-pyridinecarboxamide The product of step 2 (494 mg, 1.86 mmol, 1.00 equiv), 1H-indazol-5-amine (296 mg, 2.23 mmol, 1.20 equiv), EDC (426 mg, 2.23 mmol, 1.20 equiv), and DMAP (10 mg, catalytic) were suspended in 8.0 mL DMF. Et$_3$N (0.621 mL, 4.46 mmol, 1.00 equiv) was added and the solution was heated to 80° C. for 2 hours. The reaction mixture was cooled to room temperature and diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (100% EtOAc) to provide 0.120 g (17%) of the title compound as a white solid. MS (ES+) m/e 399 [M+H]$^+$

Example 5

N-1H-Indazol-5-yl-2-methyl-6-oxo-4-[4-(trifluoromethyl)phenyl]-1,4,5,6-tetrahydro-3-pyridinecarboxamide

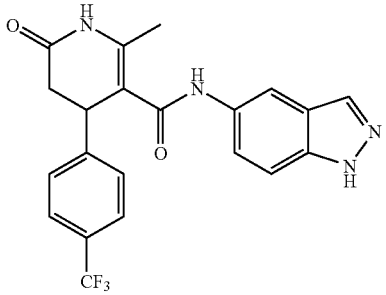

Step 1. Methyl 4-[4-(trifluoromethyl)phenyl]-2-methyl-6-oxo-1,4,5,6-tetrahydro-3-pyridinecarboxylate 4-Trifluoromethylbenzaldehyde (25.0 mL, 147 mmol, 1.00 equiv), 2,2-dimethyl-1,3-dioxane-4,6-dione (21.2 g, 147 mmol, 1.00 equiv), methyl acetoacetate (15.8 mL, 147 mmol, 1.00 equiv), and ammonium acetate (11.8 g, 154 mmol, 1.05 equiv) were dissolved in acetic acid (150 mL) and heated to reflux for 2 hours. Addition of water to the stirred reaction mixture induced precipitation of a solid residue. The solid was recovered by filtration and triturated with 50% CH$_2$Cl$_2$/hexane to afford 8.50 g (19%) of the product as a white solid. MS (ES+) m/e 300 [M+H]$^+$.

Step 2. 4-[4-(Trifluoromethyl)phenyl]-2-methyl-6-oxo-1,4,5,6-tetrahydro-3-pyridinecarboxylic acid The product from Step 1 (1.00 g, 3.34 mmol, 1.00 equiv) was dissolved in MeOH (11 mL). Following addition of 2.5N NaOH (4 mL), the reaction mixture was heated to reflux for 8 hours. The reaction mixture was diluted with water and extracted with ethyl acetate. The organic phase was washed again with 1N NaOH. The aqueous phases were combined and acidified to pH~1 with 5N HCl, and extracted twice with ethyl acetate. The combined organic extracts were washed with satd. NaCl, dried over Na$_2$SO$_4$, and filtered. The filtrate was concentrated en vacuo and azeotroped several times with hexanes. The resulting white solid was triturated with Et$_2$O to afford 146 mg (15%) of the acid as an off-white solid. MS (ES+) m/e 266 [M+H]$^+$.

Step 3. N-1H-Indazol-5-yl-2-methyl-6-oxo-4-[4-(trifluoromethyl)phenyl]-1,4,5,6-tetrahydro-3-pyridinecarboxamide The product of step 2 (146 mg, 0.512 mmol, 1.00 equiv), 1H-indazol-5-amine (68 mg, 0.512 mmol, 1.00 equiv) and EDC (118 mg, 0.615 mmol, 1.20 equiv) were suspended in 8.0 mL DMF. Et$_3$N (0.086 mL, 0.615 mmol, 1.20 equiv) was added and the solution was stirred overnight at room temperature. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (100% EtOAc) to provide 0.070 g (33%) of the title compound as a white solid. MS (ES+) m/e 415 [M+H]$^+$ Example 6

4-(4-Biphenylyl)-N-1H-indazol-5-yl-2-methyl-6-oxo-1,4,5,6-tetrahydro-3-pyridinecarboxamide

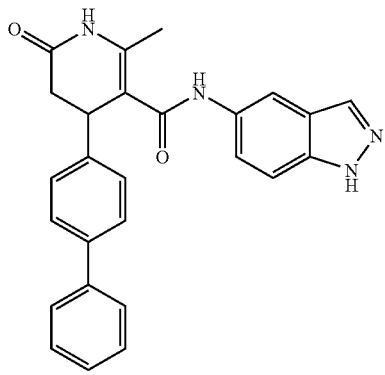

Step 1. N-1H-Indazol-5-yl-3-oxobutanamide

In a round-bottomed flask 1H-indazol-5-amine (500 mg, 3.75 mmol, 1 equiv) was suspended in acetonitrile (1 mL). In a separate flask, diketene (stabilized w/copper sulfate, 0.289 mL, 3.75 mmol, 1 equiv) was dissolved in acetonitrile. The diketene solution was added to the amine suspension in four portions. The reaction was sealed and heated to 50° C. for 14 h. The mixture was diluted with diethyl ether (approx. 2 mL) and the solid product was collected by filtration and washed several times with diethyl ether. The ketoamide was isolated as a pale brown powder (761 mg, 94%). MS m/e 218 [M+H]$^+$.

Step 2. 4-(4-Biphenylyl)-N-1H-indazol-5-yl-2-methyl-6-oxo-1,4,5,6-tetrahydro-3-pyridinecarboxamide The product of Step 1 (0.500 g, 2.30 mmol, 1.00 equiv), 4-biphenylcarboxaldehyde (420 ring, 2.30 mmol, 1.00 equiv), 2,2-dimethyl-1,3-dioxane-4,6-dione (331 mg, 2.3 mmol, 1.00 equiv), and ammonium acetate (186 mg, 2.42 mmol, 1.05 equiv) were dissolved in acetic acid (2.3 mL) and heated to reflux for 2 hours. Addition of water to the stirred reaction mixture induced precipitation of a solid residue. The solid was recovered by filtration and the residue was partitioned between EtOAc and satd. NaHCO$_3$. The phases were separated and the organic layer was washed with satd. NaCl, dried over Na$_2$SO$_4$, filtered and concentrated en vacuo. The residue was purified by reverse phase HPLC (Xterra Prep 30×100, 25 mL/min, 30-70% 5 mM aq. NH$_4$HCO$_3$/CH$_3$CN over 10 minutes) to provide 5 mg of a white solid. MS (ES+) m/e 423 [M+H]$^+$.

Example 7

4-(3,4-Dichlorophenyl)-N-1H-indazol-5-yl-2-methyl-6-oxo-1,4,5,6-tetrahydro-3-pyridinecarboxamide

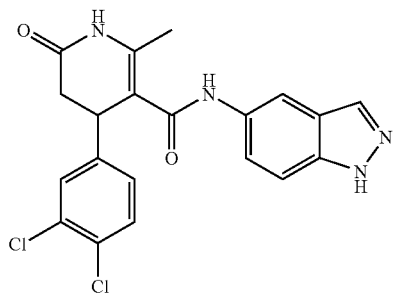

The product of Example 6, Step 1 (0.100 g, 0.460 mmol, 1.00 equiv), 3,4-dichlorobenzaldehyde (80.5 mg, 0.460 mmol, 1.00 equiv), 2,2-dimethyl-1,3-dioxane-4,6-dione (66.0 mg, 0.460 mmol, 1.00 equiv), and ammonium acetate (37.0 mg, 0.484 mmol, 1.05 equiv) were dissolved in acetic acid (0.5 mL) and heated to reflux for 2 hours. The reaction mixture was partitioned between EtOAc and water. The phases were separated and the organic phase was washed with satd. NaHCO$_3$, satd. NaCl, dried over Na$_2$SO$_4$, filtered and concentrated en vacuo. Preliminary purification by flash chromatography (100% EtOAc) was followed by reverse phase HPLC purification (Xterra Prep 30×100, 25 mL/min, 10-90% 5 mM aq. NH$_4$HCO$_3$/CH$_3$CN over 10 minutes) to provide 40 mg of a white solid. MS (ES+) m/e 416 [M+H]$^+$.

Example 8

4-[2-Fluoro-4-(trifluoromethyl)phenyl]-N-1H-indazol-5-yl-2-methyl-6-oxo-1,4,5,6-tetrahydro-3-pyridinecarboxamide

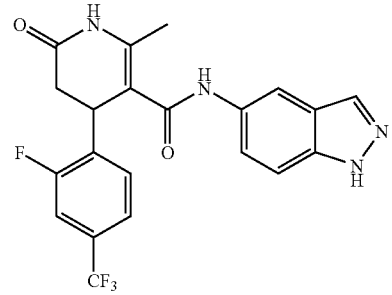

The product of Example 6, Step 1 (0.206 g, 0.949 mmol, 1.00 equiv), 2-fluoro-4-trifluoromethylbenzaldehyde (0.130 ml, 0.949 mmol, 1.00 equiv), 2,2-dimethyl-1,3-dioxane-4,6-dione (137 mg, 0.949 mmol, 1.00 equiv), and ammonium acetate (78.0 mg, 0.997 mmol, 1.05 equiv) were dissolved in acetic acid (1.0 mL). The reaction mixture was heated to 80° for 1.5 hours, then 120° C. for 2 hours, and cooled to room temperature overnight. Addition of water to the reaction mixture induced formation of a precipitate. The precipitate was collected by filtration and washed with diethyl ether affording 133 mg (32%) of the title compound as a pale grey solid. MS (ES+) m/e 433 [M+H]+.

Example 9

N-1H-Indazol-5-yl-2-methyl-6-oxo-4-(3-quinolinyl)-1,4,5,6-tetrahydro-3-pyridinecarboxamide

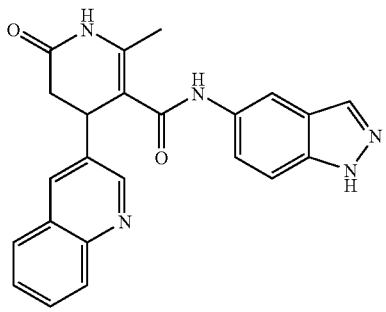

The product of Example 6, Step 1 (0.217 g, 1.38 mmol, 1.00 equiv), 3-quinolinecarboxaldehyde (0.300 g, 1.38 mmol, 1.00 equiv), 2,2-dimethyl-1,3-dioxane-4,6-dione (199 mg, 1.38 mmol, 1.00 equiv), and ammonium acetate (112 mg, 1.38 mmol, 1.05 equiv) were dissolved in acetic acid (1.4 mL). The reaction mixture was heated to 80° for 1.5 hours, then 120° C. for 2 hours, and cooled to room temperature overnight. The reaction mixture was diluted with EtOAc and water, then neutralized with solid NaHCO$_3$. The phases were separated and the organic phase was dried over Na$_2$SO$_4$, filtered and concentrated en vacuo. Trituration of the resulting solid with EtOAc afforded 39 mg (7%) of the title compound as a pale grey solid. MS (ES+) m/e 398 [M+H]+.

Example 10

4-(4-Fluorophenyl)-N-1H-indazol-5-yl-1,2-dimethyl-6-oxo-1,4,5,6-tetrahydro-3-pyridinecarboxamide

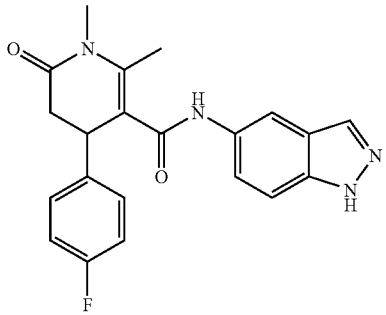

Step 1. Methyl 4-(4-fluorophenyl)-1,2-dimethyl-6-oxo-1,4,5,6-tetrahydro-3-pyridinecarboxylate The product from Example 2, Step 1 (1.5 g, 5.70 mmol, 1 equiv) and iodomethane (809 mg, 5.70 mmol, 1 equiv) were dissolved in DMF (20 mL) and cooled to 0° C. To this was added portionwise sodium hydride 60% in mineral oil (228 mg, 5.70 mmol, 1 equiv) and warmed to room temperature over 1 h. The reaction was quenched with water, and extracted with EtOAc. The organic phase was concentrated in vacuo. The product was obtained as a light yellow oil (1.58 g, quant.). MS (ES+) m/e 278 [M+H]+.

Step 2. 4-(4-Fluorophenyl)-N-1H-indazol-5-yl-1,2-dimethyl-6-oxo-1,4,5,6-tetrahydro-3-pyridinecarboxamide The product of Step 1 (1.58 g, 5.70 mmol, 1 equiv) was dissolved in methanol (24 mL) and 2.5 N NaOH (8 mL) was added. The reaction was heated to 60° C. for 3 h. Upon cooling, the resulting mixture was partitioned between EtOAc and water. The aqueous layer was acidified to pH 1 and extracted with EtOAc. The phases were separated and the organic phase was concentrated in vacuo. The resulting residue (1.50 g, 5.70 mmol, 1.1 equiv) was dissolved in DMF (30 mL). 1H-indazol-5-amine (700 mg, 5.18 mmol, 1.0 equiv) and PS-carbodiimide resin (8.27 g, 7.77 mmol, 1.5 equiv) were added and the mixture stirred overnight at room temperature. The resin was removed by filtration and washed alternately with methanol and CH$_2$Cl$_2$, followed by diethyl ether. The filtrate was concentrated en vacuo to remove the volatile solvents. The residue was dissolved in EtOAc, washed twice with water and once with satd. NaHCO$_3$. The organic phase was concentrated in vacuo and the residue was purified by reverse phase HPLC (Xterra Prep 19×50, 25 mL/min, 10-90% 5 mM aq. NH$_4$HCO$_3$/CH$_3$CN over 9 minutes) to provide 8 mg (0.4%) of a white crystalline solid. MS (ES+) m/e 379 [M+H]+.

Example 11

N-(3-Chloro-1H-indazol-5-yl)-2-methyl-6-oxo-4-[4-(trifluoromethyl)phenyl]-1,4,5,6-tetrahydro-3-pyridinecarboxamide

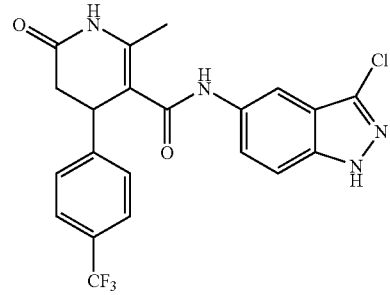

The product of Example 5, Step 2 (0.100 g, 0.330 mmol, 1.00 equiv), 3-chloro-1H-indazol-5-amine (84 mg, 0.502 mmol, 1.50 equiv) and PS-carbodiimide resin (456 mg, 0.502 mmol, 1.00 equiv) were suspended in 2.0 mL DMF and stirred overnight at room temperature. The reaction mixture was concentrated to approximately 1 mL DMF and water was added. The resulting precipitate was collected by filtration and washed with 50% CH$_2$Cl$_2$/hexanes. The product was purified by preparative reverse phase HPLC (19×50 Xterra Prep RP 10-90% CH$_3$CN/5 mM NH$_4$HCO$_3$ over 9 min, 25 ml/min) to provide 5.0 mg (3%) of the title compound as a white solid. MS (ES+) m/e 449 [M+H]$^+$.

Example 12

N-(3-Chloro-1H-indazol-5-yl)-4-(4-fluorophenyl)-2-methyl-6-oxo-1,4,5,6-tetrahydro-3-pyridinecarboxamide

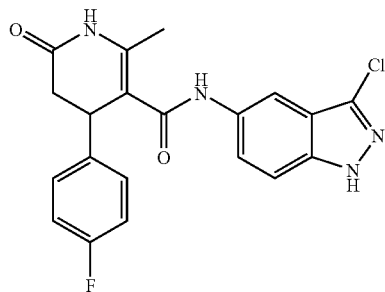

The product from Example 2, Step 2 (170 mg, 0.68 mmol, 1.0 equiv) was combined with 3-chloro-1H-indazol-5-amine (172 mg, 1.02 mmol, 1.5 equiv) and PS-carbodiimide resin (0.994 mmol/g loading, 1.085 g, 1.02 mmol, 1.5 equiv) in 10 mL of DMF and reacted overnight at room temperature. The reaction mixture was filtered and washed alternately with MeOH and CH$_2$Cl$_2$ (twice), then with diethyl ether. The filtrate was concentrated en vacuo and redissolved in ethyl acetate. The solution was washed with 0.5 N HCl, 0.5 N NaOH, and satd. NaCl. The organic layer was concentrated en vacuo. Purification by flash chromatography (0-50% EtOAc in CH$_2$Cl$_2$) followed by trituration with CH$_2$Cl$_2$ provided 45 mg (16.5%) of the title compound as light pink crystals. MS (ES+) m/e 399 [M+H]$^+$.

Example 13

N-(3-Chloro-1H-indazol-5-yl)-2-methyl-4-(2-naphthalenyl)-6-oxo-1,4,5,6-tetrahydro-3-pyridinecarboxamide

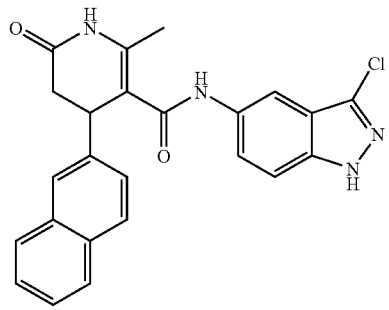

The product from Example 1, Step 2 (100 mg, 0.36 mmol, 1.0 equiv) was combined with 3-chloro-1H-indazol-5-amine (90 mg, 0.53 mmol, 1.5 equiv) and PS-carbodiimide resin (0.994 mmol/g loading, 564 mg, 0.53 mmol, 1.5 equiv) in 5 mL of DMF and reacted overnight at room temperature. The reaction mixture was filtered and washed alternately with MeOH and CH$_2$Cl$_2$ (twice), then with diethyl ether. The filtrate was concentrated en vacuo and redissolved in ethyl acetate. The solution was washed with 0.5 N HCl, 0.5 N NaOH, and satd. NaCl. The organic layer was concentrated en vacuo. The residue was triturated with methylene chloride/methanol/ethyl acetate to provide 20 mg (13%) of the title compound as a light pink powder. MS (ES+) m/e 431 [M+H]$^+$.

Example 14

4-(4-Chloro-2-fluorophenyl)-N-(3-chloro-1H-indazol-5-yl)-2-methyl-6-oxo-1,4,5,6-tetrahydro-3-pyridinecarboxamide

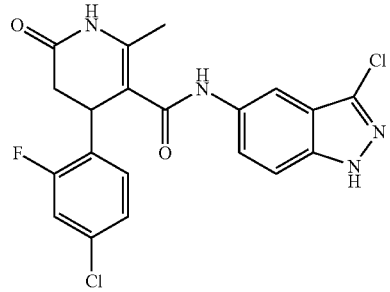

The product from Example 3, Step 2 (103 mg, 0.36 mmol, 1.0 equiv) was combined with 3-chloro-1H-indazol-5-amine (91 mg, 0.54 mmol, 1.5 equiv) and PS-carbodiimide resin (0.994 mmol/g loading, 580 mg, 0.54 mmol, 1.5 equiv) in 6 mL of DMF and reacted overnight at room temperature. The reaction mixture was filtered and washed alternately with MeOH and CH$_2$Cl$_2$ (twice), then with diethyl ether. The filtrate was concentrated en vacuo and redissolved in EtOAc. The solution was washed with 0.5 N HCl, 0.5 N NaOH and satd. NaCl. The organic layer was concentrated en vacuo. Following purification by flash chromatography (0-50% EtOAc in CH$_2$Cl$_2$), the solid was triturated with CH$_2$Cl$_2$ to provide 10 mg (6.5%) of the title compound as light pink crystals. MS (ES+) m/e 434 [M+H]$^+$.

Example 15

2-Methyl-N-(3-methyl-1H-indazol-5-yl)-6-oxo-4-[4-(trifluoromethyl)phenyl]-1,4,5,6-tetrahydro-3-pyridinecarboxamide

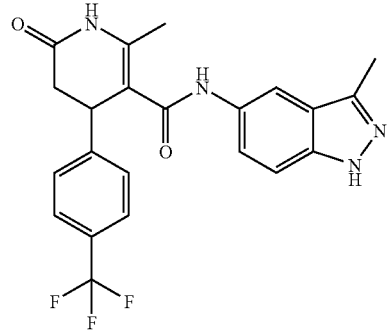

The product of Example 5, Step 2 (225 mg, 0.75 mmol, 1.00 equiv), 5-amino-3-methylindazole (110 mg, 0.75 mmol, 1.0 equiv), and EDC (172 mg, 0.90 mmol, 1.20 equiv) were suspended in 2.0 mL DMF. Et$_3$N (0.125 mL, 0.90 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) and further purified by reverse-phase HPLC (10-70% CH$_3$CN/H$_2$O—NH$_4$OH to pH 10 over 20 minutes, retention time 11.74 min) to provide 18 mg (6%) of the title compound as a white solid. MS (ES+) m/e 429 [M+H]$^+$

Example 16

N-(3-Bromo-1H-indazol-5-yl)-2-methyl-6-oxo-4-[4-(trifluoromethyl)phenyl]-1,4,5,6-tetrahydro-3-pyridinecarboxamide

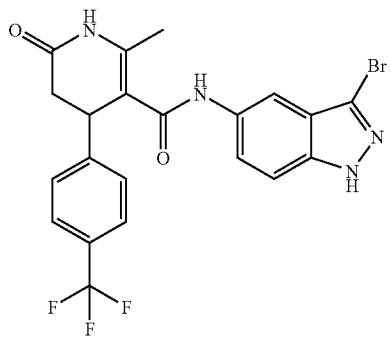

The product of Example 5, Step 2 (110 mg, 0.368 mmol, 1.00 equiv), 5-amino-3-bromoindazole (78 mg, 0.368 mmol, 1.0 equiv), and EDC (84 mg, 0.441 mmol, 1.20 equiv) were suspended in 1.0 mL DMF. Et$_3$N (0.061 mL, 0.441 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered and concentrated en vacuo. The residue was purified by flash chromatography (20-100% EtOAc in Hexanes) to provide 52 mg (29%) of the title compound as an off white solid. MS (ES+) m/e 494 [M+H]$^+$

Example 17

N-(3-Ethyl-1H-indazol-5-yl)-2-methyl-6-oxo-4-[4-(trifluoromethyl)phenyl]-1,4,5,6-tetrahydro-3-pyridinecarboxamide

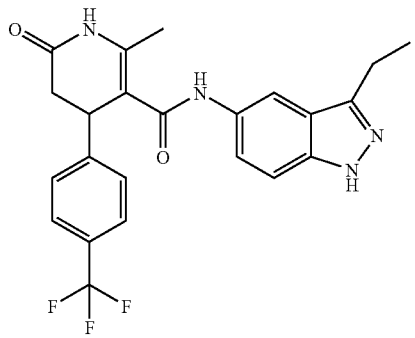

The product of Example 5, Step 2 (125 mg, 0.418 mmol, 1.00 equiv), 5-amino-3-ethylindazole (67 mg, 0.418 mmol, 1.0 equiv), and EDC (96 mg, 0.501 mmol, 1.20 equiv) were suspended in 1.25 mL DMF. Et$_3$N (0.070 mL, 0.501 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was triturated with EtOAc and CH$_2$Cl$_2$, filtered, and washed with CH$_2$Cl$_2$ to provide 32 mg (17%) of the title compound as an off white solid. MS (ES+) m/e 443 [M+H]$^+$

Example 18

N-(6-Fluoro-1H-indazol-5-yl)-2-methyl-6-oxo-4-[4-(trifluoromethyl)phenyl]-1,4,5,6-tetrahydro-3-pyridinecarboxamide

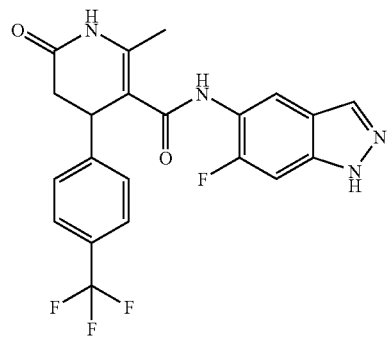

The product of Example 5, Step 2 (200 mg, 0.67 mmol, 1.00 equiv), 5-amino-6-fluoroindazole (101 mg, 0.67 mmol, 1.0 equiv), and EDC (153 mg, 0.80 mmol, 1.20 equiv) were suspended in 2.0 mL DMF. Et$_3$N (0.112 mL, 0.80 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 65 mg (22%) of the title compound as an off white solid. MS (ES+) m/e 433 [M+H]$^+$

Example 19

N-(7-Chloro-1H-indazol-5-yl)-2-methyl-6-oxo-4-[4-(trifluoromethyl)phenyl]-1,4,5,6-tetrahydro-3-pyridinecarboxamide

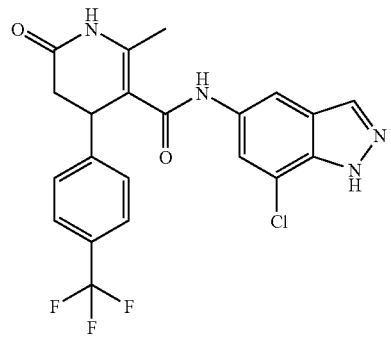

The product of Example 5, Step 2 (250 mg, 0.835 mmol, 1.00 equiv), 5-amino-7-chloroindazole (140 mg, 0.835 mmol, 1.0 equiv), and EDC (191 mg, 1.00 mmol, 1.20 equiv) were suspended in 2.0 mL DMF. Et$_3$N (0.140 mL, 1.00 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (20-100% EtOAc in Hexanes) and further purified by reverse-phase HPLC (10-80% CH₃CN/H₂O—NH₄OH to pH 10 over 17 minutes, retention time 11.67 min) to provide 45 mg (12%) of the title compound as a white solid. MS (ES+) m/e 449 [M+H]⁺

Example 20

2-Methyl-N-(7-methyl-1H-indazol-5-yl)-6-oxo-4-[4-(trifluoromethyl)phenyl]-1,4,5,6-tetrahydro-3-pyridinecarboxamide

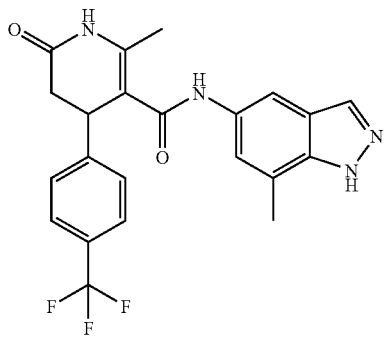

The product of Example 5, Step 2 (160 mg, 0.535 mmol, 1.00 equiv), 5-amino-7-methylindazole (79 mg, 0.535 mmol, 1.0 equiv), and EDC (123 mg, 0.642 mmol, 1.20 equiv) were suspended in 1.5 mL DMF. Et₃N (0.089 mL, 0.642 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was triturated with EtOAc and CH₂Cl₂, filtered, and washed with CH₂Cl₂ to provide 82 mg (36%) of the title compound as an off white solid. MS (ES+) m/e 429 [M+H]⁺

Example 21

N-(3-Chloro-1H-indazol-5-yl)-4-[2-fluoro-4-(trifluoromethyl)phenyl]-2-methyl-6-oxo-1,4,5,6-tetrahydro-3-pyridinecarboxamide

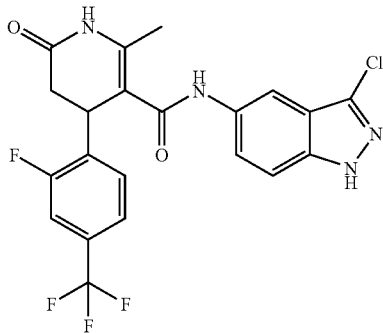

Step 1. Methyl 4-[2-fluoro-4-(trifluoromethyl)phenyl]-2-methyl-6-oxo-1,4,5,6-tetrahydro-3-pyridinecarboxylate The title compound was synthesized using the procedure stated in Example 1, Step 1 except that 2-fluoro-4-trifluoromethyl benzaldehyde was used to yield product as an off white solid. MS (ES+) m/e 332 [M+H]⁺

Step 2. 4-[2-Fluoro-4-(trifluoromethyl)phenyl]-2-methyl-6-oxo-1,4,5,6-tetrahydro-3-pyridinecarboxylic acid The title compound was synthesized using the procedure stated in Example 1, Step 2 except that the product from Step 1 was used and THF was not used to yield product as an off white solid. MS (ES+) m/e 318 [M+H]⁺

Step 3. N-(3-Chloro-1H-indazol-5-yl)-4-[2-fluoro-4-(trifluoromethyl)phenyl]-2-methyl-6-oxo-1,4,5,6-tetrahydro-3-pyridinecarboxamide The product of Step 2 (200 mg, 0.63 mmol, 1.00 equiv), 5-amino-3-chloroindazole (106 mg, 0.63 mmol, 1.0 equiv), and EDC (145 mg, 0.757 mmol, 1.20 equiv) were suspended in 1.75 mL DMF. Et₃N (0.106 mL, 0.757 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (20-100% EtOAc in Hexanes) and further purified by reverse-phase HPLC (10-80% CH₃CN/H₂O—NH₄OH to pH 10 over 17 minutes, retention time 12.41 min) to provide 60 mg (20%) of the title compound as a white solid. MS (ES+) m/e 467 [M+H]⁺

Example 22

N-(3-Bromo-1H-indazol-5-yl)-4-[2-fluoro-4-(trifluoromethyl)phenyl]-2-methyl-6-oxo-1,4,5,6-tetrahydro-3-pyridinecarboxamide

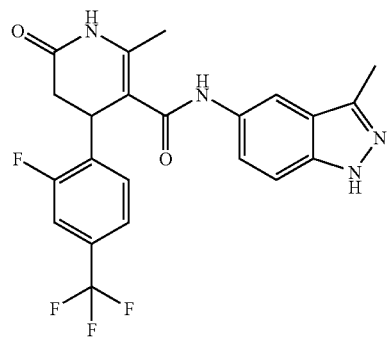

The product of Example 21, Step 2 (200 mg, 0.63 mmol, 1.00 equiv), 5-amino-3-bromoindazole (134 mg, 0.63 mmol, 1.0 equiv), and EDC (145 mg, 0.757 mmol, 1.20 equiv) were suspended in 1.75 mL DMF. Et₃N (0.106 mL, 0.757 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na$_2$SO$_4$, filtered, and concentrated en vacuo. The residue was purified by flash chromatography (20-100% EtOAc in Hexanes) and further purified by reverse-phase HPLC (10-80% CH$_3$CN/H$_2$O—NH$_4$OH to pH 10 over 17 minutes, retention time 12.59 min) to provide 65 mg (20%) of the title compound as a white solid. MS (ES+) m/e 511 [M+H]$^+$ Example 23

4-[2-Fluoro-4-(trifluoromethyl)phenyl]-2-methyl-N-(3-methyl-1H-indazol-5-yl)-6-oxo-1,4,5,6-tetrahydro-3-pyridinecarboxamide

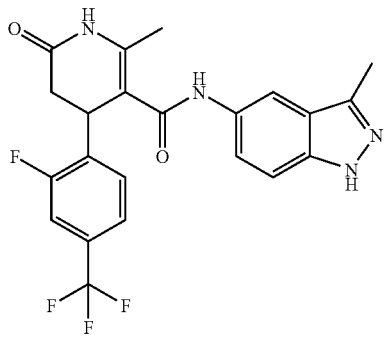

The product of Example 21, Step 2 (200 mg, 0.63 mmol, 1.00 equiv), 5-amino-3-methylindazole (93 mg, 0.63 mmol, 1.0 equiv), and EDC (145 mg, 0.757 mmol, 1.20 equiv) were suspended in 1.75 mL DMF. Et$_3$N (0.106 mL, 0.757 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 65 mg (23%) of the title compound as an off white solid. MS (ES+) m/e 447 [M+H]$^+$ Example 24

N-(3-Ethyl-1H-indazol-5-yl)-4-[2-fluoro-4-(trifluoromethyl)phenyl]-2-methyl-6-oxo-1,4,5,6-tetrahydro-3-pyridinecarboxamide

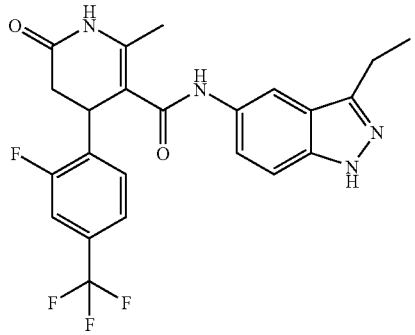

The product of Example 21, Step 2 (50 mg, 0.158 mmol, 1.00 equiv), 5-amino-3-ethylindazole (25 mg, 0.158 mmol, 1.0 equiv), and EDC (36 mg, 0.189 mmol, 1.20 equiv) were suspended in 0.5 mL DMF. Et$_3$N (0.026 mL, 0.189 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 25 mg (34%) of the title compound as an off white solid. MS (ES+) m/e 461 [M+H]$^+$ Example 25

N-(6-Fluoro-1H-indazol-5-yl)-4-[2-fluoro-4-(trifluoromethyl)phenyl]-2-methyl-6-oxo-1,4,5,6-tetrahydro-3-pyridinecarboxamide

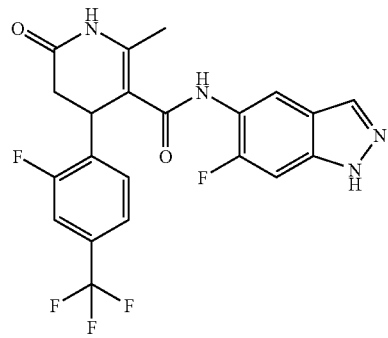

The product of Example 21, Step 2 (245 mg, 0.772 mmol, 1.00 equiv), 5-amino-6-fluoroindazole (117 mg, 0.772 mmol, 1.0 equiv), and EDC (177 mg, 0.927 mmol, 1.20 equiv) were suspended in 2.0 mL DMF. Et$_3$N (0.129 mL, 0.927 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 141 mg (41%) of the title compound as an off white solid. MS (ES+) m/e 451 [M+H]$^+$ Example 26

4-[2-Fluoro-4-(trifluoromethyl)phenyl]-2-methyl-N-(7-methyl-1H-indazol-5-yl)-6-oxo-1,4,5,6-tetrahydro-3-pyridinecarboxamide

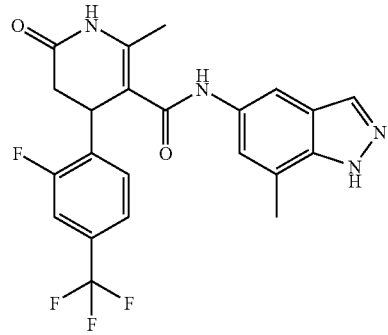

The product of Example 21, Step 2 (165 mg, 0.52 mmol, 1.00 equiv), 5-amino-7-methylindazole (77 mg, 0.52 mmol, 1.0 equiv), and EDC (119 mg, 0.624 mmol, 1.20 equiv) were suspended in 1.5 mL DMF. Et$_3$N (0.087 mL, 0.624 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (20-100% EtOAc in Hexanes) to provide 77 mg (33%) of the title compound as an off white solid. MS (ES+) m/e 447 [M+H]⁺

Example 27

N-(7-Chloro-1H-indazol-5-yl)-4-[2-fluoro-4-(trifluoromethyl)phenyl]-2-methyl-6-oxo-1,4,5,6-tetrahydro-3-pyridinecarboxamide

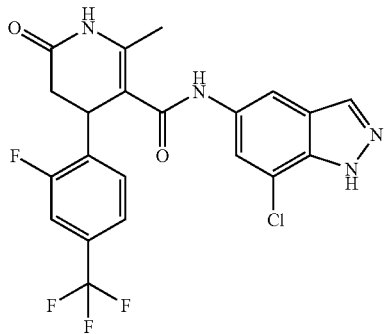

The product of Example 21, Step 2 (200 mg, 0.63 mmol, 1.00 equiv), 5-amino-7-chloroindazole (106 mg, 0.63 mmol, 1.0 equiv), and EDC (145 mg, 0.757 mmol, 1.20 equiv) were suspended in 1.5 mL DMF. Et₃N (0.106 mL, 0.757 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (20-100% EtOAc in Hexanes) and further purified by reverse-phase HPLC (10-80% CH₃CN/H₂O—NH₄OH to pH 10 over 18 minutes, retention time 12.41 min) to provide 60 mg (20%) of the title compound as a white solid. MS (ES+) m/e 467 [M+H]⁺

Example 28

4-(4-Chloro-2-fluorophenyl)-2-methyl-N-(3-methyl-1H-indazol-5-yl)-6-oxo-1,4,5,6-tetrahydro-3-pyridinecarboxamide

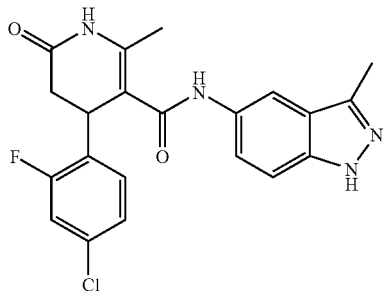

The product of Example 3, Step 2 (50 mg, 0.176 mmol, 1.00 equiv), 5-amino-3-methylindazole (26 mg, 0.176 mmol, 1.0 equiv), and EDC (41 mg, 0.212 mmol, 1.20 equiv) were suspended in 0.5 mL DMF. Et₃N (0.030 mL, 0.212 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (20-100% EtOAc in Hexanes) to provide 20 mg (27%) of the title compound as an off white solid. MS (ES+) m/e 413 [M+H]⁺

Example 29

N-(3-Bromo-1H-indazol-5-yl)-4-(4-chloro-2-fluorophenyl)-2-methyl-6-oxo-1,4,5,6-tetrahydro-3-pyridinecarboxamide

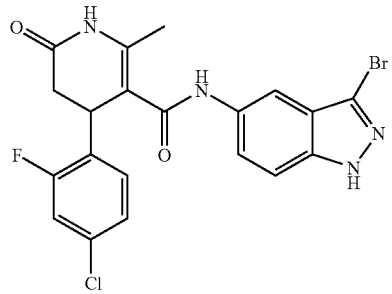

The product of Example 3, Step 2 (125 mg, 0.441 mmol, 1.00 equiv), 5-amino-3-bromoindazole (94 mg, 0.441 mmol, 1.0 equiv), and EDC (101 mg, 0.529 mmol, 1.20 equiv) were suspended in 1.0 mL DMF. Et₃N (0.074 mL, 0.529 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (20-100% EtOAc in Hexanes) to provide 21 mg (10%) of the title compound as an off white solid. MS (ES+) m/e 478 [M+H]⁺

Example 30

4-(4-Chloro-2-fluorophenyl)-N-(3-ethyl-1H-indazol-5-yl)-2-methyl-6-oxo-1,4,5,6-tetrahydro-3-pyridinecarboxamide

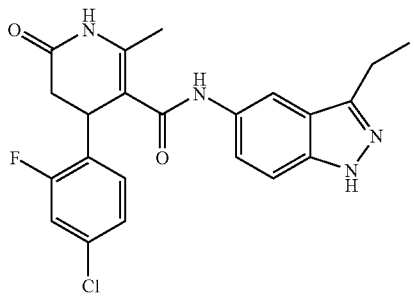

The product of Example 3, Step 2 (50 mg, 0.176 mmol, 1.00 equiv), 5-amino-3-ethylindazole (28 mg, 0.176 mmol, 1.0 equiv), and EDC (41 mg, 0.212 mmol, 1.20 equiv) were suspended in 1.5 mL DMF. Et₃N (0.030 mL, 0.212 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 26 mg (35%) of the title compound as an off white solid. MS (ES+) m/e 427 [M+H]$^+$ Example 31

4-(4-Chloro-2-fluorophenyl)-N-(6-fluoro-1H-indazol-5-yl)-2-methyl-6-oxo-1,4,5,6-tetrahydro-3-pyridinecarboxamide

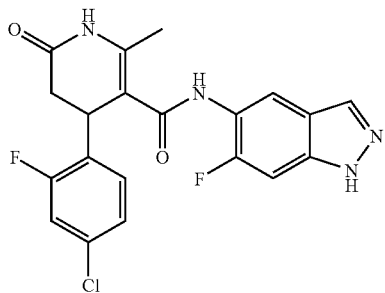

The product of Example 3, Step 2 (200 mg, 0.71 mmol, 1.00 equiv), 5-amino-6-fluoroindazole (107 mg, 0.71 mmol, 1.0 equiv), and EDC (162 mg, 0.85 mmol, 1.20 equiv) were suspended in 1.5 mL DMF. Et$_3$N (0.118 mL, 0.85 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 24 mg (8%) of the title compound as an off white solid. MS (ES+) m/e 417 [M+H]$^+$ Example 32

4-(4-Chloro-2-fluorophenyl)-2-methyl-N-(7-methyl-1H-indazol-5-yl)-6-oxo-1,4,5,6-tetrahydro-3-pyridinecarboxamide

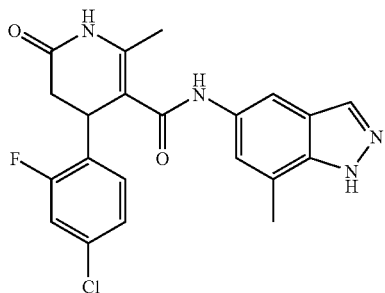

The product of Example 3 Step 2 (180 mg, 0.635 mmol, 1.00 equiv), 5-amino-7-methylindazole (94 mg, 0.635 mmol, 1.0 equiv), and EDC (145 mg, 0.761 mmol, 1.20 equiv) were suspended in 1.5 mL DMF. Et$_3$N (0.106 mL, 0.761 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was triturated with EtOAc and CH$_2$Cl$_2$, filtered, and washed with CH$_2$Cl$_2$ to provide 69 mg (26%) of the title compound as an off white solid. MS (ES+) m/e 413 [M+H]$^+$ Example 33

4-(4-Chloro-2-fluorophenyl)-N-(7-chloro-1H-indazol-5-yl)-2-methyl-6-oxo-1,4,5,6-tetrahydro-3-pyridinecarboxamide

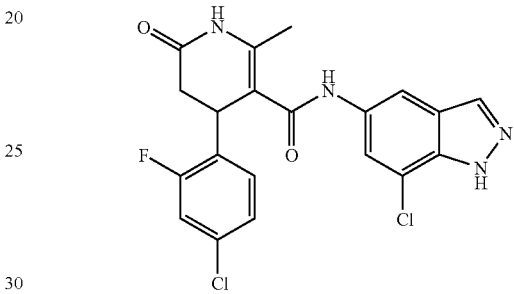

The product of Example 3 Step 2 (250 mg, 0.881 mmol, 1.00 equiv), 5-amino-7-chloroindazole (148 mg, 0.881 mmol, 1.0 equiv), and EDC (203 mg, 1.06 mmol, 1.20 equiv) were suspended in 2.0 mL DMF. Et$_3$N (0.148 mL, 1.06 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 38 mg (10%) of the title compound as an off white solid. MS (ES+) m/e 434 [M+H]$^+$ Example 34

N-(3-Bromo-1H-indazol-5-yl)-2-methyl-4-(2-naphthalenyl)-6-oxo-1,4,5,6-tetrahydro-3-pyridinecarboxamide

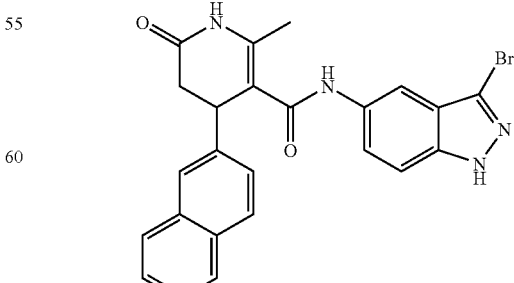

The product of Example 1, Step 2 (115 mg, 0.409 mmol, 1.00 equiv), 5-amino-3-bromoindazole (87 mg, 0.409 mmol, 1.0 equiv), and EDC (94 mg, 0.491 mmol, 1.20 equiv) were suspended in 1.0 mL DMF. Et$_3$N (0.068 mL, 0.491 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 47 mg (24%) of the title compound as an off white solid. MS (ES+) m/e 476 [M+H]$^+$ Example 35

2-Methyl-N-(3-methyl-1H-indazol-5-yl)-4-(2-naphthalenyl)-6-oxo-1,4,5,6-tetrahydro-3-pyridinecarboxamide

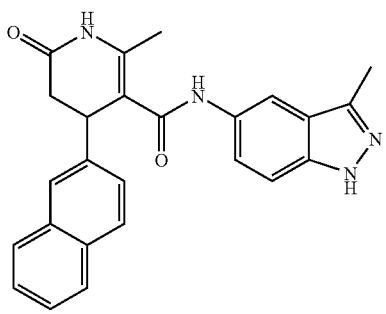

The product of Example 1, Step 2 (50 mg, 0.178 mmol, 1.00 equiv), 5-amino-3-methylindazole (26 mg, 0.178 mmol, 1.0 equiv), and EDC (41 mg, 0.213 mmol, 1.20 equiv) were suspended in 0.5 mL DMF. Et$_3$N (0.030 mL, 0.213 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 15 mg (21%) of the title compound as an off white solid. MS (ES+) m/e 411 [M+H]$^+$ Example 36

N-(3-Ethyl-1H-indazol-5-yl)-2-methyl-4-(2-naphthalenyl)-6-oxo-1,4,5,6-tetrahydro-3-pyridinecarboxamide

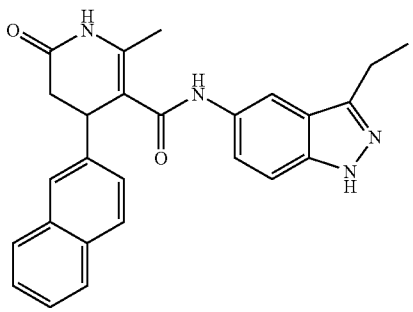

The product of Example 1, Step 2 (50 mg, 0.178 mmol, 1.00 equiv), 5-amino-3-ethylindazole (29 mg, 0.178 mmol, 1.0 equiv), and EDC (41 mg, 0.213 mmol, 1.20 equiv) were suspended in 0.5 mL DMF. Et$_3$N (0.030 mL, 0.213 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) and further purified by reverse-phase HPLC (5-85% CH$_3$CN/H$_2$O—NH$_4$OH to pH 10 over 10 minutes, retention time 6.32 min) to provide 17 mg (22%) of the title compound as a white solid. MS (ES+) m/e 425 [M+H]$^+$ Example 37

2-Methyl-N-(7-methyl-1H-indazol-5-yl)-4-(2-naphthalenyl)-6-oxo-1,4,5,6-tetrahydro-3-pyridinecarboxamide

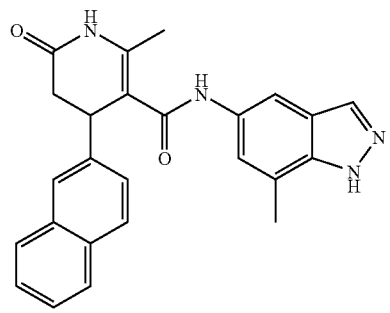

The product of Example 1, Step 2 (180 mg, 0.64 mmol, 1.00 equiv), 5-amino-7-methylindazole (94 mg, 0.64 mmol, 1.0 equiv), and EDC (147 mg, 0.768 mmol, 1.20 equiv) were suspended in 1.5 mL DMF. Et$_3$N (0.107 mL, 0.768 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was triturated with EtOAc and CH$_2$Cl$_2$, filtered, and washed with CH$_2$Cl$_2$ to provide 35 mg (13%) of the title compound as an off white solid. MS (ES+) m/e 434 [M+H]$^+$ Example 38

N-(7-Chloro-1H-indazol-5-yl)-2-methyl-4-(2-naphthalenyl)-6-oxo-1,4,5,6-tetrahydro-3-pyridinecarboxamide

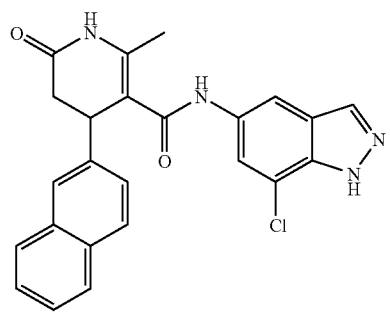

The product of Example 1, Step 2 (100 mg, 0.355 mmol, 1.00 equiv), 5-amino-7-chloroindazole (59 mg, 0.355 mmol, 1.0 equiv), and EDC (82 mg, 0.427 mmol, 1.20 equiv) were suspended in 1.0 mL DMF. Et$_3$N (0.059 mL, 0.427 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) and further purified by reverse-phase HPLC (10-80% CH$_3$CN/H$_2$O—NH$_4$OH to pH 10 over 9 minutes, retention time 6.18 min) to provide 5 mg (3%) of the title compound as a white solid. MS (ES+) m/e 431 [M+H]$^+$ Example 39

N-(3-Chloro-6-fluoro-1H-indazol-5-yl)-4-(4-chloro-2-fluorophenyl)-2-methyl-6-oxo-1,4,5,6-tetrahydro-3-pyridinecarboxamide

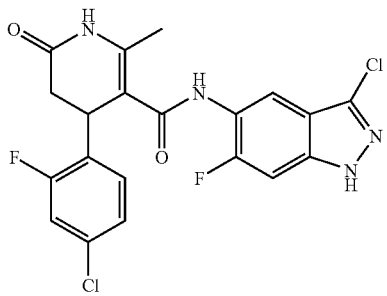

Step 1. 3-Chloro-6-fluoro-5-nitro-1H-indazole

6-Fluoro-5-nitroindazole (850 mg, 4.693 mmol, 1.0 equiv) was dissolved in 20 mL EtOH, NaOCl (10 mL, 164.26 mmol, 35 equiv) was added and the reaction mixture was stirred at room temperature for 3 hours. The reaction mixture was concentrated en vacuo to remove EtOH was then diluted with EtOAc and water. The phases were separated, and the organic phase was washed once with satd. NaHCO$_3$, and once with satd. NaCl. The organic phase was dried over Na$_2$SO$_4$, filtered, and concentrated en vacuo. The residue was purified by flash chromatography (10-100% EtOAc in Hexanes) to provide 583 mg (58%) of the title compound as a light orange solid. MS (ES+) m/e 216 [M+H]$^+$ Step 2. 3-Chloro-6-fluoro-1H-indazol-5-amine The product from Step 1 (575 mg, 2.667 mmol, 1.0 equiv) was dissolved in 15 mL EtOH and SnCl$_2$ (2.5 g, 13.337 mmol, 5.0 equiv) was added. The reaction mixture was heated to 70° C. for 4 hours. The reaction mixture was diluted with EtOAc and 6N NaOH, filtered through a pad of celite and washed with EtOAc and water. The phases of the filtrate were separated, and the organic phase was washed once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 250 mg (51%) of the title compound as a yellow solid. MS (ES+) m/e 186 [M+H]$^+$ Step 3. N-(3-Chloro-6-fluoro-1H-indazol-5-yl)-4-(4-chloro-2-fluorophenyl)-2-methyl-6-oxo-1,4,5,6-tetrahydro-3-pyridinecarboxamide The product of Example 3 Step 2 (191 mg, 0.668 mmol, 1.00 equiv), the product of Step 2 (125 mg, 0.668 mmol, 1.0 equiv), and EDC (153 mg, 0.802 mmol, 1.20 equiv) were suspended in 2.0 mL DMF. Et$_3$N (0.112 mL, 0.802 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by reverse-phase HPLC (20-90% CH$_3$CN/H$_2$O—NH$_4$OH to pH 10 over 13 minutes, retention time 7.79 min) to provide 20 mg (7%) of the title compound as a white solid. MS (ES+) m/e 452 [M+H]$^+$ Example 40

4-(4-Chlorophenyl)-N-(6-fluoro-1H-indazol-5-yl)-2-methyl-6-oxo-1,4,5,6-tetrahydro-3-pyridinecarboxamide

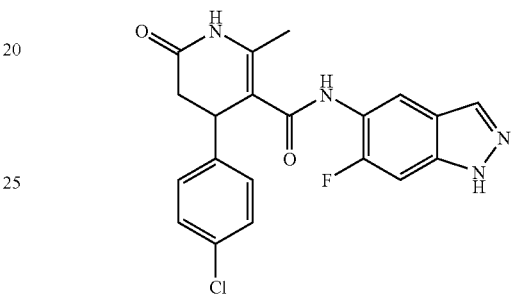

The product of Example 4 Step 2 (240 mg, 0.903 mmol, 1.00 equiv), 5-amino-6-fluoroindazole (137 mg, 0.903 mmol, 1.0 equiv), and EDC (207 mg, 1.084 mmol, 1.20 equiv) were suspended in 2.0 mL DMF. Et$_3$N (0.151 mL, 1.084 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (20-100% EtOAc in Hexanes) to provide 83 mg (23%) of the title compound as an off white solid. MS (ES+) m/e 399 [M+H]$^+$ Example 41

N-1H-Indazol-5-yl-1,2-dimethyl-6-oxo-4-[4-(trifluoromethyl)phenyl]-1,4,5,6-tetrahydro-3-pyridinecarboxamide

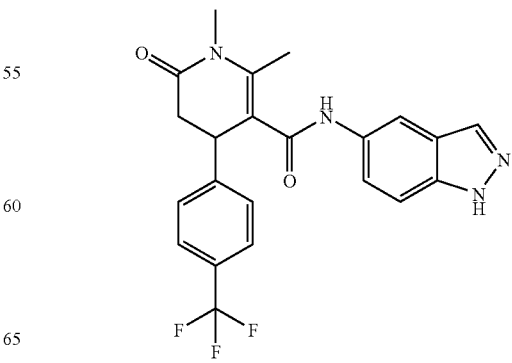

Step 1. Methyl 1,2-dimethyl-6-oxo-4-[4-(trifluoromethyl)phenyl]-1,4,5,6-tetrahydro-3-pyridinecarboxylate The product from Example 5, Step 1 (200 mg, 0.638 mmol, 1.0 equiv) dissolved in 3.0 mL DMF was cooled to 0° C. in an ice bath. NaH (26 mg, 0.638 mmol, 1.0 equiv) and MeI (0.040 mL, 0.638 mmol, 1.0 equiv) were added, and the reaction mixture was warmed to room temperature over 1 hr. After 1 hr, more NaH (13 mg, 0.319 mmol, 0.5 equiv) and MeI (0.020 mL, 0.319 mmol, 0.5 equiv) were added to the reaction mixture and stirred at room temperature for 45 min. The reaction was quenched with water and diluted with EtOAc. The phases were separated, and the organic phase was washed once with satd. NaCl. The organic phase was dried over $Na_2SO_4$, filtered, and concentrated en vacuo to provide 209 mg (100%) of the title compound as a clear oil. MS (ES+) m/e 328 $[M+H]^+$

Step 2. 1,2-Dimethyl-6-oxo-4-[4-(trifluoromethyl)phenyl]-1,4,5,6-tetrahydro-3-pyridinecarboxylic acid The title compound was synthesized using the procedure stated in Example 5, Step 2 except that the product from Step 1 was used to yield product as an off white solid. MS (ES+) m/e 314 $[M+H]^+$

Step 3. N-1H-Indazol-5-yl-1,2-dimethyl-6-oxo-4-[4-(trifluoromethyl)phenyl]-1,4,5,6-tetrahydro-3-pyridinecarboxamide The title compound was synthesized using the procedure stated in Example 1, Step 1 except that the product from Step 2 was used and the residue was additionally purified by reverse-phase HPLC (10-65% $CH_3CN/5$ mM $NH_4HCO_3$ over 20 minutes, retention time 12.55 min) to provide 16 mg (3%) of the title compound as a white solid. MS (ES+) m/e 429 $[M+H]^+$

Example 42

4-(3-Hydroxyphenyl)-N-1H-indazol-5-yl-2-methyl-6-oxo-1,4,5,6-tetrahydro-3-pyridinecarboxamide

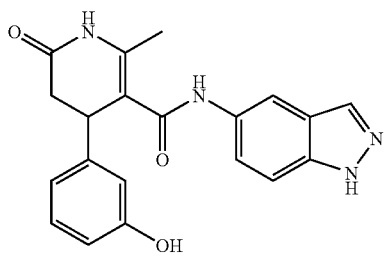

3-Hydroxybenzaldehyde (200 mg, 1.64 mmol, 1.00 equiv), 2,2-dimethyl-1,3-dioxane-4,6-dione (236 mg, 1.64 mmol, 1.00 equiv), the product of Example 6 Step 1 (356 mg, 1.64 mmol, 1.00 equiv), and ammonium acetate (132 mg, 1.72 mmol, 1.05 equiv) were dissolved in acetic acid (1.5 mL) and heated to reflux for 3 hours, then cooled to room temperature. The reaction was quenched with solid $K_2CO_3$ and then diluted slowly with water (10 mL) and EtOAc (10 mL). The phases were separated, and the organic phase was washed once with satd. NaCl. The organic phase was dried over $Na_2SO_4$, filtered, and concentrated en vacuo. The residue was purified by reverse-phase HPLC (5-50% $CH_3CN/5$ mM $NH_4HCO_3$ over 18 minutes, retention time 8.59 min) to provide 26 mg (4%) of the title compound as a white solid. MS (ES+) m/e 363 $[M+H]^+$

Example 43

4-[4-(Aminosulfonyl)phenyl]-N-1H-indazol-5-yl-2-methyl-6-oxo-1,4,5,6-tetrahydro-3-pyridinecarboxamide

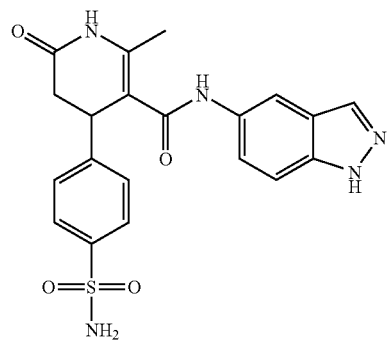

4-Formylbenzenesulfonamide (200 mg, 1.07 mmol, 1.00 equiv), 2,2-dimethyl-1,3-dioxane-4,6-dione (155 mg, 1.07 mmol, 1.00 equiv), N-1H-indazol-5-yl-3-oxobutanamidemethyl (233 mg, 1.07 mmol, 1.00 equiv), and ammonium acetate (87 mg, 1.13 mmol, 1.05 equiv) were dissolved in acetic acid (1.0 mL) and heated to reflux for 3 hours, then cooled to room temperature. The reaction was quenched with solid $K_2CO_3$ and then diluted slowly with water (10 mL) and EtOAc (10 mL). The phases were separated, and the organic phase was washed once with satd. NaCl. The organic phase was dried over $Na_2SO_4$, filtered, and concentrated en vacuo. The residue was triturated with EtOAc and $CH_2Cl_2$, filtered, and washed with EtOAc, $Et_2O$, and $CH_2Cl_2$ to provide 37 mg (8%) of the title compound as an off white solid. MS (ES+) m/e 426 $[M+H]^+$

Example 44

4-(4-Cyanophenyl)-N-1H-indazol-5-yl-2-methyl-6-oxo-1,4,5,6-tetrahydro-3-pyridinecarboxamide

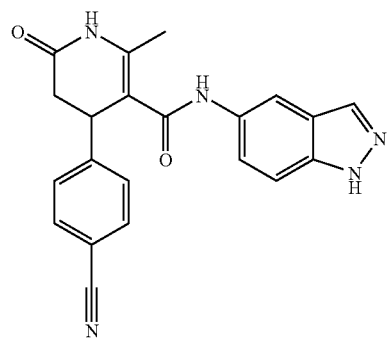

4-Formylbenzonitrile (133 mg, 1.61 mmol, 1.00 equiv), 2,2-dimethyl-1,3-dioxane-4,6-dione (232 mg, 1.61 mmol, 1.00 equiv), N-1H-indazol-5-yl-3-oxobutanamidemethyl (350 mg, 1.61 mmol, 1.00 equiv), and ammonium acetate (130 mg, 1.69 mmol, 1.05 equiv) were dissolved in acetic acid (1.5 mL) and heated to reflux for 3 hours, then cooled to room temperature. The reaction was quenched with solid K₂CO₃ and then diluted slowly with water (10 mL) and EtOAc (10 mL). The phases were separated, and the organic phase was washed once with satd. NaCl. The organic phase was dried over Na₂SO₄, filtered, and concentrated en vacuo. The residue was purified by reverse-phase HPLC (15-45% CH₃CN/5 mM NH₄HCO₃ over 20 minutes, retention time 10.65 min) to provide 40 mg (7%) of the title compound as a white solid. MS (ES+) m/e 372 [M+H]⁺

Example 45

N-(6-Fluoro-1H-yindazol-5-yl)-4-[2-fluoro-4-(trifluoromethyl)phenyl]-1,2-dimethyl-6-oxo-1,4,5,6-tetrahydro-3-pyridinecarboxamide

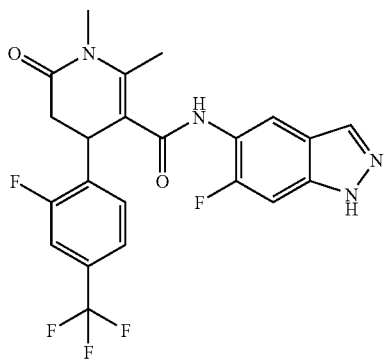

Step 1. Methyl 4-[2-fluoro-4-(trifluoromethyl)phenyl]-1,2-dimethyl-6-oxo-1,4,5,6-tetrahydro-3-pyridinecarboxylate The product of Example 21, Step 1 (3.0 g, 9.056 mmol, 1.0 equiv) was dissolved in 100 mL DMF and NaH (725 mg, 18.11 mmol, 2.0 equiv) was added slowly to the reaction mixture. Me₂SO₄ (1.72 mL, 18.11 mmol, 2.0 equiv) was added and the reaction was stirred at room temperature for 45 min. The reaction was quenched with water and diluted with EtOAc. After the phases were separated, the organic phase was washed once with satd. NaHCO₃ and once with satd. NaCl. The organic phase was dried over Na₂SO₄, filtered, and concentrated en vacuo. The residue was triturated with Et₂O and filtered to provide 1.5 g (48%) of the title compound as a light yellow solid. MS (ES+) m/e 346 [M+H]⁺

Step 2. 4-[2-Fluoro-4-(trifluoromethyl)phenyl]-1,2-dimethyl-6-oxo-1,4,5,6-tetrahydro-3-pyridinecarboxylic acid The title compound was synthesized using the procedure stated in Example 1, Step 2 except that the product from Step 1 was used and THF was not used to yield product as an off white solid. MS (ES+) m/e 332 [M+H]⁺

Step 3. N-(6-Fluoro-1H-indazol-5-yl)-4-[2-fluoro-4-(trifluoromethyl)phenyl]-1,2-dimethyl-6-oxo-1,4,5,6-tetrahydro-3-pyridinecarboxamide The product of Step 2 (165 mg, 0.498 mmol, 1.00 equiv), 5-amino-6-fluoroindazole (75 mg, 0.498 mmol, 1.0 equiv), and EDC (114 mg, 0.598 mmol, 1.20 equiv) were suspended in 1.0 mL DMF. Et₃N (0.083 mL, 0.598 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (0-80% EtOAc in Hexanes) and further purified by reverse-phase HPLC (10-80% CH₃CN/H₂O, 0.1% TFA over 24 minutes, retention time 15.55 min) to provide 7 mg (3%) of the title compound as a white solid. MS (ES+) m/e 465 [M+H]⁺

Example 46

4-[2-Fluoro-4-(trifluoromethyl)phenyl]-1,2-dimethyl-N-(3-methyl-1H-indazol-5-yl)-6-oxo-1,4,5,6-tetrahydro-3-pyridinecarboxamide

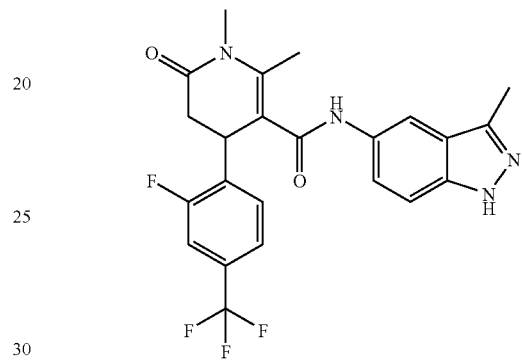

The product from Example 45, Step 2 (215 mg, 0.649 mmol, 1.00 equiv), 5-amino-3-methylindazole (96 mg, 0.649 mmol, 1.0 equiv), and EDC (149 mg, 0.779 mmol, 1.20 equiv) were suspended in 1.5 mL DMF. Et₃N (0.109 mL, 0.779 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (0-80% EtOAc in Hexanes) to provide 70 mg (23%) of the title compound as a white solid. MS (ES+) m/e 461 [M+H]⁺

Example 47

N-(3-Chloro-1H-indazol-5-yl)-4-[2-fluoro-4-(trifluoromethyl)phenyl]-1,2-dimethyl-6-oxo-1,4,5,6-tetrahydro-3-pyridinecarboxamide

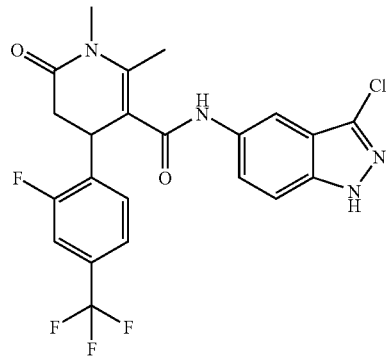

The product of Example 45, Step 1 (150 mg, 0.453 mmol, 1.00 equiv), 5-amino-3-chloroindazole (76 mg, 0.453 mmol, 1.0 equiv), and EDC (104 mg, 0.543 mmol, 1.20 equiv) were suspended in 1.0 mL DMF. Et₃N (0.076 mL, 0.543 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (0-80% EtOAc in Hexanes) and further purified by reverse-phase HPLC (30-80% CH₃CN/H₂O—NH₄OH to pH 10 over 27 minutes, retention time 13.98 min) to provide 15 mg (7%) of the title compound as a white solid. MS (ES+) m/e 481 [M+H]⁺

Example 48

4-(4-Chloro-2-fluorophenyl)-1,2-dimethyl-N-(3-methyl-1H-indazol-5-yl)-6-oxo-1,4,5,6-tetrahydro-3-pyridinecarboxamide

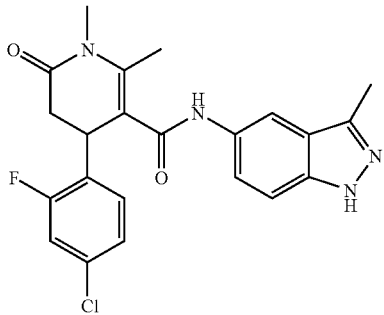

Step 1. Methyl 4-(4-chloro-2-fluorophenyl)-1,2-dimethyl-6-oxo-1,4,5,6-tetrahydro-3-pyridinecarboxylate The product of Example 3 Step 2 (3.0 g, 10.08 mmol, 1.0 equiv) was dissolved in 100 mL DMF and NaH (806 mg, 20.15 mmol, 2.0 equiv) was added slowly to the reaction mixture. Me₂SO₄ (1.9 mL, 20.15 mmol, 2.0 equiv) was added and the reaction was stirred at room temperature for 45 min. The reaction was quenched with water and filtered. The precipitate was washed with water and air dried to provide 2.29 g (73%) of the title compound as a light yellow solid. MS (ES+) m/e 312 [M+H]⁺

Step 2. 4-(4-Chloro-2-fluorophenyl)-1,2-dimethyl-6-oxo-1,4,5,6-tetrahydro-3-pyridinecarboxylic acid The title compound was synthesized using the procedure stated in Example 1, Step 2 except that the product from Step 1 was used and THF was not used to yield product as an off white solid. MS (ES+) m/e 298 [M+H]⁺

Step 3. 4-(4-Chloro-2-fluorophenyl)-1,2-dimethyl-N-(3-methyl-1H-indazol-5-yl)-6-oxo-1,4,5,6-tetrahydro-3-pyridinecarboxamide The product from Step 2 (130 mg, 0.437 mmol, 1.00 equiv), 5-amino-3-methyl indazole (64 mg, 0.437 mmol, 1.0 equiv), and EDC (100 mg, 0.524 mmol, 1.20 equiv) were suspended in 1.0 mL DMF. Et₃N (0.073 mL, 0.524 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (0-80% EtOAc in Hexanes) to provide 35 mg (19%) of the title compound as a white solid. MS (ES+) m/e 427 [M+H]⁺

Example 49

4-(4-Chloro-2-fluorophenyl)-N-(3-chloro-1H-imidazol-5-yl)-1,2-dimethyl-6-oxo-1,4,5,6-tetrahydro-3-pyridinecarboxamide

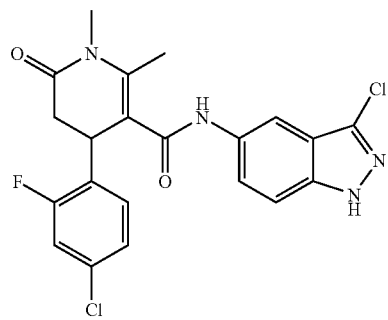

The product of Example 48, Step 2 (200 mg, 0.672 mmol, 1.00 equiv), 5-amino-3-chloroindazole (113 mg, 0.672 mmol, 1.0 equiv), and EDC (154 mg, 0.806 mmol, 1.20 equiv) were suspended in 1.5 mL DMF. Et₃N (0.112 mL, 0.806 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO₃, and once with satd. NaCl. The organic phase was dried over Na₂SO₄, filtered, and concentrated en vacuo. The residue was purified by flash chromatography (0-80% EtOAc in Hexanes) and further purified by reverse-phase HPLC (15-80% CH₃CN/H₂O—NH₄OH to pH 10 over 12 minutes, retention time 10.47 min) to provide 40 mg (13%) of the title compound as a white solid. MS (ES+) m/e 448 [M+H]⁺

Example 50

4-(4-Chloro-2-fluorophenyl)-N-(6-fluoro-1H-indazol-5-yl)-1,2-dimethyl-6-oxo-1,4,5,6-tetrahydro-3-pyridinecarboxamide

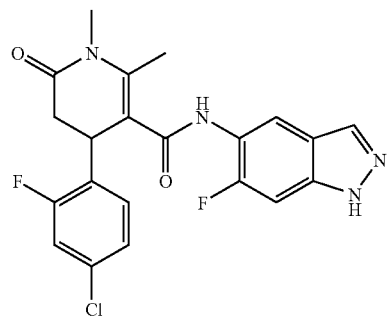

The product of Example 48, Step 2 (200 mg, 0.672 mmol, 1.00 equiv), 5-amino-6-fluoroindazole (102 mg, 0.672 mmol, 1.0 equiv), and EDC (154 mg, 0.806 mmol, 1.20 equiv) were suspended in 1.5 mL DMF. Et₃N (0.112 mL, 0.806 mmol, 1.2 equiv) was added and the solution was stirred at room temperature for 18 hrs. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (0-80% EtOAc in Hexanes) to provide 13 mg (4%) of the title compound as a white solid. MS (ES+) m/e 431 [M+H]$^+$ Example 51

N-(3-Chloro-6-fluoro-1H-indazol-5-yl)-2-methyl-6-oxo-4-[4-(trifluoromethyl)phenyl]-1,4,5,6-tetrahydro-3-pyridinecarboxamide

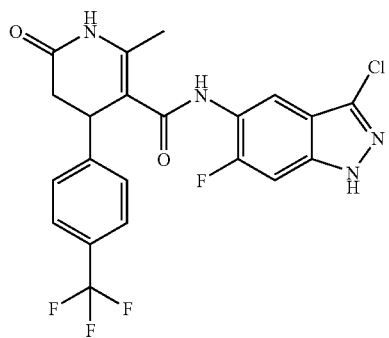

The product from Example 39, Step 2 (125 mg, 0.668 mmol, 1.0 equiv) was combined with the product from Example 5, Step 2 (200 mg, 0.668 mmol, 1.0 equiv), EDC (153 mg, 0.802 mmol, 1.2 equiv) and Et$_3$N (112 μL, 0.802 mmol, 1.2 equiv) in DMF (2 mL) and stirred at room temperature for 18 hours. The reaction mixture was diluted with EtOAc and 1N HCl. The phases were separated, and the organic phase was washed twice with 1N HCl, once with satd. NaHCO$_3$, and once with satd. NaCl. The organic phase was concentrated en vacuo. The residue was purified by flash chromatography (20-100% EtOAc in Hexanes) and further purified by reverse-phase HPLC (10-75% CH$_3$CN/H$_2$O, 0.1% TFA over 20 minutes, retention time 13.9 min) to provide 15 mg (5%) of the title compound as a white solid. MS (ES+) m/e 467 [M+H]$^+$ Example 52

N-(3-Chloro-6-fluoro-1H-indazol-5-yl)-4-[2-fluoro-4-(trifluoro-methyl)phenyl]-2-methyl-6-oxo-1,4,5,6-tetrahydro-3-pyridinecarboxamide

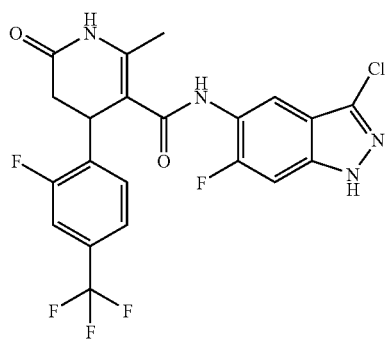

The product from Example 21, Step 2 (1.0 g, 3.152 mmol, 1.0 equiv) and oxalyl chloride (330 μL, 3.783 mmol, 1.2 equiv) in CH$_2$Cl$_2$ (12.5 mL) with catalytic DMF (20 μL) was stirred at room temperature for 45 minutes. The reaction mixture was concentrated en vacuo and half was redissolved in CH$_2$Cl$_2$ (5 mL). This solution was added dropwise over 5 minutes to a solution of the product from Example 39, step 2 (322 mg, 1.733 mmol, 1.1 equiv) in pyridine (4 mL) at −20° C. The reaction mixture was slowly warmed to room temperature over 3 hours. The reaction mixture was diluted with EtOAc and 1N HCl. The phases were separated, and the organic phase was washed twice with 1N HCl, once with satd. NaHCO$_3$, and once with satd. NaCl. The organic phase was concentrated en vacuo. The residue was purified by flash chromatography (0-80% EtOAc in Hexanes) and further purified by reverse-phase HPLC (20-90% CH$_3$CN/H$_2$O, 0.1TFA over 13 minutes, retention time 8.11 min) to provide 60 mg (8%) of the title compound as a white solid. MS (ES+) m/e 485 [M+H]$^+$ Example 53

N-(3-Chloro-6-fluoro-1H-indazol-5-yl)-4-(4-chlorophenyl)-2-methyl-6-oxo-1,4,5,6-tetrahydro-3-pyridinecarboxamide

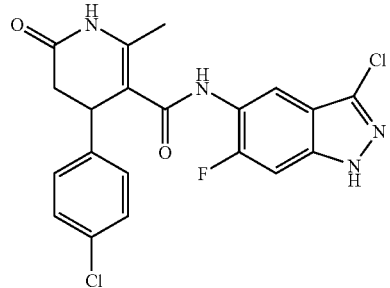

The product from Example 39, Step 2 (210 mg, 1.129 mmol, 1.0 equiv) was combined with the product from Example 4, Step 2 (300 mg, 1.129 mmol, 1.0 equiv), EDC (260 mg, 1.355 mmol, 1.2 equiv) and Et$_3$N (189 μL, 1.355 mmol, 1.2 equiv) in DMF (3 mL) and stirred at room temperature for 18 hours. The reaction mixture was diluted with EtOAc and 1N HCl. The phases were separated, and the organic phase was washed twice with 1N HCl, once with satd. NaHCO$_3$, and once with satd. NaCl. The organic phase was concentrated en vacuo. The residue was purified by flash chromatography (20-100% EtOAc in Hexanes) and further purified by reverse-phase HPLC (17-90% CH$_3$CN/H$_2$O, 0.1% TFA over 13 minutes, retention time 7.5 min) to provide 125 mg (26%) of the title compound as a white solid. MS (ES+) m/e 434 [M+H]$^+$ Example 54

4-(4-Chlorophenyl)-2-methyl-N-(3-methyl-1H-indazol-5-yl)-6-oxo-1,4,5,6-tetrahydro-3-pyridinecarboxamide

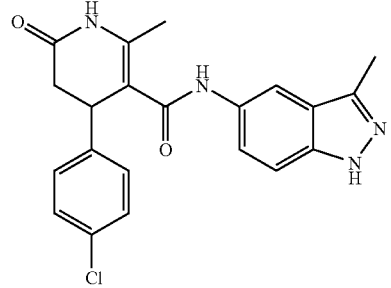

3-Methyl-1H-indazol-5-amine (166 mg, 1.129 mmol, 1.0 equiv) was combined with the product from Example 4, Step 2 (300 mg, 1.129 mmol, 1.0 equiv), EDC (260 mg, 1.355 mmol, 1.2 equiv) and Et$_3$N (189 µL, 1.355 mmol, 1.2 equiv) in DMF (3 mL) and stirred at room temperature for 18 hours. The reaction mixture was diluted with EtOAc and 1N HCl. The phases were separated, and the organic phase was washed twice with 1N HCl, once with satd. NaHCO$_3$, and once with satd. NaCl. The organic phase was concentrated en vacuo. The residue was purified by flash chromatography (20-100% EtOAc in Hexanes) to provide 105 mg (24%) of the title compound as an off white solid. MS (ES+) m/e 446 [M+H]$^+$ Example 55

N-(6-Chloro-1H-indazol-5-yl)-4-(4-chlorophenyl)-2-methyl-6-oxo-1,4,5,6-tetrahydro-3-pyridinecarboxamide

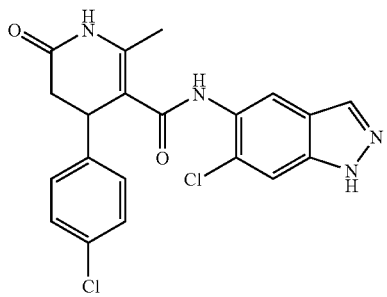

6-Chloro-1H-indazol-5-amine (64 mg, 0.382 mmol, 1.0 equiv) was combined with the product from Example 4, Step 2 (101 mg, 0.382 mmol, 1.0 equiv), EDC (88 mg, 0.458 mmol, 1.2 equiv) and Et$_3$N (64 µL, 0.458 mmol, 1.2 equiv) in DMF (1 mL) and stirred at room temperature for 18 hours. The reaction mixture was diluted with EtOAc and 1N HCl. The phases were separated, and the organic phase was washed twice with 1N HCl, once with satd. NaHCO$_3$, and once with satd. NaCl. The organic phase was concentrated en vacuo. The residue was purified by flash chromatography (0-100% EtOAc in Hexanes) and further purified by reverse-phase HPLC (15-98% CH$_3$CN/H$_2$O, adjusted to pH 10 w/NH$_4$OH over 13 minutes, retention time 6.56 min) to provide 40 mg (25%) of the title compound as a white solid. MS (ES+) m/e 416 [M+H]$^+$ Example 56

4-(4-Chlorophenyl)-N-1H-indazol-5-yl-1,2-dimethyl-6-oxo-1,4,5,6-tetrahydro-3-pyridinecarboxamide

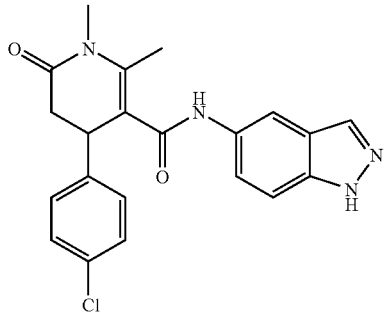

Step 1. Methyl 4-(4-chlorophenyl)-1,2-dimethyl-6-oxo-1,4,5,6-tetrahydro-3-pyridinecarboxylate The product from Example 4, Step 2 (1.0 g, 3.6 mmol, 1.0 equiv) was dissolved in DMF (36 mL) and cooled to 0° C. Sodium Hydride (144 mg, 60% in mineral oil, 3.6 mmol, 1.0 equiv) was added, followed by iodomethane (222 µL, 3.6 mmol, 1.0 equiv). The reaction was allowed to warm to room temperature and stirred for 2 hours. Additional portions of NaH (72 mg, 1.8 mmol, 0.50 equiv) and iodomethane (111 µL, 1.8 mmol, 0.50 equiv) were added and the reaction was stirred for one hour. The reaction mixture was diluted with water and EtOAc. The phases were separated and the organic phase was washed twice with satd. NaCl, dried over Na$_2$SO$_4$ and concentrated. The residue was purified by flash chromatography (linear gradient 10→50% EtOAc/Hexanes) to afford 470 mg of the title compound (45%) as an off-white powder. MS (ES+) m/e 294 [M+H]$^+$.

Step 2. 4-(4-Chlorophenyl)-1,2-dimethyl-6-oxo-1,4,5,6-tetrahydro-3-pyridinecarboxylic acid The product from step 1 (470 mg, 1.6 mmol, 1.0 equiv) was dissolved in MeOH (10 mL) and 2.5 M NaOH (2.5 mL) was added. The mixture was heated to 60° C. for three hours. When the reaction had cooled to room temperature, water and EtOAc were added. The phases were separated, and the aqueous layer was adjusted to pH 7 with 6N HCl. The aqueous phase was extracted with ethyl acetate. The organic extracts were dried over Na$_2$SO$_4$ and concentrated to dryness. The residue was azeotroped with hexanes to provide 335 mg (75%) of the title compound as a foamy white solid. MS (ES+) m/e 280 [M+H]$^+$.

Step 3. 4-(4-Chlorophenyl)-N-1H-indazol-5-yl-1,2-dimethyl-6-oxo-1,4,5,6-tetrahydro-3-pyridinecarboxamide The product of step 2 (335 mg, 1.20 mmol, 1.00 equiv), 1H-indazol-5-amine (191 mg, 1.44 mmol, 1.20 equiv) and EDC (276 mg, 1.44 mmol, 1.20 equiv) were suspended in 10.0 mL DMF. Et$_3$N (0.191 mL, 1.44 mmol, 1.20 equiv) was added and the solution was stirred 5 days at room temperature. The reaction mixture was diluted with EtOAc and 1N HCl. The phases were separated, and the organic phase was washed twice with 1N HCl, once with satd. NaHCO$_3$, and once with satd. NaCl. The organic phase was dried over Na$_2$SO$_4$, filtered, and concentrated en vacuo. The residue was purified by flash chromatography (40% 100% EtOAc) to provide 0.060 g (13%) of the title compound as a white solid. MS (ES+) m/e 395 [M+H]$^+$ Example 57

4-[2-Fluoro-4-(trifluoromethyl)phenyl]-N-1H-indazol-5-yl-1,2-dimethyl-6-oxo-1,4,5,6-tetrahydro-3-pyridinecarboxamide

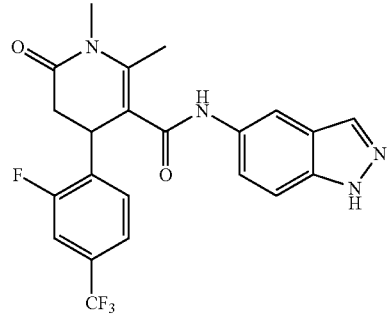

The title compound was prepared from the product of Example 21, Step 1 using the method described in Example 56 steps 1-3. MS (ES+) m/e 447 [M+H]⁺

Example 58

4-(4-Chloro-2-fluorophenyl)-N-1H-indazol-5-yl-1,2-dimethyl-6-oxo-1,4,5,6-tetrahydro-3-pyridinecarboxamide

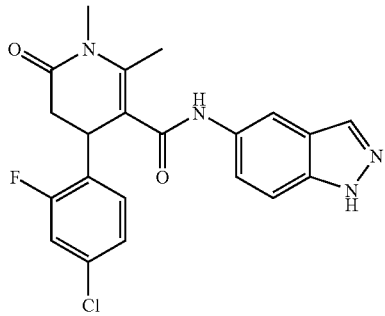

The title compound was prepared from the product of Example 3, Step 1 using the method described in Example 56 steps 1-3. MS (ES+) m/e 413 [M+H]⁺

Example 59

N-(3-Chloro-1H-indazol-5-yl)-1,2-dimethyl-6-oxo-4-[4-(trifluoromethyl)phenyl]-1,4,5,6-tetrahydro-3-pyridinecarboxamide

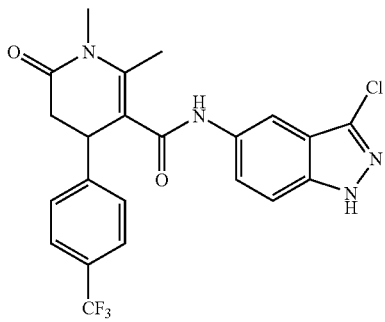

The title compound was prepared from the product of Example 41, Step 2 and 5-amino-3-chloroindazole using the method described in Example 56, Step 3. MS (ES+) m/e 463 [M+H]⁺

Example 60

N-(6-Fluoro-1H-indazol-5-yl)-1,2-dimethyl-6-oxo-4-[4-(trifluoromethyl)phenyl]-1,4,5,6-tetrahydro-3-pyridinecarboxamide

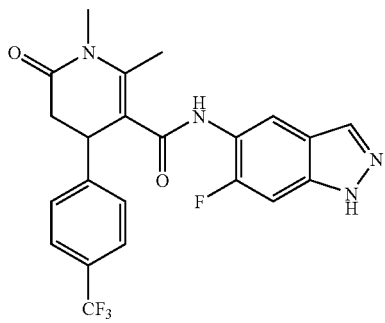

The title compound was prepared from the product of Example 41, Step 2 and 5-amino-6-fluoroindazole using the method described in Example 56, Step 3. MS (ES+) m/e 447 [M+H]⁺

Example 61

4-(4-Chlorophenyl)-N-(6-fluoro-1H-indazol-5-yl)-1,2-dimethyl-6-oxo-1,4,5,6-tetrahydro-3-pyridinecarboxamide

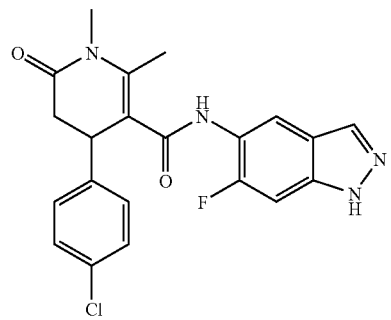

The title compound was prepared from the product of Example 56, Step 2 and 5-amino-6-fluoroindazole using the method described in Example 56, Step 3. MS (ES+) m/e 413 [M+H]⁺

Example 62

4-(4-Chlorophenyl)-1,2-dimethyl-N-(3-methyl-1H-indazol-5-yl)-6-oxo-1,4,5,6-tetrahydro-3-pyridinecarboxamide

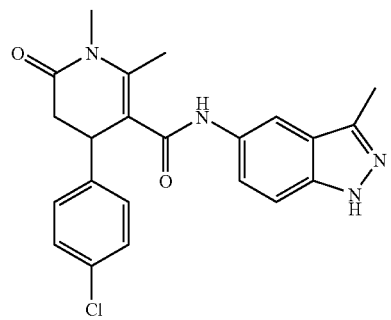

The title compound was prepared from the product of Example 56, Step 2 and 5-amino-6-fluoroindazole using the method described in Example 56, Step 3. MS (ES+) m/e 409 [M+H]⁺

Example 63

N-(6-Fluoro-1H-indazol-5-yl)-4-[2-fluoro-5-(methyloxy)phenyl]-2-methyl-6-oxo-1,4,5,6-tetrahydro-3-pyridinecarboxamide

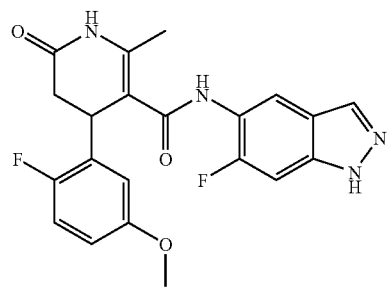

Step 1.
N-(6-Fluoro-1H-indazol-5-yl)-3-oxobutanamide

Diketene (stabilized w/copper sulfate, 1.0 mL, 12.9 mmol, 1.5 equiv) was added to a suspension of 6-fluoro-1H-indazol-5-amine (1.3 g, 8.6 mmol, 1 equiv) in acetonitrile (8 mL) at 0° C. over 30 minutes. The reaction mixture was then stirred at room temperature for 16 hours. The mixture was diluted with cold diethyl ether (20 mL) and the solid product was collected by filtration and washed several times with cold diethyl ether. The title compound was isolated as a pale brown powder (1.49 g, 74%). MS m/z 236 [M+H]$^+$

Step 2. N-(6-Fluoro-1H-indazol-5-yl)-4-[2-fluoro-5-(methyloxy)phenyl]-2-methyl-6-oxo-1,4,5,6-tetrahydro-3-pyridinecarboxamide The product of Step 1 (0.10 g, 0.43 mmol, 1.0 equiv), 2-fluoro-5-(methyloxy)benzaldehyde (66 mg, 0.43 mmol, 1.0 equiv), 2,2-dimethyl-1,3-dioxane-4,6-dione (62 mg, 0.43 mmol, 1.0 equiv), and ammonium acetate (35 mg, 0.45 mmol, 1.05 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. NaHCO$_3$. The phases were separated and the organic layer was washed with satd. NaCl, dried over Na$_2$SO$_4$, filtered and concentrated en vacuo. The residue was purified by reverse phase HPLC (Xterra Prep 30×100, 25 mL/min, 20-50% 5 mM CH$_3$CN—H$_2$O—NH$_4$OH, pH ~9 over 12 minutes) to provide product (35 mg, 20%) as a brown solid. MS (ES+) m/z 413 [M+H]$^+$.

Example 64

N-(6-Fluoro-1H-indazol-5-yl)-4-[2-fluoro-3-(methyloxy)phenyl]-2-methyl-6-oxo-1,4,5,6-tetrahydro-3-pyridinecarboxamide

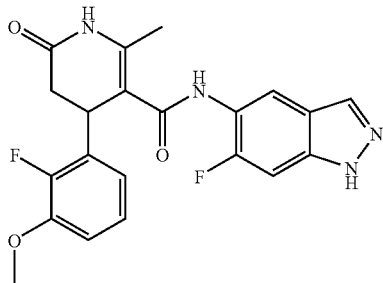

The product from Example 63, Step 1 (100 mg, 0.43 mmol, 1.00 equiv), 2-fluoro-3-(methyloxy)benzaldehyde (66 mg, 0.43 mmol, 1.00 equiv), 2,2-dimethyl-1,3-dioxane-4,6-dione (62 mg, 0.43 mmol, 1.00 equiv), and ammonium acetate (35 mg, 0.45 mmol, 1.05 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. NaHCO$_3$. The phases were separated and the organic layer was washed with satd. NaCl, dried over Na$_2$SO$_4$, filtered and concentrated en vacuo. The residue was purified by reverse phase HPLC (Xterra Prep 30×100, 25 mL/min, 20-50% 5 mM CH$_3$CN—H$_2$O—NH$_4$OH, pH~9 over 12 minutes) to provide product (29 mg, 16%) as a brown solid. MS (ES+) m/z 413 [M+H]$^+$.

Example 65

4-(2-Fluoro-5-hydroxyphenyl)-N-(6-fluoro-1H-indazol-5-yl)-2-methyl-6-oxo-1,4,5,6-tetrahydro-3-pyridinecarboxamide

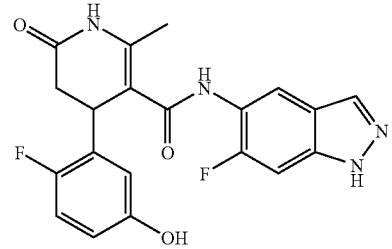

Step 1. 2-Fluoro-5-hydroxybenzaldehyde

BBr$_3$ (4 mL, 4 mmol, 1.0 M in heptane) was added dropwise to a solution of 2-fluoro-5-(methyloxy)benzaldehyde in CH$_2$Cl$_2$ at −78° C. The reaction mixture was stirred at −78° C. for 1 hour, slowly warmed to 0° C. and stirred for 2 hours. The reaction mixture was poured into water, extracted with EtOAc (3×10 mL). The extracts were combined, washed with water, brine, and dried (Na$_2$SO$_4$). The solvent was evaporated, and the residue was purified on silica gel, using 0-20% EtOAc-Hexane to give the desired product (142 mg, 25%) as a white solid. MS m/z 141 [M+H]$^+$

Step 2. 4-(2-Fluoro-5-hydroxyphenyl)-N-(6-fluoro-1H-indazol-5-yl)-2-methyl-6-oxo-1,4,5,6-tetrahydro-3-pyridinecarboxamide The product of Step 1 (60 mg, 0.43 mmol, 1.00 equiv), the product of Example 63, Step 1 (100 mg, 0.43 mmol, 1.00 equiv), 2,2-dimethyl-1,3-dioxane-4,6-dione (62 mg, 0.43 mmol, 1.00 equiv), and ammonium acetate (35 mg, 0.45 mmol, 1.05 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. NaHCO$_3$. The phases were separated and the organic layer was washed with satd. NaCl, dried over Na$_2$SO$_4$, filtered and concentrated en vacuo. The residue was purified by reverse phase HPLC (Xterra Prep 30×100, 25 mL/min, 10-40% CH$_3$CN—H$_2$O-0.1% TFA, over 12 minutes) to provide product (33 mg, 19%) as a white solid. MS (ES+) m/z 399 [M+H]$^+$.

Example 66

4-(2-Fluoro-3-hydroxyphenyl)-N-(6-fluoro-1H-indazol-5-yl)-2-methyl-6-oxo-1,4,5,6-tetrahydro-3-pyridinecarboxamide

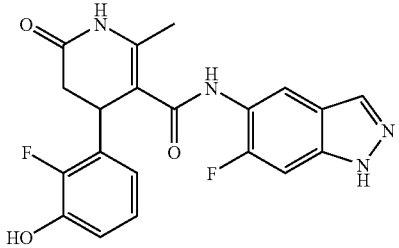

Step 1. 2-Fluoro-3-hydroxybenzaldehyde

BBr$_3$ (4 mL, 4 mmol, 1.0 M in heptane) was added dropwise to a solution of 2-fluoro-5-(methyloxy)benzaldehyde in CH$_2$Cl$_2$ at −78° C. The reaction mixture was stirred at −78° C. for 1 hour, slowly warmed to 0° C. and stirred for 2 hours. The reaction mixture was poured into water, extracted with EtOAc (3×10 mL). The extracts were combined, washed with water, brine, and dried (Na$_2$SO$_4$). The solvent was evaporated, and the residue was purified on silica gel, using 0-20% EtOAc-Hexane to give the desired product (158 mg, 28%) as a white solid. MS m/z 141 [M+H]$^+$.

Step 2. 4-(2-Fluoro-3-hydroxyphenyl)-N-(6-fluoro-1H-indazol-5-yl)-2-methyl-6-oxo-1,4,5,6-tetrahydro-3-pyridinecarboxamide The product of Step 1 (0.060 g, 0.43 mmol, 1.0 equiv), the product of Example 63, Step 1 (0.10 g, 0.43 mmol, 1.0 equiv), 2,2-dimethyl-1,3-dioxane-4,6-dione (62 mg, 0.43 mmol, 1.0 equiv), and ammonium acetate (35 mg, 0.45 mmol, 1.05 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. NaHCO$_3$. The phases were separated and the organic layer was washed with satd. NaCl, dried over Na$_2$SO$_4$, filtered and concentrated en vacuo. The residue was purified by reverse phase HPLC (Xterra Prep 30×100, 25 mL/min, 10-40% CH$_3$CN—H$_2$O-0.1% TFA, over 12 minutes) to provide product (35 mg, 20%) as a white solid. MS (ES+) m/z 399 [M+H]$^+$.

Example 67

4-[5-(Aminosulfonyl)-4-chloro-2-fluorophenyl]-N-(6-fluoro-1H-indazol-5-yl)-2-methyl-6-oxo-1,4,5,6-tetrahydro-3-pyridinecarboxamide

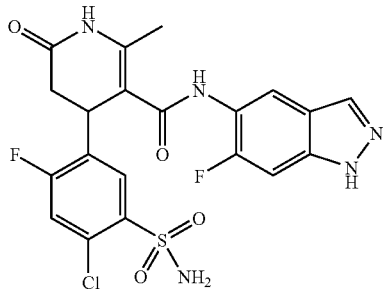

Step 1. Methyl 5-(aminosulfonyl)-4-chloro-2-fluorobenzoate 5-(Aminosulfonyl)-4-chloro-2-fluorobenzoic acid (507 mg, 2.0 mmol) in CH$_3$OH (3 mL) with 3 drops of concentrated sulfuric acid was heated at 80° C. for 60 hours. The reaction mixture was diluted with EtOAc (20 mL), washed with water, brine, and dried (Na$_2$SO$_4$). The solvent was evaporated to afford the product (508 mg, 95%) as a white solid. MS (ES+) m/z 268 [M+H]$^+$.

Step 2. 2-Chloro-4-fluoro-5-(hydroxymethyl)benzenesulfonamide

To a solution of methyl 5-(aminosulfonyl)-4-chloro-2-fluorobenzoate (500 mg, 1.87 mmol) in THF/EtOH (20 mL, 1:1), CaCl$_2$ (415 mg, 3.74 mmol) and NaBH$_4$ (283 mg, 7.48 mmol) were added in one portion respectively. The reaction mixture was stirred at room temperature for 6 hours, quenched with water. 1 M aqueous citric acid (5 mL) was added to the mixture and extracted with EtOAc (3×100 mL). The extracts were combined, washed with brine, and dried (Na$_2$SO$_4$). The solvent was evaporated to afford the product (440 mg, 98%) as a white solid. MS (ES+) m/z 262 [M+Na]$^+$.

Step 3. 2-Chloro-4-fluoro-5-formylbenzenesulfonamide

A solution of 2-chloro-4-fluoro-5-(hydroxymethyl)benzenesulfonamide (440 mg, 1.84 mmol) in acetone (18 mL) was added to a round bottom flask containing MnO$_2$ (1.60 g, 18.4 mmol). The mixture was stirred for 50 hours until the starting material was gone, then filtered though a pad of celite. The filtrate was evaporated to afford the product (263 mg, 60%) as a white solid. MS (ES+) m/z 238 [M+H]$^+$.

Step 4. 4-[5-(Aminosulfonyl)-4-chloro-2-fluorophenyl]-N-(6-fluoro-1H-indazol-5-yl)-2-methyl-6-oxo-1,4,5,6-tetrahydro-3-pyridinecarboxamide The product of Step 3 (102 mg, 0.43 mmol, 1.00 equiv), the product of Example 63, Step 1 (100 mg, 0.43 mmol, 1.00 equiv), 2,2-dimethyl-1,3-dioxane-4,6-dione (62 mg, 0.43 mmol, 1.00 equiv), and ammonium acetate (36 mg, 0.47 mmol, 1.1 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. NaHCO$_3$. The phases were separated and the organic layer was washed with satd. NaCl, dried over Na$_2$SO$_4$, filtered and concentrated en vacuo. The residue was purified by reverse phase HPLC (Xterra Prep 30×100, 25 mL/min, 10-40% CH$_3$CN—H$_2$O-0.1% TFA, over 12 minutes) to provide product (63 mg, 30%) as a white solid. MS (ES+) m/z 496 [M+H]$^+$.

Example 68

4-[3-(Aminosulfonyl)-4-chlorophenyl]-N-(6-fluoro-1H-indazol-5-yl)-2-methyl-6-oxo-1,4,5,6-tetrahydro-3-pyridinecarboxamide

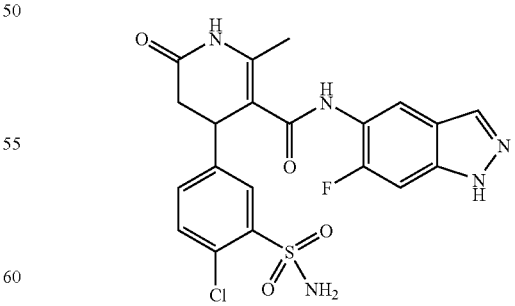

Step 1. Methyl 3-(aminosulfonyl)-4-chlorobenzoate 3-(Aminosulfonyl)-4-chlorobenzoic acid (943 mg, 4.0 mmol) was heated at 70° C. in CH$_3$OH (10 mL) with 3 drops of concentrated sulfuric acid for 34 hours. The reaction mixture was diluted with EtOAc (20 mL), washed with water, brine, and dried ($Na_2SO_4$). The solvent was evaporated to afford the product (950 mg, 95%) as a white solid. MS (ES+) m/z 250 $[M+H]^+$.

Step 2.
2-Chloro-5-(hydroxymethyl)benzenesulfonamide

To a solution of methyl 3-(aminosulfonyl)-4-chlorobenzoate (950 mg, 3.8 mmol) in THF/EtOH (40 mL, 1:1), $CaCl_2$ (843 mg, 7.6 mmol) and $NaBH_4$ (575 mg, 15.2 mmol) were added in one portion respectively. The reaction mixture was stirred at room temperature for 6 hours, then quenched with water. 1 M aqueous citric acid (10 mL) was added to the mixture and extracted with EtOAc (3×100 mL). The extracts were combined, washed with brine, and dried ($Na_2SO_4$). The solvent was evaporated to afford the product (696 mg, 83%) as a white solid. MS (ES+) m/z 244 $[M+Na]^+$.

Step 3. 2-Chloro-5-formylbenzenesulfonamide

A solution of 2-chloro-5-(hydroxymethyl)benzenesulfonamide (696 mg, 3.14 mmol) in acetone (30 mL) was added to a round bottom flask containing $MnO_2$ (2.73 g, 31.4 mmol). The mixture was stirred for 50 hours until the starting material was consumed, then filtered though a pad of celite. The filtrate was evaporated to afford the product (444 mg, 64%) as a white solid. MS (ES+) m/z 220 $[M+H]^+$.

Step 4. 4-[3-(Aminosulfonyl)-4-chlorophenyl]-N-(6-fluoro-1H-indazol-5-yl)-2-methyl-6-oxo-1,4,5,6-tetrahydro-3-pyridinecarboxamide The product of Step 3 (94 mg, 0.43 mmol, 1.00 equiv), the product of Example 63, Step 1 (100 mg, 0.43 mmol, 1.00 equiv), 2,2-dimethyl-1,3-dioxane-4,6-dione (62 mg, 0.43 mmol, 1.00 equiv), and ammonium acetate (36 mg, 0.47 mmol, 1.1 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. $NaHCO_3$. The phases were separated and the organic phase was washed with satd. NaCl, dried over $Na_2SO_4$, filtered and concentrated en vacuo. The residue was purified by reverse phase HPLC (Xterra Prep 30×100, 25 mL/min, 10-40% $CH_3CN$—$H_2O$-0.1% TFA, over 12 minutes) to provide product (44 mg, 21%) as a white solid. MS (ES+) m/z 478 $[M+H]^+$.

Example 69

4-[3-(Aminosulfonyl)phenyl]-N-(6-fluoro-1H-indazol-5-yl)-2-methyl-6-oxo-1,4,5,6-tetrahydro-3-pyridinecarboxamide Step 1. Methyl 3-(aminosulfonyl)benzoate 3-(Aminosulfonyl)benzoic acid (603 mg, 3.0 mmol) was heated at 80° C. in $CH_3OH$ (3 mL) with 3 drops of concentrated sulfuric acid for 60 hours. The reaction mixture was diluted with EtOAc (20 mL), washed with water, brine, and dried ($Na_2SO_4$). The solvent was evaporated to afford the product (630 mg, 98%) as a white solid. MS (ES+) m/z 216 $[M+H]^+$.

Step 2. 3-(Hydroxymethyl)benzenesulfonamide

To a solution of methyl 3-(aminosulfonyl)benzoate (520 mg, 2.4 mmol) in THF/EtOH (24 mL, 1:1), $CaCl_2$ (533 mg, 4.8 mmol) and $NaBH_4$ (363 mg, 9.6 mmol) were added in one portion respectively. The reaction mixture was stirred at room temperature for 6 hours, and then quenched with water. 1 M aqueous citric acid (8 mL) was added to the mixture and extracted with EtOAc (3×100 mL). The extracts were combined, washed with brine, and dried ($Na_2SO_4$). The solvent was evaporated to afford the product (307 mg, 68%) as a white solid. MS (ES+) m/z 210 $[M+Na]^+$.

Step 3. 3-Formylbenzenesulfonamide

A solution of 3-(hydroxymethyl)benzenesulfonamide (307 mg, 1.64 mmol) in acetone (16 mL) was added to a round bottom flask containing $MnO_2$ (1.43 g, 16.4 mmol). The mixture was stirred for 50 hours until the starting material was consumed, then filtered though a pad of celite. The filtrate was evaporated to afford the product (232 mg, 76%) as a white solid. MS (ES+) m/z 186 $[M+H]^+$.

Step 4. 4-[3-(Aminosulfonyl)phenyl]-N-(6-fluoro-1H-indazol-5-yl)-2-methyl-6-oxo-1,4,5,6-tetrahydro-3-pyridinecarboxamide The product of Step 3 (80 mg, 0.43 mmol, 1.00 equiv), the product of Example 63, Step 1 (100 mg, 0.43 mmol, 1.00 equiv), 2,2-dimethyl-1,3-dioxane-4,6-dione (62 mg, 0.43 mmol, 1.00 equiv), and ammonium acetate (36 mg, 0.47 mmol, 1.1 equiv) were dissolved in acetic acid (0.5 mL) and heated at 120° C. for 3 hours. Addition of water to the stirred reaction mixture induced precipitation of a solid residue. The solid was recovered by filtration and the residue was partitioned between EtOAc and satd. $NaHCO_3$. The phases were separated and the organic layer was washed with satd. NaCl, dried over $Na_2SO_4$, filtered and concentrated en vacuo. The residue was purified by reverse phase HPLC (Xterra Prep 30×100, 25 mL/min, 10-40% $CH_3CN$—$H_2O$-0.1% TFA, over 12 minutes) to provide product (49 mg, 26%) as a white solid. MS (ES+) m/z 444 $[M+H]^+$.

Example 70

4-(2,3-Difluorophenyl)-N-(6-fluoro-1H-indazol-5-yl)-2-methyl-6-oxo-1,4,5,6-tetrahydro-3-pyridinecarboxamide

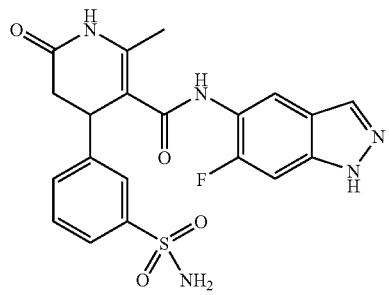

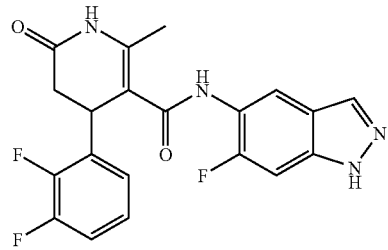

Step 1. Methyl 4-(2,3-difluorophenyl)-2-methyl-6-oxo-1,4,5,6-tetrahydro-3-pyridinecarboxylate To a mixture of 2,3-difluorobenzaldehyde (2.23 mL, 20 mmol), 2,2-dimethyl-1,3-dioxane-4,6-dione (2.88 g, 20 mmol) and ammonium acetate (1.62 g, 21 mmol) under nitrogen was added methyl 3-oxobutanoate (2.16 mL, 20 mmol) and acetic acid (20 mL). This mixture was then heated to 110° C. for 1 h. The reaction mixture was cooled to room temperature and then poured into water (80 mL). The mixture was decanted to leave a yellow oil, which was then triturated with 5% ether/hexanes to afford the title compound (1.89 g, 34%). MS (ES+) m/e 282 [M+H]$^+$.

Step 2. 4-(2,3-Difluorophenyl)-2-methyl-6-oxo-1,4,5,6-tetrahydro-3-pyridinecarboxylic acid The product from Step 1 (600 mg, 2.13 mmol) was dissolved in methanol (15 mL), NaOH solution (5 mL, 2.5 M) was added, and this reaction mixture was heated to 60° C. for 18 h. The reaction mixture was concentrated, and then poured into EtOAc (20 mL) and water (5 mL). The aqueous layer was acidified to pH<3 with 6N HCl, and extracted with EtOAc (50 mL). The organic phase was washed with brine, dried over Na$_2$SO$_4$, filtered and concentrated. The residue was triturated with 5% ether/hexanes to afford the title compound (312 mg, 55%). MS (ES+) m/e 268 [M+H]$^+$.

Step 3. 4-(2,3-Difluorophenyl)-N-(6-fluoro-1H-indazol-5-yl)-2-methyl-6-oxo-1,4,5,6-tetrahydro-3-pyridinecarboxamide The product of Step 2 (40 mg, 0.15 mmol) was suspended in CH$_2$Cl$_2$ (2 mL) under Ar. DMF (10 μL) was added, followed by oxalyl chloride (13 μL, 0.15 mmol). This mixture was stirred at rt for 30 min, then the resultant yellow solution was added to a −15° C. solution of 6-fluoro-1H-indazol-5-amine (25 mg, 0.17 mmol) in pyridine (2 mL). After stirring at −15° C. for 15 min, the reaction mixture was allowed to warm to rt over 1 h. The mixture was poured into EtOAc (50 mL), washed sequentially with aq. NH$_4$Cl (20 mL), NaOH (10 mL, 2.5 N), HCl (10 mL, 1.0 N) and satd. NaCl. The organic phase was dried over Na$_2$SO$_4$, filtered and concentrated. The residue was triturated with 10% EtOAc/10% ether/80% hexanes to afford the title compound (34 mg, 57%). MS (ES+) m/e 401 [M+H]$^+$.

Example 71

4-(2,3-Difluorophenyl)-N-1H-indazol-5-yl-2-methyl-6-oxo-1,4,5,6-tetrahydro-3-pyridinecarboxamide

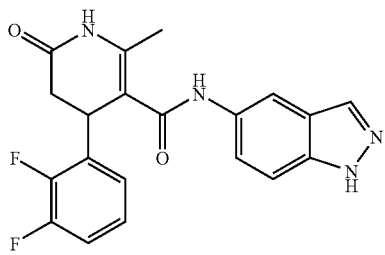

The product from Example 70, Step 2 (80 mg, 0.30 mmol) was dissolved in CH$_2$Cl$_2$ (4 mL) under Argon. DMF (20 μL) was added, followed by oxalyl chloride (27 μL, 0.30 mmol). This mixture was stirred at rt for 30 min, then the resultant yellow solution was added to a solution of 1H-indazol-5-amine (44 mg, 0.33 mmol) in pyridine (3 mL) at −15° C. under Ar. After stirring at −15° C. for 15 min, the reaction mixture was allowed to warm to rt over 1 h. The mixture was poured into EtOAc (50 mL), washed sequentially with aq. NH$_4$Cl (20 mL), NaOH (10 mL, 2.5 N), HCl (10 mL, 1.0 N) and then brine. The organic phase was dried over Na$_2$SO$_4$, filtered and concentrated. The residue was triturated with 10% ethyl acetate/10% ether/80% hexanes to afford the title compound (56 mg, 49%). MS (ES+) m/e 383 [M+H]$^+$.

Example 72

4-(2,4-Difluorophenyl)-N-(6-fluoro-1H-indazol-5-yl)-2-methyl-6-oxo-1,4,5,6-tetrahydro-3-pyridinecarboxamide

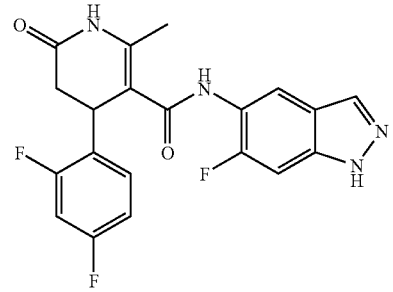

Step 1. Methyl 4-(2,4-difluorophenyl)-2-methyl-6-oxo-1,4,5,6-tetrahydro-3-pyridinecarboxylate 2,4-Difluorobenzaldehyde (3.28 mL, 30 mmol), 2,2-dimethyl-1,3-dioxane-4,6-dione (4.32 g, 30 mmol), ammonium acetate (2.46 g, 32 mmol), and methyl 3-oxobutanoate (3.23 mL, 30 mmol) were combined in acetic acid (30 mL) under nitrogen. This mixture was heated to 110° C. for 1 h. The reaction mixture was cooled to room temperature and then poured into water (100 mL). The mixture was decanted to leave yellow oil and white solid, which was taken up in MeOH/EtOAc and then concentrated. The residue was triturated with 5% ether/hexanes to afford the title compound (2.72 g, 32%). MS (ES+) m/e 282 [M+H]$^+$.

Step 2. 4-(2,4-Difluorophenyl)-2-methyl-6-oxo-1,4,5,6-tetrahydro-3-pyridinecarboxylic acid The product from Step 1 (600 mg, 2.13 mmol) was dissolved in methanol (15 mL), and NaOH (5 mL, 2.5 M) was added. This reaction mixture was heated to 60° C. for 18 h. The reaction mixture was concentrated, and then poured into EtOAc (20 mL) and water (5 mL). The aqueous layer was acidified to pH<3 by adding 6N HCl solution, and then extracted with EtOAc (50 mL). The organic phase was washed with brine, dried over Na$_2$SO$_4$, filtered and concentrated. The resulting residue was triturated with 5% ether/hexanes to afford the title compound (287 mg, 50%). MS (ES+) m/e 268 [M+H]$^+$.

Step 3. 4-(2,4-Difluorophenyl)-N-(6-fluoro-1H-indazol-5-yl)-2-methyl-6-oxo-1,4,5,6-tetrahydro-3-pyridinecarboxamide The product from Step 2 (80 mg, 0.30 mmol) was suspended in CH$_2$Cl$_2$ (3 mL) under Argon. DMF (20 μL) was added, followed by oxalyl chloride (27 μL, 0.30 mmol). This mixture was stirred at room temperature for 30 min, and the resultant yellow solution was added to a solution of 6-fluoro-1H-indazol-5-amine (50 mg, 0.33 mmol) in pyridine (3 mL) at −15° C. under Ar. After the reaction was stirred at −15° C. for 15 min, the reaction mixture was allowed to warm to room temperature over 1 h. The mixture was then poured into EtOAc (50 mL), washed sequentially with aq. NH$_4$Cl (20 mL), NaOH (10 mL, 2.5 N), HCl (10 mL, 1.0 N) and brine. The organic phase was dried over Na$_2$SO$_4$, filtered and concentrated. The residue was triturated with 10% EtOAc/10% ether/80% hexanes to afford the title compound (78 mg, 65%). MS (ES+) m/e 401 [M+H]$^+$.

Example 73

4-(2,4-Difluorophenyl)-N-(1H-indazol-5-yl)-2-methyl-6-oxo-1,4,5,6-tetrahydro-3-pyridinecarboxamide

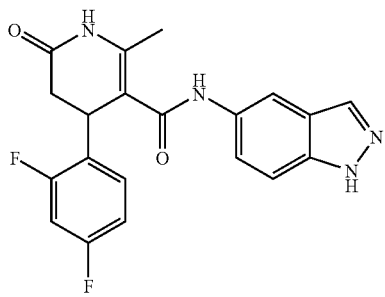

The title compound was prepared according to the procedure described in example 71, beginning with the product of Example 72, Step 2. MS (ES+) m/e 383 [M+H]$^+$.

Example 74

N-(6-Fluoro-1H-indazol-5-yl)-4-(3-hydroxyphenyl)-2-methyl-6-oxo-1,4,5,6-tetrahydro-3-pyridinecarboxamide

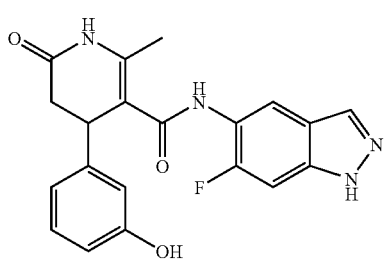

The title compound was prepared according to the procedure described in Example 6, Step 2 beginning with 3-hydroxybenzaldehyde. MS (ES+) m/e 381 [M+H]$^+$.

Example 75

N-(6-Fluoro-1H-indazol-5-yl)-2-methyl-4-{3-[(methyl-sulfonyl)amino]phenyl}-6-oxo-1,4,5,6-tetrahydro-3-pyridinecarboxamide

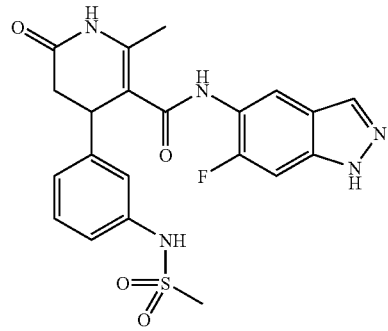

The title compound was prepared according to the procedure described in Example 6, Step 2 beginning with N-(3-formylphenyl)methanesulfonamide. MS (ES+) m/e 458 [M+H]$^+$.

Example 76

4-(4-Chloro-3-nitrophenyl)-N-(6-fluoro-1H-indazol-5-yl)-2-methyl-6-oxo-1,4,5,6-tetrahydro-3-pyridinecarboxamide

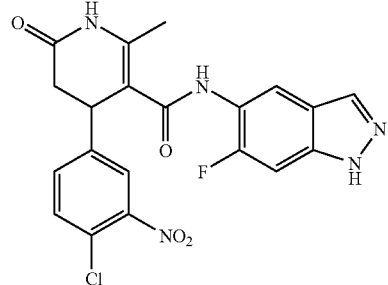

Step 1. Methyl 4-(4-chloro-3-nitrophenyl)-2-methyl-6-oxo-1,4,5,6-tetrahydropyridine-3-carboxylate The title compound was prepared according to the procedure described in Example 2, Step 1 beginning with 4-chloro-3-nitrobenzaldehyde. MS (ES+) m/e 325 [M+H]$^+$.

Step 2. 4-(4-Chloro-3-nitrophenyl)-2-methyl-6-oxo-1,4,5,6-tetrahydropyridine-3-carboxylic acid The title compound was prepared according to the procedure described in Example 2, Step 2 beginning with the product from Example 76, Step 1. MS (ES+) m/e 311 [M+H]$^+$.

Step 3. 4-(4-Chloro-3-nitrophenyl)-N-(6-fluoro-1H-indazol-5-yl)-2-methyl-6-oxo-1,4,5,6-tetrahydro-3-pyridinecarboxamide The title compound was prepared according to the procedure described in Example 70, Step 3 beginning with the product from Example 76, Step 2. MS (ES+) m/e 444 [M+H]+.

Example 77

4-(3-Amino-4-chlorophenyl)-N-(6-fluoro-1H-indazol-5-yl)-2-methyl-6-oxo-1,4,5,6-tetrahydro-3-pyridinecarboxamide

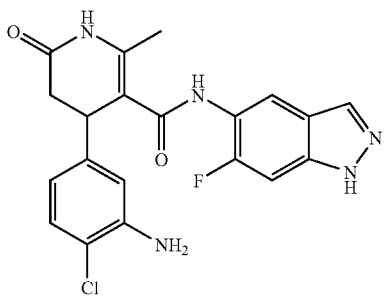

The product (222 mg, 0.5 mmol, 1.0 equiv.) from Example 76, Step 3 was dissolved in EtOAc (50 mL) and SnCl₂ (380 mg, 2.0 mmol, 4 equiv.) and H₂O (0.5 mL) were added. The mixture was refluxed for 3 h. After the reaction was cooled to room temperature, 2N NaOH was added and the mixture was stirred for 30 min. The biphasic solution was filtered through the Celite, and the phases were separated. The organic phase was washed twice with brine, dried over Na₂SO₄, and concentrated. The residue was purified by silica gel chromatography (0-10% MeOH/CH₂Cl₂) to give the title compound in 64% yield. MS (ES+) m/e 414 [M+H]+.

Example 78

4-{4-Chloro-3-[(methylsulfonyl)amino]phenyl}-N-(6-fluoro-1H-indazol-5-yl)-2-methyl-6-oxo-1,4,5,6-tetrahydro-3-pyridinecarboxamide

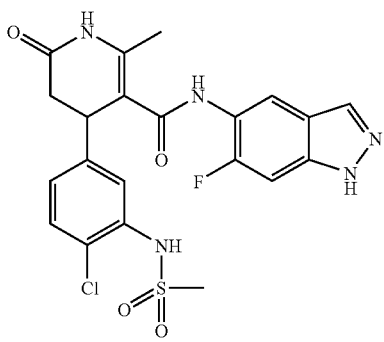

To a solution of the aniline (64 mg, 0.155 mmol, 1.0 equiv.) in pyridine was added methanesulfonyl chloride (12 uL, 0.155 mmol, 1.0 equiv.). The mixture was stirred at −10° C. for 30 min, at which point LC-MS indicated that two isomeric products had formed. An additional portion of methanesulfonyl chloride (36 uL, 3 equiv) was added and the mixture was stirred at room temperature for 3 h. The reaction mixture was diluted with sat. NH₄Cl solution and extracted with EtOAc three times. The combined organic phases were washed with 2N HCl, twice with brine, dried over Na₂SO₄ and concentrated. The residue was dissolved in MeOH (30 mL) and 2N NaOH (10 mL) was added. The mixture was concentrated under reduced pressure, and acidified to pH ~4 with 2N HCl. The mixture was extracted with EtOAc (3×) and the phases were separated. The organic phase was washed with brine (2×), dried over Na₂SO₄ and concentrated. The residue was purified by reverse phase HPLC (10%-80% MeCN/H₂O+ 0.1% TFA) to give the title compound in 50% yield. MS (ES+) m/e 492 [M+H]+.

Example 79

N-(6-Fluoro-1H-indazol-5-yl)-2-methyl-4-[3-nitro-4-(trifluoromethyl)phenyl]-6-oxo-1,4,5,6-tetrahydro-3-pyridinecarboxamide

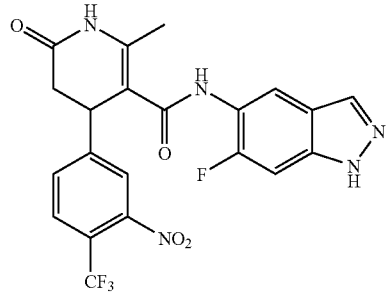

Step 1. 3-Nitro-4-(trifluoromethyl)benzaldehyde

To a solution of 4-chloro-3-nitrobenzaldehyde (5.57 g, 30 mmol, 1.0 equiv.) in N,N-dimethylacetamide was added Cu (11.5 g, 180 mmol, 6.0 equiv.) and CF₂Br₂ (6.0 mL, 63 mmol, 2.1 equiv.). The mixture was heated at 100° C. for 7 h. After the reaction was cooled to room temperature, it was filtered through Celite, and washed with EtOAc. The phases were separated and the organic phase was washed twice with brine, dried over Na₂SO₄ and concentrated. The residue was purified by silica gel chromatography (0-10% EtOAc/Hexane) to give the title compound in 60% yield. ¹H NMR (400 MHz, DMSO-d₆), 10.16 (1H, s), 8.62 (1H, s), 8.41 (1H, d, 8.0 Hz), 8.31 (1H, d, 8.0 Hz).

Step 2. Methyl 2-methyl-4-[3-nitro-4-(trifluoromethyl)phenyl]-6-oxo-1,4,5,6-tetrahydropyridine-3-carboxylate The title compound was prepared according to the procedure described in Example 2, Step 1 beginning with the product from Example 79, Step 1. MS (ES+) m/e 359 [M+H]+.

Step 3. 2-Methyl-4-[3-nitro-4-(trifluoromethyl)phenyl]-6-oxo-1,4,5,6-tetrahydropyridine-3-carboxylic acid The title compound was prepared according to the procedure described in Example 2, Step 2 beginning with the product from Example 79, Step 2. MS (ES+) m/e 345 [M+H]+.

Step 4. N-(6-Fluoro-1H-indazol-5-yl)-2-methyl-4-[3-nitro-4-(trifluoromethyl)phenyl]-6-oxo-1,4,5,6-tetrahydro-3-pyridinecarboxamide The title compound was prepared according to the procedure described in Example 70, Step 3 beginning with the product from Example 78, Step 2. MS (ES+) m/e 478 [M+H]$^+$.

Example 80

4-[3-Amino-4-(trifluoromethyl)phenyl]-N-(6-fluoro-1H-indazol-5-yl)-2-methyl-6-oxo-1,4,5,6-tetrahydro-3-pyridinecarboxamide

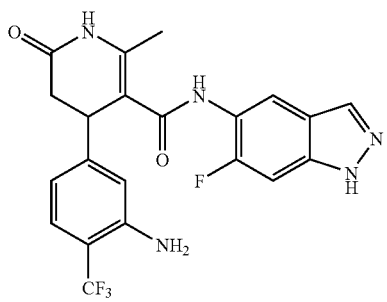

The title compound was prepared according to the procedure described in Example 77, beginning with the product from Example 79. MS (ES+) m/e 414 [M+H]$^+$.

Example 81

N-(6-Fluoro-1H-indazol-5-yl)-2-methyl-4-[3-[(methylsulfonyl)amino]-4-(trifluoromethyl)phenyl]-6-oxo-1,4,5,6-tetrahydro-3-pyridinecarboxamide

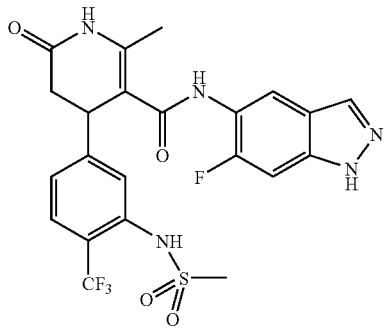

The title compound was prepared according to the procedure described in Example 78, beginning with the product from Example 80. MS (ES+) m/e 414 [M+H]$^+$ Example 82

4-[3-[(Ethylsulfonyl)amino]-4-(trifluoromethyl)phenyl]-N-(6-fluoro-1H-indazol-5-yl)-2-methyl-6-oxo-1,4,5,6-tetrahydro-3-pyridinecarboxamide

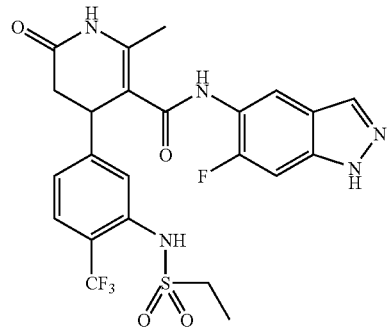

The title compound was prepared according to the procedure described in Example 78, beginning with the product from Example 80 and using ethanesulfonyl chloride in place of methanesulfonyl chloride. MS (ES+) m/e 414 [M+H]$^+$.

Example 83

N-(6-Fluoro-1H-indazol-5-yl)-4-(2-fluoro-5-nitrophenyl)-2-methyl-6-oxo-1,4,5,6-tetrahydro-3-pyridinecarboxamide

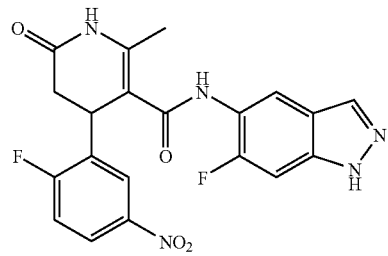

The title compound was prepared according to the procedure described in Example 6, Step 2 beginning with 2-fluoro-5-nitrobenzaldehyde. MS (ES+) m/e 428 [M+H]$^+$ Example 84

N-(6-Fluoro-1H-indazol-5-yl)-4-[4-fluoro-3-(trifluoromethyl)phenyl]-2-methyl-6-oxo-1,4,5,6-tetrahydro-3-pyridinecarboxamide

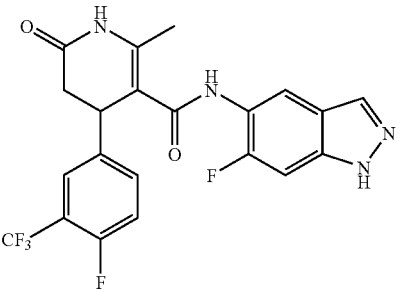

The title compound was prepared according to the procedure described in Example 6, Step 2 beginning with 4-fluoro-3-trifluoromethylbenzaldehyde. MS (ES+) m/e 451 [M+H]$^+$.

Example 85

4-[2,3-Difluoro-4-(trifluoromethyl)phenyl]-N-(6-fluoro-1H-indazol-5-yl)-2-methyl-6-oxo-1,4,5,6-tetrahydro-3-pyridinecarboxamide

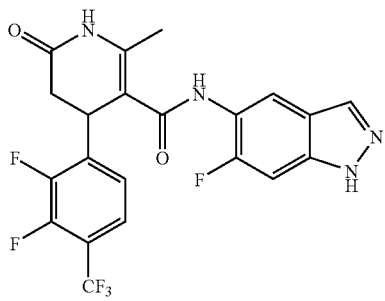

The title compound was prepared according to the procedure described in Example 6, Step 2 beginning with 2,3-difluoro-4-trifluoromethylbenzaldehyde. MS (ES+) m/e 469 [M+H]+.

Example 86

N-(6-Fluoro-1H-indazol-5-yl)-4-[3-fluoro-4-(trifluoromethyl)phenyl]-2-methyl-6-oxo-1,4,5,6-tetrahydro-3-pyridinecarboxamide

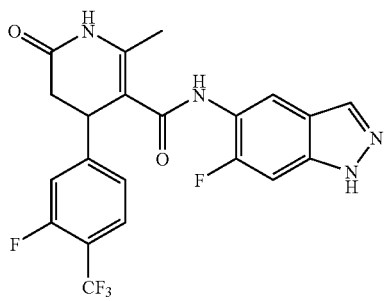

The title compound was prepared according to the procedure described in Example 6, Step 2 beginning with 3-fluoro-4-trifluoromethylbenzaldehyde. MS (ES+) m/e 451 [M+H]+.

Example 87

4-(4-Cyanophenyl)-N-(6-fluoro-1H-indazol-5-yl)-2-methyl-6-oxo-1,4,5,6-tetrahydro-3-pyridinecarboxamide

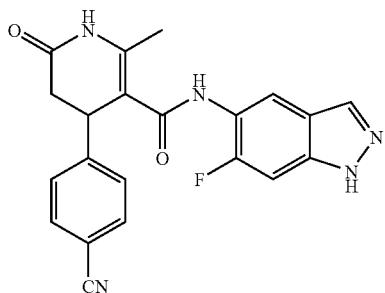

The title compound was prepared according to the procedure described in Example 6, Step 2 beginning with 4-cyanobenzaldehyde. MS (ES+) m/e 390 [M+H]+.

Example 88

4-(4-Biphenylyl)-N-(6-fluoro-1H-indazol-5-yl)-2-methyl-6-oxo-1,4,5,6-tetrahydro-3-pyridinecarboxamide

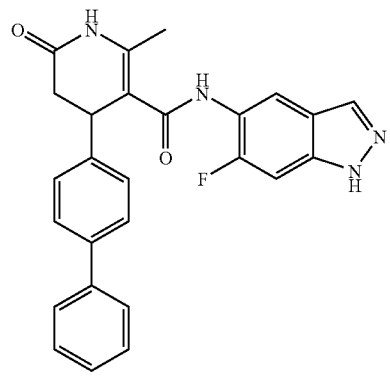

The title compound was prepared according to the procedure described in Example 6, Step 2 beginning with 4-phenylbenzaldehyde. MS (ES+) m/e 441 [M+H]+.

Example 89

N-(6-Fluoro-1H-indazol-5-yl)-2-methyl-6-oxo-4-[4-(2-thienyl)phenyl]-1,4,5,6-tetrahydro-3-pyridinecarboxamide

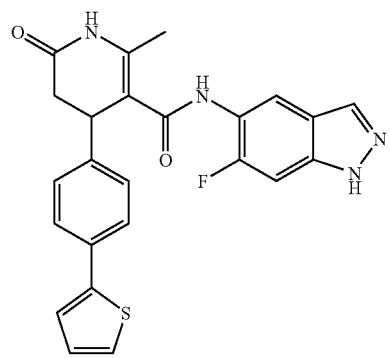

The title compound was prepared according to the procedure described in Example 6, Step 2 beginning with 4-(2-thienyl)benzaldehyde. MS (ES+) m/e 447 [M+H]+.

Example 90

4-(4-Bromophenyl)-N-(6-fluoro-1H-indazol-5-yl)-2-methyl-6-oxo-1,4,5,6-tetrahydro-3-pyridinecarboxamide

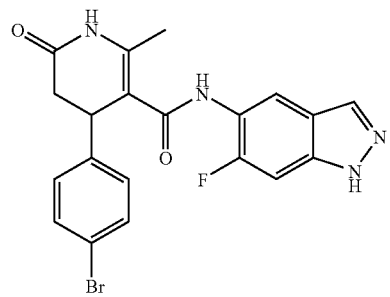

The title compound was prepared according to the procedure described in Example 6, Step 2 beginning with 4-bromobenzaldehyde. MS (ES+) m/e 447 [M+H]⁺.

Example 91

4-(5-Cyano-2-fluorophenyl)-N-(6-fluoro-1H-indazol-5-yl)-2-methyl-6-oxo-1,4,5,6-tetrahydro-3-pyridinecarboxamide

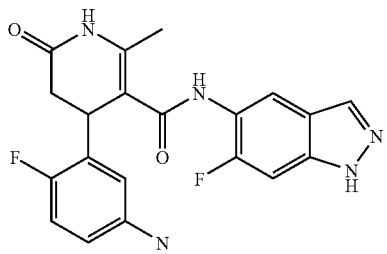

The title compound was prepared according to the procedure described in Example 6, Step 2 beginning with 2-fluoro-5-cyanobenzaldehyde. MS (ES+) m/e 408 [M+H]⁺.

Example 92

N-(6-Fluoro-1H-indazol-5-yl)-4-[2-fluoro-4-(methyloxy)phenyl]-2-methyl-6-oxo-1,4,5,6-tetrahydro-3-pyridinecarboxamide

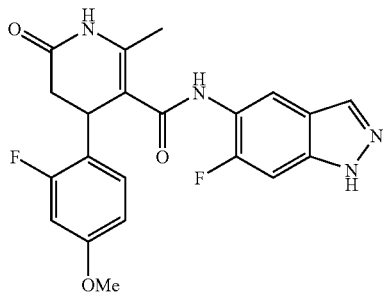

The title compound was prepared according to the procedure described in Example 6, Step 2 beginning with 2-fluoro-4-methoxybenzaldehyde. MS (ES+) m/e 413 [M+H]⁺.

Example 93

N-(3-Chloro-1H-indazol-5-yl)-4-[4-chloro-3-(methyloxy)phenyl]-2-methyl-6-oxo-1,4,5,6-tetrahydro-3-pyridinecarboxamide

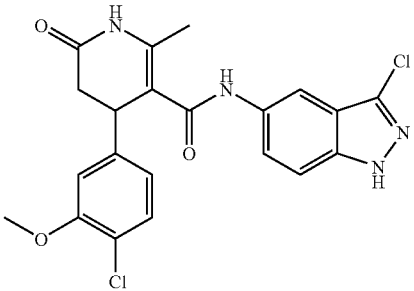

Step 1. 1-Chloro-4-methyl-2-(methyloxy)benzene

2-Chloro-5-methylphenol (5.00 g, 35.0 mmol, 1.00 equiv) and potassium carbonate (29.0 g, 2.10 mol, 6 equiv) were combined in DMF and stirred 15 minutes. Dimethyl sulfate (9.95 mL, 1.05 mol, 3.00 equiv) was added and the mixture was heated to 70° C. After 1 hour, the reaction was cooled to room temperature and stirred an additional 18 hours. The mixture was diluted with 200 mL H₂O and extracted with Et₂O. The organic phase was washed three times with H₂O and once with brine, then dried over MgSO₄ and concentrated en vacuo. 5.48 g (100%) of the product was obtained as a red liquid. ¹H NMR (400 MHz, CDCl₃) 7.25 (d, 1H), 6.77 (s, 1H), 6.73 (d, 1H), 3.91 (s, 3H), 2.56 (s, 3H).

Step 2. 4-Chloro-3-(methyloxy)benzaldehyde

Ceric ammonium nitrate (43.3 g, 79.0 mmol, 4.00 equiv) was dissolved in 1:1 HOAc/H₂O (200 mL). This solution was added dropwise over one hour to a stirred solution of the product from Step 1 (3.09 g, 19.7 mmol, 1.00 equiv) in 1:1 HOAc/H₂O (100 mL) at 100° C. After the addition was complete, the reaction was stirred for an additional 15 minutes. The reaction was cooled, diluted with H₂O and extracted twice with Et₂O. The combined organic extracts were washed three times with H₂O, three times with satd. NaHCO₃, and once with brine. The organic phase was dried over MgSO₄ and concentrated en vacuo to afford the title compound (3.00 g, 89%) as an amber oil. ¹H NMR (400 MHz, CDCL₃) 9.97 (s, 1H), 7.57 (d, 1H), 7.46 (s, 1H), 7.43 (d, 1H), 4.00 (s, 3H).

Step 3. Methyl 4-[4-chloro-3-(methyloxy)phenyl]-2-methyl-6-oxo-1,4,5,6-tetrahydro-3-pyridinecarboxylate The title compound was prepared according to the general procedure described in Example 1, Step 1, beginning with the product of Example 93, Step 2. MS (ES+) m/e 310 [M+H]⁺

Step 4. 4-[4-Chloro-3-(methyloxy)phenyl]-2-methyl-6-oxo-1,4,5,6-tetrahydro-3-pyridinecarboxylic acid The title compound was prepared according to the general procedure described in Example 5, Step 2, beginning with the product of Example 93, Step 3. MS (ES+) m/e 296 [M+H]⁺

Step 5. N-(3-Chloro-1H-indazol-5-yl)-4-[4-chloro-3-(methyloxy)phenyl]-2-methyl-6-oxo-1,4,5,6-tetrahydro-3-pyridinecarboxamide 3-Chloro-1H-indazol-5-amine (99 mg, 0.59 mmol, 1.0 equiv) was combined with the product of Step 4 (175 mg, 0.592 mmol, 1.00 equiv), EDC (134 mg, 0.710 mmol, 1.20 equiv) and Et₃N (99.0 μL, 0.710 mmol, 1.20 equiv) in DMF (1.75 mL) and stirred at 30° C. for 18 hours. The reaction mixture was diluted with EtOAc and 1N HCl. The phases were separated, and the organic phase was washed twice with 1N HCl, once with satd. NaHCO₃, and once with satd. NaCl. Solid precipitated out of the organic phase and was filtered and triturated with ether to provide 125 mg (47%) of the title compound as a white solid. MS (ES+) m/e 446 [M+H]⁺

Example 94

N-(3-Bromo-1H-indazol-5-yl)-4-[4-chloro-3-(methyloxy)phenyl]-2-methyl-6-oxo-1,4,5,6-tetrahydro-3-pyridinecarboxamide

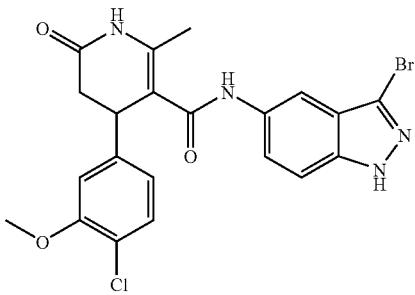

3-Bromo-1H-indazol-5-amine (126 mg, 0.592 mmol, 1.00 equiv) was combined with the product from Example 93, Step 4 (175 mg, 0.592 mmol, 1.00 equiv), EDC (134 mg, 0.710 mmol, 1.20 equiv) and $Et_3N$ (99 μL, 0.710 mmol, 1.20 equiv) in DMF (1.75 mL) and stirred at 30° C. for 18 hours. The reaction mixture was diluted with EtOAc and 1N HCl. The phases were separated, and the organic phase was washed twice with 1N HCl, once with satd. $NaHCO_3$, and once with satd. NaCl. Solid precipitated out of the organic phase and was filtered and triturated with ether to provide 145 mg (50%) of the title compound as a white solid. MS (ES+) m/e 490 $[M+H]^+$

Example 95

4-[4-Chloro-3-(methyloxy)phenyl]-2-methyl-N-(3-methyl-1H-indazol-5-yl)-6-oxo-1,4,5,6-tetrahydro-3-pyridinecarboxamide

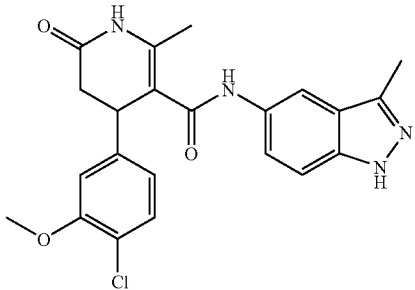

3-Methyl-1H-indazol-5-amine (87 mg, 0.592 mmol, 1.0 equiv) was combined with the product of Example 93, Step 4 (175 mg, 0.592 mmol, 1.0 equiv), EDC (134 mg, 0.710 mmol, 1.2 equiv) and $Et_3N$ (99 μL, 0.710 mmol, 1.2 equiv) in DMF (1.75 mL) and stirred at 30° C. for 18 hours. The reaction mixture was diluted with EtOAc and 1N HCl. The phases were separated, and the organic phase was washed twice with 1N HCl, once with satd. $NaHCO_3$, and once with satd. NaCl. Solid precipitated out of the organic phase and was filtered and triturated with ether to provide 155 mg (62%) of the title compound as a white solid. MS (ES+) m/e 425 $[M+H]^+$

Example 96

4-[4-Chloro-3-(methyloxy)phenyl]-N-(3-ethyl-1H-indazol-5-yl)-2-methyl-6-oxo-1,4,5,6-tetrahydro-3-pyridinecarboxamide

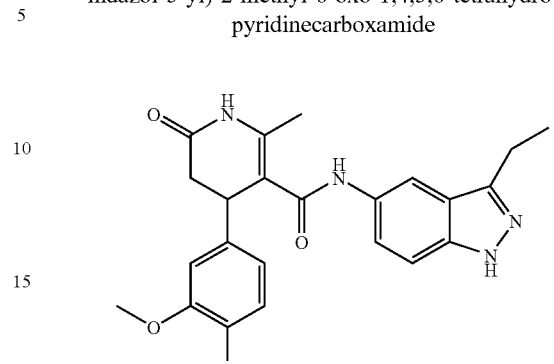

3-Ethyl-1H-indazol-5-amine (218 mg, 1.35 mmol, 1.00 equiv) was combined with the product from Example 93, Step 4 (0.400 g, 1.35 mmol, 1.00 equiv), EDC (0.310 g, 1.62 mmol, 1.2 equiv) and $Et_3N$ (226 μL, 1.62 mmol, 1.20 equiv) in DMF (4 mL) and stirred at 30° C. for 18 hours. The reaction mixture was diluted with EtOAc and 1N HCl. The phases were separated, and the organic phase was washed twice with 1N HCl, once with satd. $NaHCO_3$, and once with satd. NaCl. Solid precipitated out of the organic phase and was filtered and triturated with ether to provide 295 mg (50%) of the title compound as a white solid. MS (ES+) m/e 439 $[M+H]^+$

Example 97

4-[4-Chloro-3-(methyloxy)phenyl]-N-(6-fluoro-1H-indazol-5-yl)-2-methyl-6-oxo-1,4,5,6-tetrahydro-3-pyridinecarboxamide

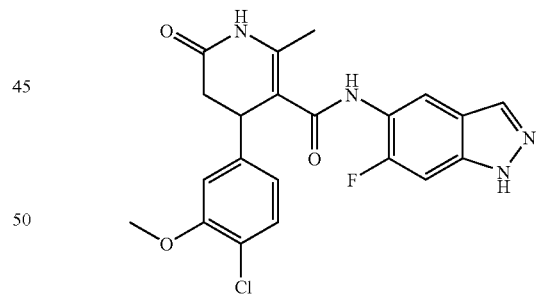

6-Fluoro-1H-indazol-5-amine (102 mg, 0.676 mmol, 1.0 equiv) was combined with the product from Example 93, Step 4 (0.200 g, 0.676 mmol, 1.0 equiv), EDC (155 mg, 0.812 mmol, 1.2 equiv) and $Et_3N$ (113 μL, 0.812 mmol, 1.2 equiv) in DMF (2 mL) and stirred at 30° C. for 18 hours. The reaction mixture was diluted with EtOAc and 1N HCl. The phases were separated, and the organic phase was washed twice with 1N HCl, once with satd. $NaHCO_3$, and once with satd. NaCl. Solid precipitated out of the organic phase and was filtered and triturated with ether to provide 85.0 mg (29%) of the title compound as a white solid. MS (ES+) m/e 429 $[M+H]^+$

Example 98

4-(4-Chloro-3-hydroxyphenyl)-N-(3-chloro-1H-indazol-5-yl)-2-methyl-6-oxo-1,4,5,6-tetrahydro-3-pyridinecarboxamide

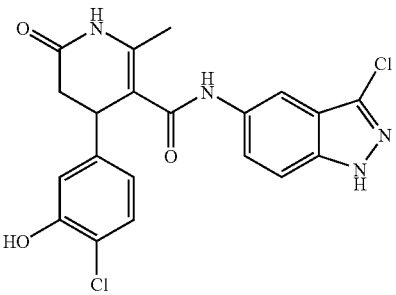

The product of Example 93, Step 5 (75 mg, 0.168 mmol, 1.0 equiv) was cooled to −78° C. in 1.75 mL CH$_2$Cl$_2$ and BCl$_3$ (1.0 M in CH$_2$Cl$_2$, 2.5 mL, 2.526 mmol, 15.0 equiv) was added dropwise. The reaction was warmed to 35° C. and stirred for 90 hours. An additional portion of BCl$_3$ (2.5 mL, 2.526 mmol, 15.0 equiv) in CH$_2$Cl$_2$ was added dropwise and the reaction was stirred for another 96 hours. The reaction mixture was diluted with EtOAc and water and basified to pH 14 with 6N NaOH. The phases were separated, and the aqueous phase was acidified to pH 4 with 6N HCl. The precipitate was filtered and washed with Et$_2$O. The residue was purified by reverse-phase HPLC (10-90% CH$_3$CN/H$_2$O, 0.1% TFA over 18 minutes, retention time 10.55 min) to provide 16 mg (22%) of the title compound as a white solid. MS (ES+) m/e 432 [M+H]$^+$

Example 99

N-(3-Bromo-1H-indazol-5-yl)-4-(4-chloro-3-hydroxyphenyl)-2-methyl-6-oxo-1,4,5,6-tetrahydro-3-pyridinecarboxamide

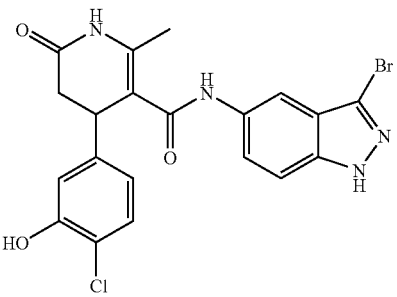

The product from Example 94 (95 mg, 0.19 mmol, 1.0 equiv) was cooled to −78° C. in 2.0 mL CH$_2$Cl$_2$ and BCl$_3$ (1.0 M in CH$_2$Cl$_2$, 2.90 mL, 2.91 mmol, 15.0 equiv) was added dropwise. The reaction was warmed to 35° C. and stirred for 90 hours. An additional portion of BCl$_3$ (2.90 mL, 2.91 mmol, 15.0 equiv) was added dropwise and the reaction was stirred for another 96 hours. The reaction mixture was diluted with EtOAc and water and basified to pH 14 with 6N NaOH. The phases were separated, and the aqueous phase was acidified to pH 4 with 6N HCl. The precipitate was filtered and washed with Et$_2$O. The residue was purified by reverse-phase HPLC (10-95% CH$_3$CN/H$_2$O, 0.1% TFA over 18 minutes, retention time 10.63 min) to provide 25 mg (27%) of the title compound as a white solid. MS (ES+) m/e 476 [M+H]$^+$

Example 100

4-(4-Chloro-3-hydroxyphenyl)-2-methyl-N-(3-methyl-1H-indazol-5-yl)-6-oxo-1,4,5,6-tetrahydro-3-pyridinecarboxamide

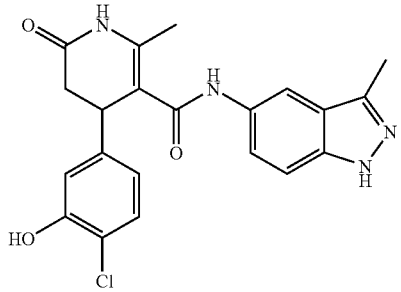

The product from Example 95 (105 mg, 0.247 mmol, 1.00 equiv) was cooled to −78° C. in 2.0 mL CH$_2$Cl$_2$ and BCl$_3$ (1.0 M in CH$_2$Cl$_2$, 3.70 mL, 3.71 mmol, 15.0 equiv) was added dropwise. The reaction was warmed to 35° C. and stirred for 90 hours. The reaction mixture was diluted with EtOAc and water and basified to pH 14 with 6N NaOH. The phases were separated, and the aqueous phase was acidified to pH 4 with 6N HCl. The precipitate was filtered and washed with Et$_2$O. The residue was purified by reverse-phase HPLC (10-95% CH$_3$CN/H$_2$O, 0.1% TFA over 18 minutes, retention time 9.15 min) to provide 20 mg (20%) of the title compound as a white solid. MS (ES+) m/e 411 [M+H]$^+$

Example 101

4-(4-Chloro-3-hydroxyphenyl)-N-(3-ethyl-1H-indazol-5-yl)-2-methyl-6-oxo-1,4,5,6-tetrahydro-3-pyridinecarboxamide

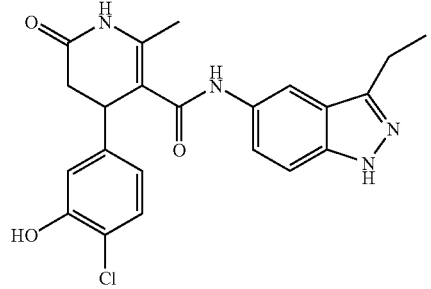

The product from Example 96 (0.050 g, 0.11 mmol, 1.0 equiv) was cooled to −78° C. in 1.5 mL CH$_2$Cl$_2$ and BCl$_3$ (1.0 M in CH$_2$C$_2$, 1.70 mL, 1.71 mmol, 15.0 equiv) was added dropwise. The reaction was warmed to 30° C. and stirred for 72 hours. The reaction mixture was diluted with EtOAc and water and basified to pH 14 with 6N NaOH. The phases were separated, and the aqueous phase was acidified to pH 4 with 6N HCl and the product was extracted into EtOAc. The organic layer was washed with sat'd NaCl and concentrated en vacuo. The residue purified by reverse-phase HPLC (10-

95% CH$_3$CN/H$_2$O, 0.1% TFA over 6 minutes, retention time 3.48 min) to provide 1 mg (0.7%) of the title compound as a white solid. MS (ES+) m/e 425 [M+H]$^+$ Example 102

4-(4-Chloro-3-hydroxyphenyl)-N-(6-fluoro-1H-indazol-5-yl)-2-methyl-6-oxo-1,4,5,6-tetrahydro-3-pyridinecarboxamide

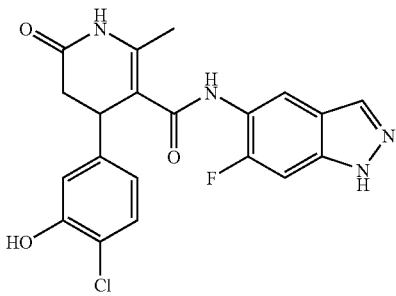

The compound from Example 102 (35 mg, 0.082 mmol, 1.0 equiv) was cooled to −78° C. in 1.25 mL CH$_2$Cl$_2$ and BCl$_3$ (1.0 M in CH$_2$C$_2$, 1.20 mL, 1.22 mmol, 15.0 equiv) was added dropwise. The reaction was warmed to 35° C. and stirred for 90 hours. The reaction mixture was diluted with EtOAc and water and basified to pH 14 with 6N NaOH. The phases were separated, and the aqueous phase was acidified to pH 4 with 6N HCl and the product was extracted into EtOAc. The organic layer was washed with sat'd NaCl and concentrated en vacuo. The residue was purified by reverse-phase HPLC (10-90% CH$_3$CN/H$_2$O, 0.1% TFA over 17 minutes, retention time 9.44 min) to provide 11 mg (32%) of the title compound as a white solid. MS (ES+) m/e 415 [M+H]$^+$ Example 103

N-(3-Chloro-1H-indazol-5-yl)-4-(4-chlorophenyl)-1,2-dimethyl-6-oxo-1,4,5,6-tetrahydro-3-pyridinecarboxamide

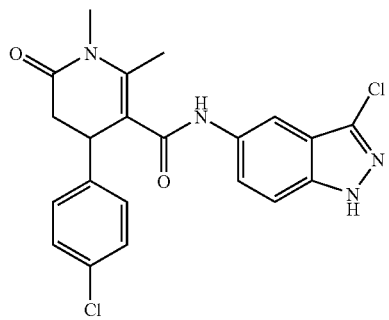

The title compound was prepared from the product of Example 56, Step 2 and 5-amino-3-chloroindazole using the method described in Example 56, Step 3. MS (ES+) m/e 430 [M+H]$^+$ Example 104

N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide

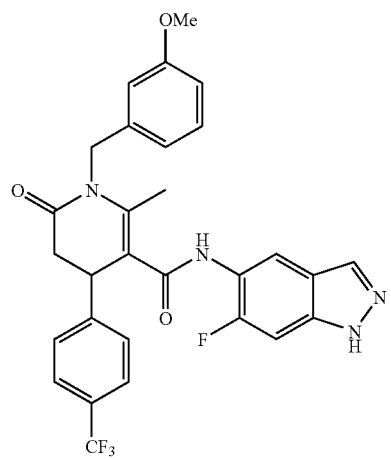

Step 1. Methyl 2-methyl-1-{[3-(methyloxy)phenyl]methyl}-6-oxo-4-[4-(trifluoromethyl)phenyl]-1,4,5,6-tetrahydro-3-pyridinecarboxylate The product from Example 5, Step 1 (0.627 g, 2.00 mmol, 1.00 equiv) and cesium carbonate (0.975 g, 3.00 mmol, 1.50 equiv) were combined in DMF (9 mL) for 15 minutes at rt. 3-Methoxybenzyl bromide (0.436 mL, 3.12 mmol, 1.56 equiv) was added and the reaction was heated to 100° C. for 6 hours. The reaction was diluted with H$_2$O and extracted with Et$_2$O. The organic phase was washed with H$_2$O and satd. NaCl, dried over MgSO$_4$ and concentrated en vacuo to provide 0.762 mg (88%) of the title compound as an oil. MS (ES+) m/e 434 [M+H]$^+$ Step 2. 2-Methyl-1-{[3-(methyloxy)phenyl]methyl}-6-oxo-4-[4-(trifluoromethyl)phenyl]-1,4,5,6-tetrahydro-3-pyridinecarboxylic acid The product from Step 1 (0.762 g, 1.76 mmol, 1.00 equiv) was dissolved in MeOH (20 mL) and NaOH (2.0 M, 3.5 mL) and the mixture was heated to reflux for 1.5 hours. The reaction was cooled to room temperature and concentrated en vacuo. The residue was dissolved in H$_2$O and 6N HCl was added to acidify the solution to pH 1. The crystalline precipitate was isolated by filtration, washed with H$_2$O and air dried. The residue was further dried en vacuo to provide 0.586 g (80%) of the product as an amorphous solid. MS (ES+) m/e 420 [M+H]$^+$

Step 3. N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide The title compound was prepared according to the general method described in Example 70, Step 3, beginning with the product of Example 104, Step 2. MS (ES+) m/e 553 [M+H]⁺

Example 105

1-Ethyl-N-(6-fluoro-1H-indazol-5-yl)-2-methyl-6-oxo-4-[4-(trifluoromethyl)phenyl]-1,4,5,6-tetrahydro-3-pyridinecarboxamide

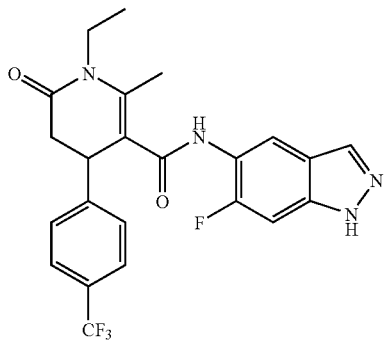

Step 1. Methyl 1-ethyl-2-methyl-6-oxo-4-[4-(trifluoromethyl)phenyl]-1,4,5,6-tetrahydro-3-pyridinecarboxylate The product from Example 5, Step 1 (0.627 g, 2.00 mmol, 1.00 equiv) was dissolved in DMF (9 mL) and sodium hydride (60% dispersion in mineral oil, 0.112 g, 1.40 equiv) was added. After the reaction had stirred for 20 minutes at room temperature, diethyl sulfate (0.314 mL, 2.40 mmol, 1.20 equiv) was added and the reaction was heated to 100° C. for 4 hours. The reaction was diluted with $H_2O$ and extracted with EtOAc. The organic phase was washed four times with $H_2O$ and once with satd. NaCl, dried over $MgSO_4$ and concentrated en vacuo to provide 0.627 g (92%) of the title compound as an oil. MS (ES+) m/e 342 [M+H]⁺

Step 2. 1-Ethyl-2-methyl-6-oxo-4-[4-(trifluoromethyl)phenyl]-1,4,5,6-tetrahydro-3-pyridinecarboxylic acid The title compound was prepared according to the general procedure described in Example 104, Step 2. MS (ES+) m/e 328 [M+H]⁺

Step 3. N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide The title compound was prepared according to the general method described in Example 70, Step 3, beginning with the product of Example 105, Step 2. MS (ES+) m/e 461 [M+H]⁺

Example 106

N-(6-Fluoro-1H-indazol-5-yl)-2-methyl-1-(2-methylpropyl)-6-oxo-4-[4-(trifluoromethyl)phenyl]-1,4,5,6-tetrahydro-3-pyridinecarboxamide

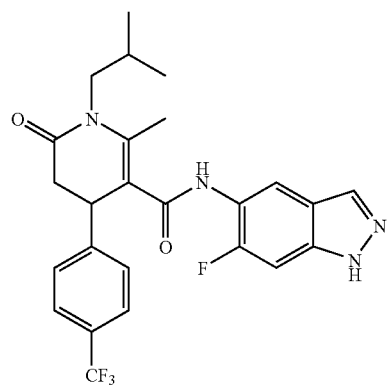

Step 1. Methyl 2-methyl-1-(2-methylpropyl)-6-oxo-4-[4-(trifluoromethyl)phenyl]-1,4,5,6-tetrahydro-3-pyridinecarboxylate The title compound was prepared according to the general procedure described in Example 104, Step 1 using isobutyl bromide in place of 3-methoxybenzyl bromide. MS (ES+) m/e 370 [M+H]⁺

Step 2. 2-Methyl-1-(2-methylpropyl)-6-oxo-4-[4-(trifluoromethyl)phenyl]-1,4,5,6-tetrahydro-3-pyridinecarboxylic acid The title compound was prepared according to the general procedure described in Example 104, Step 2. MS (ES+) m/e 356 [M+H]⁺

Step 3. N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide The title compound was prepared according to the general method described in Example 70, Step 3, beginning with the product of Example 106, Step 2. MS (ES+) m/e 489 [M+H]⁺

Example 107

1-[2-(Dimethylamino)-2-oxoethyl]-N-(6-fluoro-1H-indazol-5-yl)-2-methyl-6-oxo-4-[4-(trifluoromethyl)phenyl]-1,4,5,6-tetrahydro-3-pyridinecarboxamide

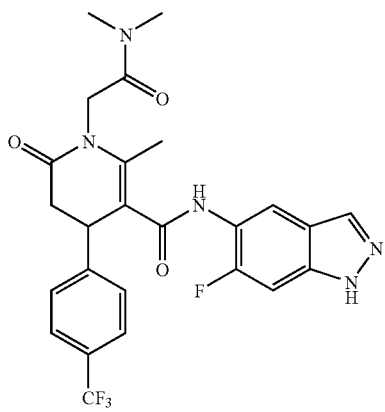

Step 1. Methyl 1-[2-(dimethylamino)-2-oxoethyl]-2-methyl-6-oxo-4-[4-(trifluoromethyl)phenyl]-1,4,5,6-tetrahydro-3-pyridinecarboxylate The title compound was prepared according to the general procedure described in Example 104, Step 1 using N,N-dimethylchloroacetamide in place of 3-methoxybenzyl bromide. MS (ES+) m/e 399 [M+H]$^+$

Step 2. 1-[2-(dimethylamino)-2-oxoethyl]-2-methyl-6-oxo-4-[4-(trifluoromethyl)phenyl]-1,4,5,6-tetrahydro-3-pyridinecarboxylic acid The title compound was prepared according to the general procedure described in Example 104, Step 2. MS (ES+) m/e 340 [M+H]$^+$

Step 3. N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide The title compound was prepared according to the general method described in Example 70, Step 3, beginning with the product of Example 107, Step 2. MS (ES+) m/e 473 [M+H]$^+$ ROCK Kinase Assay:

ROCK Kinase Assay:

ROCK inhibitor activity was determined using human recombinant ROCK1 kinase domain (amino acid 2-543) expressed in Sf9 cells (see WO9967283). The enzyme was purified using His-tag NTA column and Source15 HPLC chromatography. The assay of Rock-1 activity involved incubation with peptide substrate and ATP$^{33}$, the subsequent incorporation of P$^{33}$ into the peptide was quantified by Scintillation Proximity Assay (SPA—Amersham Pharmacia).

For IC50 determination, test compounds were typically dissolved at 10 mM in 100% DMSO, with subsequent serial dilution in 100% DMSO. Compounds were typically assayed over an eleven point dilution range with a concentration in the assay of 50 uM to 0.8 nM, in 3-fold dilutions. IC50) values were calculated by bespoke curve fitting software and then converted to pIC50. In some cases, compounds were assayed over an eleven point dilution range with a concentration in the assay of 10 uM to 0.8 nM, in 3-fold dilutions. For dose response curves in these cases, data were normalized and expressed as % inhibition using the formula 100*((U−C1)/(C2−C1)) where U is the unknown value, C1 is the average of the high signal (0%) control wells, and C2 is the average of the low signal (100%) control wells. Curve fitting was performed with the following equation: y=A+((B−A)/(10^/10^C)^D)), where A is the minimum response, B is the maximum response, C is the log 10 IC50, and D is the Hill slope. The results for each compound were recorded as pIC50 values (−C in the above equation). All Examples analyzed gave demonstrable activity in the ROCK kinase assay except compound Example number 104 which was not active in the range tested (10 uM to 0.8 nM).

Assays were performed in opaque, white walled, 384 well plates, in a total assay volume of 20 ul. In some cases, the total assay volume was 10 ul. The assays contained: 1 nM hROCK1; 1 uM biotinylated peptide (biotin-Ahx-AKRRRLSSLRA-CONH2); 1 uM ATP; 1.85 kBq per well ATP(□-33P); 25 mM Hepes pH 7.4; 15 mM MgCl$_2$; 0.015% BSA. The reactions were incubated at 22° C. for 120 minutes, then terminated by the addition of a 50 ul solution containing 60 mM EDTA and streptavidin PVT SPA beads. The SPA beads were added to a concentration of 0.14 mg per well. In some cases, the reactions were incubated at 22° C. for 90 minutes, then terminated by the addition of a 50 ul solution containing 60 mM EDTA and streptavidin PVT SPA beads at a concentration of 0.08 mg per well. Alternatively in cases where the total assay volume was 10 ul, the reactions were incubated at 22° C. for 90 minutes, then terminated by the addition of a 10 ul solution containing 150 mM EDTA and streptavidin coupled PS imaging beads at a concentration of 0.03 mg per well. In all cases, the plates were allowed to incubate at 22° C. for 10 minutes before centrifugation at 1500 rpm for 1 minute. P$^{33}$ incorporation was quantified by scintillation counting in a Packard TopCount. When the reaction was terminated by addition of a 10 ul solution, P33 incorporation was quantified by luminescence detection using a PerkinElmer Viewlux ultraHTS microplate imager.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I)

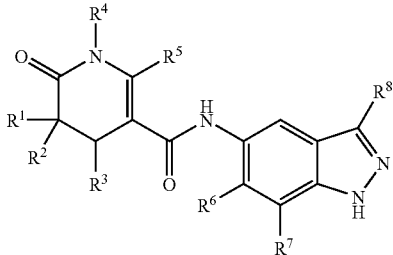

(I)

or a pharmaceutically acceptable salt thereof wherein:
$R^1$ and $R^2$, are, independently selected from the group consisting of hydrogen and $C_1$-$C_6$ alkyl;
$R^3$ is selected from the group consisting of phenyl optionally substituted with 1 to 3 substituents selected from the group consisting of F, Cl, trifluoromethyl, and phenyl; naphthyl; and quinolinyl;
$R^4$ is selected from the group consisting of hydrogen and methyl;
$R^5$ is $C_1$-$C_3$ alkyl;
$R^6$ is selected from the group consisting of chlorine, fluorine and hydrogen; and
$R^7$ and $R^8$, are, independently selected from the group consisting of hydrogen, halogen, and $C_1$-$C_3$ alkyl.

2. A compound according to claim 1 having formula (II)

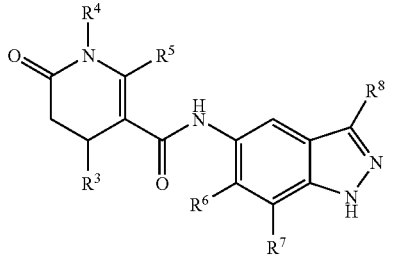

(II)

or a pharmaceutically acceptable salt thereof wherein:
$R^5$ is methyl;
$R^6$ is hydrogen; and
$R^7$ and $R^8$ are each hydrogen.

3. A compound or a pharmaceutically acceptable salt thereof, which compound is selected from the group consisting of
N-1H-Indazol-5-yl-2-methyl-4-(2-naphthalenyl)-6-oxo-1,4,5,6-tetrahydro-3-pyridinecarboxamide;
4-(4-Fluorophenyl)-N-1H-indazol-5-yl-2-methyl-6-oxo-1,4,5,6-tetrahydro-3-pyridinecarboxamide;
4-(4-Chloro-2-fluorophenyl)-N-1H-indazol-5-yl-2-methyl-6-oxo-1,4,5,6-tetrahydro-3-pyridinecarboxamide;
4-(4-Chlorophenyl)-N-1H-indazol-5-yl-2-methyl-6-oxo-1,4,5,6-tetrahydro-3-pyridinecarboxamide;
N-1H-Indazol-5-yl-2-methyl-6-oxo-4-[4-(trifluoromethyl)phenyl]-1,4,5,6-tetrahydro-3-pyridinecarboxamide;
4-(4-Biphenylyl)-N-1H-indazol-5-yl-2-methyl-6-oxo-1,4,5,6-tetrahydro-3-pyridinecarboxamide;
4-(3,4-Dichlorophenyl)-N-1H-indazol-5-yl-2-methyl-6-oxo-1,4,5,6-tetrahydro-3-pyridinecarboxamide;
4-(4-Fluorophenyl)-N-1H-indazol-5-yl-1,2-dimethyl-6-oxo-1,4,5,6-tetrahydro-3-pyridinecarboxamide;
4-[2-Fluoro-4-(trifluoromethyl)phenyl]-N-1H-indazol-5-yl-2-methyl-6-oxo-1,4,5,6-tetrahydro-3-pyridinecarboxamide;
N-1H-indazol-5-yl-2-methyl-6-oxo-4-(3-quinolinyl)-1,4,5,6-tetrahydro-3-pyridinecarboxamide;
N-(3-Chloro-1H-indazol-5-yl)-2-methyl-6-oxo-4-[4-(trifluoromethyl)phenyl]-1,4,5,6-tetrahydro-3-pyridinecarboxamide;
4-(4-Chloro-2-fluorophenyl)-N-(3-chloro-1H-indazol-5-yl)-2-methyl-6-oxo-1,4,5,6-tetrahydro-3-pyridinecarboxamide;
N-(3-Chloro-1H-indazol-5-yl)-2-methyl-4-(2-naphthalenyl)-6-oxo-1,4,5,6-tetrahydro-3-pyridinecarboxamide;
N-(3-Chloro-1H-indazol-5-yl)-4-(4-fluorophenyl)-2-methyl-6-oxo-1,4,5,6-tetrahydro-3-pyridinecarboxamide;
4-(4-Chloro-2-fluorophenyl)-N-(3-chloro-1H-indazol-5-yl)-2-methyl-6-oxo-1,4,5,6-tetrahydro-3-pyridinecarboxamide;
2-Methyl-N-(3-methyl-1H-indazol-5-yl)-6-oxo-4-[4-(trifluoromethyl)phenyl]-1,4,5,6-tetrahydro-3-pyridinecarboxamide;
N-(3-Bromo-1H-indazol-5-yl)-2-methyl-6-oxo-4-[4-(trifluoromethyl)phenyl]-1,4,5,6-tetrahydro-3-pyridinecarboxamide;
N-(3-Ethyl-1H-indazol-5-yl)-2-methyl-6-oxo-4-[4-(trifluoromethyl)phenyl]-1,4,5,6-tetrahydro-3-pyridinecarboxamide;
N-(6-Fluoro-1H-indazol-5-yl)-2-methyl-6-oxo-4-[4-(trifluoromethyl)phenyl]-1,4,5,6-tetrahydro-3-pyridinecarboxamide;
N-(7-Chloro-1H-indazol-5-yl)-2-methyl-6-oxo-4-[4-(trifluoromethyl)phenyl]-1,4,5,6-tetrahydro-3-pyridinecarboxamide;
2-Methyl-N-(7-methyl-1H-indazol-5-yl)-6-oxo-4-[4-(trifluoromethyl)phenyl]-1,4,5,6-tetrahydro-3-pyridinecarboxamide;
N-(3-Chloro-1H-indazol-5-yl)-4-[2-fluoro-4-(trifluoromethyl) phenyl]-2-methyl-6-oxo-1,4,5,6-tetrahydro-3-pyridinecarboxamide;
N-(3-Bromo-1H-indazol-5-yl)-4-[2-fluoro-4-(trifluoromethyl) phenyl]-2-methyl-6-oxo-1,4,5,6-tetrahydro-3-pyridinecarboxamide;
4-[2-Fluoro-4-(trifluoromethyl)phenyl]-2-methyl-N-(3-methyl-1H-indazol-5-yl)-6-oxo-1,4,5,6-tetrahydro-3-pyridinecarboxamide;
N-(3-Ethyl-1H-indazol-5-yl)-4-[2-fluoro-4-(trifluoromethyl) phenyl]-2-methyl-6-oxo-1,4,5,6-tetrahydro-3-pyridinecarboxamide;
N-(6-Fluoro-1 H-indazol-5-yl)-4-[2-fluoro-4-(trifluoromethyl) phenyl]-2-methyl-6-oxo-1,4,5,6-tetrahydro-3-pyridinecarboxamide;
4-[2-Fluoro-4-(trifluoromethyl)phenyl]-2-methyl-N-(7-methyl-1H-indazol-5-yl)-6-oxo-1,4,5,6-tetrahydro-3-pyridinecarboxamide;
N-(7-Chloro-1H-indazol-5-yl)-4-[2-fluoro-4-(trifluoromethyl) phenyl]-2-methyl-6-oxo-1,4,5,6-tetrahydro-3-pyridinecarboxamide;
4-(4-Chloro-2-fluorophenyl)-2-methyl-N-(3-methyl-1H-indazol-5-yl)-6-oxo-1,4,5,6-tetrahydro-3-pyridinecarboxamide;
N-(3-Bromo-1H-indazol-5-yl)-4-(4-chloro-2-fluorophenyl)-2-methyl-6-oxo-1,4,5,6-tetrahydro-3-pyridinecarboxamide;

4-(4-Chloro-2-fluorophenyl)-N-(3-ethyl-1H-indazol-5-yl)-2-methyl-6-oxo-1,4,5,6-tetrahydro-3-pyridinecarboxamide;
4-(4-Chloro-2-fluorophenyl)-N-(6-fluoro-1H-indazol-5-yl)-2-methyl-6-oxo-1,4,5,6-tetrahydro-3-pyridinecarboxamide;
4-(4-Chloro-2-fluorophenyl)-2-methyl-N-(7-methyl-1H-indazol-5-yl)-6-oxo-1,4,5,6-tetrahydro-3-pyridinecarboxamide;
4-(4-Chloro-2-fluorophenyl)-N-(7-chloro-1H-indazol-5-yl)-2-methyl-6-oxo-1,4,5,6-tetrahydro-3-pyridinecarboxamide;
N-(3-Bromo-1H-indazol-5-yl)-2-methyl-4-(2-naphthalenyl)-6-oxo-1,4,5,6-tetrahydro-3-pyridinecarboxamide;
2-Methyl-N-(3-methyl-1H-indazol-5-yl)-4-(2-naphthalenyl)-6-oxo-1,4,5,6-tetrahydro-3-pyridinecarboxamide;
N-(3-Ethyl-1H-indazol-5-yl)-2-methyl-4-(2-naphthalenyl)-6-oxo-1,4,5,6-tetrahydro-3-pyridinecarboxamide;
2-Methyl-N-(7-methyl-1H-indazol-5-yl)-4-(2-naphthalenyl)-6-oxo-1,4,5,6-tetrahydro-3-pyridinecarboxamide;
N-(7-Chloro-1H-indazol-5-yl)-2-methyl-4-(2-naphthalenyl)-6-oxo-1,4,5,6-tetrahydro-3-pyridinecarboxamide;
N-(3-Chloro-6-fluoro-1H-indazol-5-yl)-4-(4-chloro-2-fluorophenyl)-2-methyl-6-oxo-1,4,5,6-tetrahydro-3-pyridinecarboxamide;
4-(4-Chlorophenyl)-N-(6-fluoro-1 H-indazol-5-yl)-2-methyl-6-oxo-1,4,5,6-tetrahydro-3-pyridinecarboxamide;
N-1H-Indazol-5-yl-1 ,2-dimethyl-6-oxo-4-[4-(trifluoromethyl)phenyl]-1,4,5,6-tetrahydro-3-pyridinecarboxamide;
4-(3-Hydroxyphenyl)-N-1H-indazol-5-yl-2-methyl-6-oxo-1,4,5,6-tetrahydro-3-pyridinecarboxamide;
4-[4-(Aminosulfonyl)phenyl]-N-1H-indazol-5-yl-2-methyl-6-oxo-1,4,5,6-tetrahydro-3-pyridinecarboxamide;
4-(4-Cyanophenyl)-N-1H-indazol-5-yl-2-methyl-6-oxo-1,4,5,6-tetrahydro-3-pyridinecarboxamide;
N-(6-Fluoro-1H-indazol-5-yl)-4-[2-fluoro-4-(trifluoromethyl)phenyl]-1,2-dimethyl-6-oxo-1,4,5,6-tetrahydro-3-pyridinecarboxamide;
4-[2-Fluoro-4-(trifluoromethyl)phenyl]-1,2-dimethyl-N-(3-methyl-1H-indazol-5-yl)-6-oxo-1,4,5,6-tetrahydro-3-pyridinecarboxamide;
N-(3-Chloro-1H-indazol-5-yl)-4-[2-fluoro-4-(trifluoromethyl) phenyl]-1,2-dimethyl-6-oxo-1,4,5,6-tetrahydro-3-pyridinecarboxamide;
4-(4-Chloro-2-fluorophenyl)-1,2-dimethyl-N-(3-methyl-1H-indazol-5-yl)-6-oxo-1,4,5,6-tetrahydro-3-pyridinecarboxamide;
4-(4-Chloro-2-fluorophenyl)-N-(3-chloro-1H-indazol-5-yl)-1,2-dimethyl-6-oxo-1,4,5,6-tetrahydro-3-pyridinecarboxamide;
4-(4-Chloro-2-fluorophenyl)-N-(6-fluoro-1H-indazol-5-yl)-1,2-dimethyl-6-oxo-1,4,5,6-tetrahydro-3-pyridinecarboxamide;
N-(3-Chloro-6-fluoro-1H-indazol-5-yl)-2-methyl-6-oxo-4-[4-(trifluoromethyl)phenyl]-1,4,5,6-tetrahydro-3-pyridinecarboxamide;
N-(3-Chloro-6-fluoro-1H-indazol-5-yl)-4-[2-fluoro-4-(trifluoro-methyl)phenyl]-2-methyl-6-oxo-1,4,5,6-tetrahydro-3-pyridinecarboxamide;
N-(3-Chloro-6-fluoro-1H-indazol-5-yl)-4-(4-chlorophenyl)-2-methyl-6-oxo-1,4,5,6-tetrahydro-3-pyridinecarboxamide;
4-(4-Chlorophenyl)-2-methyl-N-(3-methyl-1H-indazol-5-yl)-6-oxo-1,4,5,6-tetrahydro-3-pyridinecarboxamide;
N-(6-Chloro-1H-indazol-5-yl)-4-(4-chlorophenyl)-2-methyl-6-oxo-1,4,5,6-tetrahydro-3-pyridinecarboxamide;
4-(4-Chlorophenyl)-N-1H-indazol-5-yl-1,2-dimethyl-6-oxo-1,4,5,6-tetrahydro-3-pyridinecarboxamide;
4-[2-Fluoro-4-(trifluoromethyl)phenyl]-N-1H-indazol-5-yl-1,2-dimethyl-6-oxo-1,4,5,6-tetrahydro-3-pyridinecarboxamide;
4-(4-Chloro-2-fluorophenyl)-N-1H-indazol-5-yl-1,2-dimethyl-6-oxo-1,4,5,6-tetrahydro-3-pyridinecarboxamide;
N-(3-Chloro-1H-indazol-5-yl)-1,2-dimethyl-6-oxo-4-[4-(trifluoromethyl)phenyl]-1,4,5,6-tetrahydro-3-pyridinecarboxamide;
N-(6-Fluoro-1H-indazol-5-yl)-1,2-dimethyl-6-oxo-4-[4-(trifluoromethyl)phenyl]-1,4,5,6-tetrahydro-3-pyridinecarboxamide;
4-(4-Chlorophenyl)-N-(6-fluoro-1H-indazol-5-yl)-1,2-dimethyl-6-oxo-1,4,5,6-tetrahydro-3-pyridinecarboxamide;
4-(4-Chlorophenyl)-1,2-dimethyl-N-(3-methyl-1H-indazol-5-yl)-6-oxo-1,4,5,6-tetrahydro-3-pyridinecarboxamide;
N-(6-Fluoro-1H-indazol-5-yl)-4-[2-fluoro-5-(methyloxy)phenyl]-2-methyl-6-oxo-1,4,5,6-tetrahydro-3-pyridinecarboxamide;
N-(6-Fluoro-1H-indazol-5-yl)-4-[2-fluoro-3-(methyloxy)phenyl]-2-methyl-6-oxo-1,4,5,6-tetrahydro-3-pyridinecarboxamide;
4-(2-Fluoro-5-hydroxyphenyl)-N-(6-fluoro-1H-indazol-5-yl)-2-methyl-6-oxo-1,4,5,6-tetrahydro-3-pyridinecarboxamide;
4-(2-Fluoro-3-hydroxyphenyl)-N-(6-fluoro-1H-indazol-5-yl)-2-methyl-6-oxo-1,4,5,6-tetrahydro-3-pyridinecarboxamide;
4-[5-(Aminosulfonyl)-4-chloro-2-fluorophenyl]-N-(6-fluoro-1H-indazol-5-yl)-2-methyl-6-oxo-1,4,5,6-tetrahydro-3-pyridinecarboxamide;
4-[3-(Aminosulfonyl)-4-chlorophenyl]-N-(6-fluoro-1H-indazol-5-yl)-2-methyl-6-oxo-1,4,5,6-tetrahydro-3-pyridinecarboxamide;
4-[3-(Aminosulfonyl)phenyl]-N-(6-fluoro-1H-indazol-5-yl)-2-methyl-6-oxo-1,4,5,6-tetrahydro-3-pyridinecarboxamide;
4-(2,3-Difluorophenyl)-N-(6-fluoro-1H-indazol-5-yl)-2-methyl-6-oxo-1,4,5,6-tetrahydro-3-pyridinecarboxamide;
4-(2,3-Difluorophenyl)-N-1H-indazol-5-yl-2-methyl-6-oxo-1,4,5,6-tetrahydro-3-pyridinecarboxamide;
4-(2,4-Difluorophenyl)-N-(6-fluoro-1H-indazol-5-yl)-2-methyl-6-oxo-1,4,5,6-tetrahydro-3-pyridinecarboxamide;
4-(2,4-Difluorophenyl)-N-(1H-indazol-5-yl)-2-methyl-6-oxo-1,4,5,6-tetrahydro-3-pyridinecarboxamide;
N-(6-Fluoro-1H-indazol-5-yl)-4-(3-hydroxyphenyl)-2-methyl-6-oxo-1,4,5,6-tetrahydro-3-pyridinecarboxamide;
N-(6-Fluoro-1H-indazol-5-yl)-2-methyl-4-{3-[(methylsulfonyl)amino]phenyl}-6-oxo-1,4,5,6-tetrahydro-3-pyridinecarboxamide;
4-(4-Chloro-3-nitrophenyl)-N-(6-fluoro-1H-indazol-5-yl)-2-methyl-6-oxo-1,4,5,6-tetrahydro-3-pyridinecarboxamide;
4-(3-Amino-4-chlorophenyl)-N-(6-fluoro-1H-indazol-5-yl)-2-methyl-6-oxo-1,4,5,6-tetrahydro-3-pyridinecarboxamide;

4-{4-Chloro-3-[(methylsulfonyl)amino]phenyl}-N-(6-fluoro-1H-indazol-5-yl)-2-methyl-6-oxo-1,4,5,6-tetrahydro-3-pyridinecarboxamide;

N-(6-Fluoro-1H-indazol-5-yl)-2-methyl-4-[3-nitro-4-(trifluoromethyl)phenyl]-6-oxo-1,4,5,6-tetrahydro-3-pyridinecarboxamide;

4-[3-Amino-4-(trifluoromethyl)phenyl]-N-(6-fluoro-1H-indazol-5-yl)-2-methyl-6-oxo-1,4,5,6-tetrahydro-3-pyridinecarboxamide;

N-(6-Fluoro-1H-indazol-5-yl)-2-methyl-4-[3-[(methylsulfonyl) amino]-4-(trifluoromethyl)phenyl]-6-oxo-1,4,5,6-tetrahydro-3-pyridinecarboxamide;

4-[3-[(Ethylsulfonyl)amino]-4-(trifluoromethyl)phenyl]-N-(6-fluoro-1H-indazol-5-yl)-2-methyl-6-oxo-1,4,5,6-tetrahydro-3-pyridinecarboxamide;

N-(6-Fluoro-1H-indazol-5-yl)-4-(2-fluoro-5-nitrophenyl)-2-methyl-6-oxo-1,4,5,6-tetrahydro-3-pyridinecarboxamide;

N-(6-Fluoro-1H-indazol-5-yl)-4-[4-fluoro-3-(trifluoromethyl)phenyl]-2-methyl-6-oxo-1,4,5,6-tetrahydro-3-pyridinecarboxamide;

4-[2,3-Difluoro-4-(trifluoromethyl)phenyl]-N-(6-fluoro-1H-indazol-5-yl)-2-methyl-6-oxo-1,4,5,6-tetrahydro-3-pyridinecarboxamide;

N-(6-Fluoro-1H-indazol-5-yl)-4-[3-fluoro-4-(trifluoromethyl) phenyl]-2-methyl-6-oxo-1,4,5,6-tetrahydro-3-pyridinecarboxamide;

4-(4-Cyanophenyl)-N-(6-fluoro-1H-indazol-5-yl)-2-methyl-6-oxo-1,4,5,6-tetrahydro-3-pyridinecarboxamide;

4-(4-Biphenylyl)-N-(6-fluoro-1H-indazol-5-yl)-2-methyl-6-oxo-1,4,5,6-tetrahydro-3-pyridinecarboxamide;

N-(6-Fluoro-1H-indazol-5-yl)-2-methyl-6-oxo-4-[4-(2-thienyl)phenyl]-1,4,5,6-tetrahydro-3-pyridinecarboxamide;

4-(4-Bromophenyl)-N-(6-fluoro-1H-indazol-5-yl)-2-methyl-6-oxo-1,4,5,6-tetrahydro-3-pyridinecarboxamide;

4-(5-Cyano-2-fluorophenyl)-N-(6-fluoro-1H-indazol-5-yl)-2-methyl-6-oxo-1,4,5,6-tetrahydro-3-pyridinecarboxamide;

N-(6-Fluoro-1H-indazol-5-yl)-4-[2-fluoro-4-(methyloxy)phenyl]-2-methyl-6-oxo-1,4,5,6-tetrahydro-3-pyridinecarboxamide;

N-(3-Chloro-1H-indazol-5-yl)-4-[4-chloro-3-(methyloxy)phenyl]-2-methyl-6-oxo-1,4,5,6-tetrahydro-3-pyridinecarboxamide;

N-(3-Bromo-1H-indazol-5-yl)-4-[4-chloro-3-(methyloxy)phenyl]-2-methyl-6-oxo-1,4,5,6-tetrahydro-3-pyridinecarboxamide;

4-[4-Chloro-3-(methyloxy)phenyl]-2-methyl-N-(3-methyl-1H-indazol-5-yl)-6-oxo-1,4,5,6-tetrahydro-3-pyridinecarboxamide;

4-[4-Chloro-3-(methyloxy)phenyl]-N-(3-ethyl-1H-indazol-5-yl)-2-methyl-6-oxo-1,4,5,6-tetrahydro-3-pyridinecarboxamide;

4-[4-Chloro-3-(methyloxy)phenyl]-N-(6-fluoro-1H-indazol-5-yl)-2-methyl-6-oxo-1,4,5,6-tetrahydro-3-pyridinecarboxamide;

4-(4-Chloro-3-hydroxyphenyl)-N-(3-chloro-1H-indazol-5-yl)-2-methyl-6-oxo-1,4,5,6-tetrahydro-3-pyridinecarboxamide;

N-(3-Bromo-1H-indazol-5-yl)-4-(4-chloro-3-hydroxyphenyl)-2-methyl-6-oxo-1,4,5,6-tetrahydro-3-pyridinecarboxamide;

4-(4-Chloro-3-hydroxyphenyl)-2-methyl-N-(3-methyl-1H-indazol-5-yl)-6-oxo-1,4,5,6-tetrahydro-3-pyridinecarboxamide;

4-(4-Chloro-3-hydroxyphenyl)-N-(3-ethyl-1H-indazol-5-yl)-2-methyl-6-oxo-1,4,5,6-tetrahydro-3-pyridinecarboxamide;

4-(4-Chloro-3-hydroxyphenyl)-N-(6-fluoro-1H-indazol-5-yl)-2-methyl-6-oxo-1,4,5,6-tetrahydro-3-pyridinecarboxamide;

N-(3-Chloro-1H-indazol-5-yl)-4-(4-chlorophenyl)-1,2-dimethyl-6-oxo-1,4,5,6-tetrahydro-3-pyridinecarboxamide;

N-(6-Fluoro-1H-indazol-5-yl)-2-methyl-1-{[3-(methyloxy)phenyl]methyl}-6-oxo-4-[4-(trifluoromethyl)phenyl]-1,4,5,6-tetrahydro-3-pyridinecarboxamide;

1-Lthyl-N-(6-fluoro-1H-indazol-5-yl)-2-methyl-6-oxo-4-[4-(trifluoromethyl)phenyl]-1,4,5,6-tetrahydro-3-pyridinecarboxamide;

N-(6-Fluoro-1H-indazol-5-yl)-2-methyl-1-(2-methylpropyl)-6-oxo-4-[4-(trifluoromethyl)phenyl]-1,4,5,6-tetrahydro-3-pyridinecarboxamide; and 1-[2-(Dimethylamino)-2-oxoethyl]-N-(6-fluoro-1H-indazol-5-yl)-2-methyl-6-oxo-4-[4-(trifluoromethyl)phenyl]-1,4,5,6-tetrahydro-3-pyridinecarboxamide.

4. A method of treating glaucoma comprising administering to a subject in need thereof a therapeutically effective amount of a compound according to claim 1 or a pharmaceutically acceptable salt thereof.

5. A pharmaceutical composition comprising a compound according to claim 1 or a pharmaceutically acceptable salt thereof; and a suitable carrier.

6. A compound or a pharmaceutically acceptable salt thereof, which compound is selected from the group consisting of:

N-1H-Indazol-5-yl-2-methyl-4-(2-naphthalenyl)-6-oxo-1,4,5,6-tetrahydro-3-pyridinecarboxamide;

4-(4-Fluorophenyl)-N-1H-indazol-5-yl-2-methyl-6-oxo-1,4,5,6-tetrahydro-3-pyridinecarboxamide;

4-(4-Chloro-2-fluorophenyl)-N-1H-indazol-5-yl-2-methyl-6-oxo-1,4,5,6-tetrahydro-3-pyridinecarboxamide;

4-(4-Chlorophenyl)-N-1H-indazol-5-yl-2-methyl-6-oxo-1,4,5,6-tetrahydro-3-pyridinecarboxamide;

N-1H-Indazol-5-yl-2-methyl-6-oxo-4-[4-(trifluoromethyl)phenyl]-1,4,5,6-tetrahydro-3-pyridinecarboxamide;

4-(4-Biphenylyl)-N-1H-indazol-5-yl-2-methyl-6-oxo-1,4,5,6-tetrahydro-3-pyridinecarboxamide;

4-(3,4-Dichlorophenyl)-N-1H-indazol-5-yl-2-methyl-6-oxo-1,4,5,6-tetrahydro-3-pyridinecarboxamide;

4-[2-Fluoro-4-(trifluoromethyl)phenyl]-N-1H-indazol-5-yl-2-methyl-6-oxo-1,4,5,6-tetrahydro-3-pyridinecarboxamide; and N-1H-Indazol-5-yl-2-methyl-6-oxo-4-(3-quinolinyl)-1,4,5,6-tetrahydro-3-pyridinecarboxamide.

7. The compound of claim 6 which is N-1H-Indazol-5-yl-2-methyl-4-(2-naphthalenyl)-6-oxo-1,4,5,6-tetrahydro-3-pyridinecarboxamide or a pharmaceutically acceptable salt thereof.

8. The compound of claim 6 which is 4-(4-Fluorophenyl)-N-1H-indazol-5-yl-2-methyl-6-oxo-1,4,5,6-tetrahydro-3-pyridinecarboxamide or a pharmaceutically acceptable salt thereof.

9. The compound of claim 6 which is 4-(4-Chloro-2-fluorophenyl)-N-1H-indazol-5-yl-2-methyl-6-oxo-1,4,5,6-tetrahydro-3-pyridinecarboxamide or a pharmaceutically acceptable salt thereof.

10. The compound of claim 6 which is 4-(4-Chlorophenyl)-N-1H-indazol-5-yl-2-methyl-6-oxo-1,4,5,6-tetrahydro-3-pyridinecarboxamide or a pharmaceutically acceptable salt thereof.

11. The compound of claim 6 which is N-1H-Indazol-5-yl-2-methyl-6-oxo-4-[4-(trifluoromethyl)phenyl]-1,4,5,6-tetrahydro-3-pyridinecarboxamide or a pharmaceutically acceptable salt thereof.

12. The compound of claim 6 which is 4-(4-Biphenylyl)-N-1H-indazol-5-yl-2-methyl-6-oxo-1,4,5,6-tetrahydro-3-pyridinecarboxamide or a pharmaceutically acceptable salt thereof.

13. The compound of claim 6 which is 4-(3,4-Dichlorophenyl)-N-1H-indazol-5-yl-2-methyl-6-oxo-1,4,5,6-tetrahydro-3-pyridinecarboxamide or a pharmaceutically acceptable salt thereof.

14. The compound of claim 6 which is 4-[2-Fluoro-4-(trifluoromethyl)phenyl]-N-1H-indazol-5-yl-2-methyl-6-oxo-1,4,5,6-tetrahydro-3-pyridinecarboxamide or a pharmaceutically acceptable salt thereof.

15. The compound of claim 6 which is N-1H-Indazol-5-yl-2-methyl-6-oxo-4-(3-quinolinyl)-1,4,5,6-tetrahydro-3-pyridinecarboxamide or a pharmaceutically acceptable salt thereof.

16. A method of treating glaucoma comprising administering to a subject in need thereof a therapeutically effective amount of a compound according to claim 6 or a pharmaceutically acceptable salt thereof.

17. A pharmaceutical composition comprising a compound according to claim 6 or a pharmaceutically acceptable salt thereof and a suitable carrier.

* * * * *